(12) United States Patent
Cho et al.

(10) Patent No.: US 10,945,710 B2
(45) Date of Patent: Mar. 16, 2021

(54) ULTRASOUND PROBE AND OPERATING METHOD THEREOF

(71) Applicant: SAMSUNG ELECTRONICS CO., LTD., Suwon-si (KR)

(72) Inventors: Jeong Cho, Seoul (KR); Ho-san Han, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 834 days.

(21) Appl. No.: 14/845,596

(22) Filed: Sep. 4, 2015

(65) Prior Publication Data
US 2016/0066893 A1 Mar. 10, 2016

(30) Foreign Application Priority Data

Sep. 4, 2014 (KR) .................. 10-2014-0118018
Feb. 24, 2015 (KR) .................. 10-2015-0025904
May 29, 2015 (KR) .................. 10-2015-0076489

(51) Int. Cl.
*A61B 8/14* (2006.01)
*A61B 8/00* (2006.01)
*G01S 7/52* (2006.01)

(52) U.S. Cl.
CPC .............. *A61B 8/56* (2013.01); *A61B 8/4472* (2013.01); *A61B 8/54* (2013.01); *G01S 7/5208* (2013.01);
(Continued)

(58) Field of Classification Search
CPC ... G01N 29/24; G01S 7/5208; G01S 7/52082; G01S 7/52084; G01S 7/52096;
(Continued)

(56) References Cited

U.S. PATENT DOCUMENTS 7,984,651 B2 7/2011 Randall et al.
10,129,926 B2 11/2018 Kim et al.
(Continued)

FOREIGN PATENT DOCUMENTS

CN 103717140 A 4/2014
JP 2007275087 A 10/2007
(Continued)

OTHER PUBLICATIONS

Communication dated Feb. 3, 2016, issued by the European Patent Office in counterpart European Application No. 15183684.8.
(Continued)

*Primary Examiner* — Mark D Remaly
(74) *Attorney, Agent, or Firm* — Sughrue Mion, PLLC

(57) ABSTRACT

Disclosed is a method for operating an ultrasound probe which is wirelessly connected to an ultrasound image providing apparatus via a communication channel. The method includes acquiring bandwidth information that relates to the communication channel, determining at least one from among at least one parameter value associated with a quality of an ultrasound image and a transmission speed of a frame that constitutes the ultrasound image, based on the bandwidth information, generating ultrasound image data that relates to an object, based on the at least one parameter value, and transmitting the ultrasound image data to the ultrasound image providing apparatus. The ultrasound image data is used to display the ultrasound image by using the ultrasound image providing apparatus.

7 Claims, 32 Drawing Sheets

(52) U.S. Cl.
CPC ...... *G01S 7/52082* (2013.01); *G01S 7/52084* (2013.01); *G01S 7/52096* (2013.01)

(58) Field of Classification Search
CPC ... A61B 5/0022; A61B 8/4444; A61B 8/4472; A61B 8/5207; A61B 8/54; A61B 8/56
See application file for complete search history.

(56) References Cited

U.S. PATENT DOCUMENTS

| | | | |
|---|---|---|---|
| 2003/0181811 A1 | 9/2003 | Amemiya et al. | |
| 2005/0226182 A1* | 10/2005 | Itoh | H04L 1/0009 370/329 |
| 2008/0110263 A1* | 5/2008 | Klessel | G01S 7/52028 73/602 |
| 2008/0114249 A1 | 5/2008 | Randall et al. | |
| 2010/0017564 A1* | 1/2010 | Heo | G06F 3/061 711/112 |
| 2010/0262005 A1 | 10/2010 | Karasawa | |
| 2010/0286527 A1 | 11/2010 | Cannon et al. | |
| 2012/0141002 A1 | 6/2012 | Urbano et al. | |
| 2013/0028153 A1 | 1/2013 | Kim et al. | |
| 2014/0169163 A1* | 6/2014 | Bush | H04L 47/12 370/230 |
| 2014/0180110 A1 | 6/2014 | Schmedling | |
| 2014/0194739 A1 | 7/2014 | Katou | |
| 2015/0065882 A1 | 3/2015 | Cho et al. | |

FOREIGN PATENT DOCUMENTS

| | | |
|---|---|---|
| KR | 10-2015-0027010 A | 3/2015 |
| WO | 2013162244 A1 | 10/2013 |

OTHER PUBLICATIONS

Communication dated Dec. 17, 2015, issued by the International Searching Authority in counterpart International Application No. PCT/KR2015/009323 (PCT/ISA/210 & PCT/ISA/237).

Communication dated Mar. 25, 2019, from the State Intellectual Property Office of People's Republic of China in counterpart Application No. 201580047443.9.

* cited by examiner

WHEN BANDWIDTH IS REDUCED BY 1/2

810  256 SCAN LINES 60 FRAME/SEC Wigig 820  512 SCAN LINES 30 FRAME/SEC Wigig 830  512 SCAN LINES 60 FRAME/SEC Wifi

1310

1320

WHEN IMAGE QUALITY PARAMETER IS
REDUCED BY 1/2 BASED ON USER INPUT

REDUCTION IN TRANSMISSION SPEED ∴ REDUCTION IN POWER CONSUMPTION

ULTRASOUND PROBE AND OPERATING METHOD THEREOF

CROSS-REFERENCE TO RELATED APPLICATIONS

This application claims priority from Korean Patent Application No. 10-2014-0118018, filed on Sep. 4, 2014, Korean Patent Application No. 10-2015-0025904, filed on Feb. 24, 2015, and Korean Patent Application No. 10-2015-0076489, filed on May 29, 2015 in the Korean Intellectual Property Office, the disclosures of which are incorporated herein by reference in their respective entireties.

BACKGROUND

1. Field

One or more exemplary embodiments relate to an ultrasound probe that supplies ultrasound image data to an ultrasound image providing apparatus and an operating method thereof, and more particularly, to an ultrasound probe and an operating method thereof, which adaptively change an image quality and a transmission speed of ultrasound image data supplied to an ultrasound image providing apparatus.

2. Description of the Related Art

An ultrasound system irradiates an ultrasound signal, generated from a transducer of a probe, onto an object and receives information of an echo signal reflected from the object, thereby obtaining an image of an internal part of the object. In particular, an ultrasound system is used for the medical purpose of observing the inside of an object, detecting a foreign material, and assessing an injury.

The ultrasound system has stabilities higher than those of diagnostic apparatuses that uses X-rays, displays an image in real time, and is relatively safe because there is no exposure to radioactivity, and thus may be widely used.

A user may experience some difficulty in obtaining an image of an object by using an ultrasound probe due to a communication cable that connects the ultrasound probe to an ultrasound image providing apparatus. In order to enhance a manipulability of an ultrasound probe by solving the difficulty, an ultrasound probe that accesses an ultrasound image providing apparatus via wireless communication is needed.

A communication channel cannot always maintain a constant operational state in an environment in which an ultrasound image providing apparatus is wirelessly connected to an ultrasound probe via the communication channel. For example, even when the ultrasound image providing apparatus transmits or receives data to or from the ultrasound probe so as to be suitable for an initial bandwidth of the communication channel, a characteristic of the communication channel may be changed by an environment. Therefore, it is required to develop an ultrasound probe and an operating method thereof, which adaptively transmit ultrasound image data, based on a state of the communication channel.

Moreover, since an ultrasound probe which is wirelessly connected to the ultrasound image providing apparatus is capable of being carried by a user, a size of the ultrasound probe is restricted, and the ultrasound probe may include only limited resources. Therefore, in an environment where the ultrasound image providing apparatus is wirelessly connected to the ultrasound probe, the ultrasound probe may transmit ultrasound image data to the ultrasound image providing apparatus under conditions where power consumption is minimized.

When an ultrasound probe is dependent on one ultrasound image providing apparatus, a plurality of ultrasound probes need to be provided depending on each ultrasound image providing apparatus, which is costly and difficult to manage. Therefore, an ultrasound probe needs to communicate with a plurality of ultrasound image providing apparatuses without being dependent on one ultrasound image providing apparatus.

SUMMARY

One or more exemplary embodiments include an ultrasound probe and an operating method thereof, which adaptively transmit ultrasound image data, based on a state of a communication channel.

One or more exemplary embodiments include an ultrasound probe and an operating method thereof, which adaptively transmit ultrasound image data according to a user input.

One or more exemplary embodiments include an ultrasound probe and an operating method thereof, which adaptively transmit ultrasound image data based on a characteristic of an ultrasound image providing apparatus.

Additional aspects will be set forth in part in the description which follows and, in part, will be apparent from the description, or may be learned by practice of the presented exemplary embodiments.

According to one or more exemplary embodiments, a method for operating an ultrasound probe, which is wirelessly connected to an ultrasound image providing apparatus via a communication channel, includes: acquiring bandwidth information that relates to the communication channel; determining at least one parameter value that relates to a quality of an ultrasound image, based on the bandwidth information; generating ultrasound image data that relates to an object, based on the determined at least one parameter value; and transmitting the generated ultrasound image data to the ultrasound image providing apparatus.

The ultrasound probe may include: an ultrasound transceiver configured to transmit an ultrasound signal toward the object, and to receive an echo signal reflected from the object; and a signal processor configured to process the received echo signal. The generating of the ultrasound image data may include controlling at least one of the ultrasound transceiver and the signal processor to generate the ultrasound image data, based on the at least one parameter value.

The at least one parameter value associated with the quality of the ultrasound image may include at least one selected from among a number of scan lines constituting a frame of the ultrasound image, a number of sampling points which are set on a scan line, and a number of bits which are generated by quantizing data which is acquired with respect to a sampling point.

The determining of the at least one parameter value may include, when the bandwidth of the communication channel is narrowed, reducing at least one selected from among a number of scan lines constituting the frame of the ultrasound image, a number of sampling points which are set on a scan line, and a number of bits which are generated by quantizing data which is acquired with respect to a sampling point, based on an amount of narrowing of the bandwidth.

The method may further include selecting one mode from among first and second modes, based on an application used by the ultrasound probe. The determining of the at least one parameter value may include: when the first mode is selected, adjusting the at least one parameter value, based on a change in the bandwidth of the communication channel; and when the second mode is selected, adjusting a transmission speed at which the ultrasound image data is transmitted to the ultrasound image providing apparatus, based on the change in the bandwidth of the communication channel.

The method may further include mapping one of the first and second modes to each of a plurality of applications, and storing the mapped mode, wherein the selecting of the one mode may include selecting a mode which is stored to be mapped to an application used by the ultrasound probe.

The determining of the at least one parameter value may include: selecting one mode from among first and second modes, based on a user input; when the first mode is selected, adjusting the at least one parameter value, based on a change in the bandwidth of the communication channel; and when the second mode is selected, adjusting the transmission speed at which the ultrasound image data is transmitted to the ultrasound image providing apparatus, based on the change in the bandwidth of the communication channel.

The acquiring of the bandwidth information may include: transmitting a session establishment request signal to the ultrasound image providing apparatus; receiving a session establishment check signal from the ultrasound image providing apparatus; and extracting the bandwidth information from the session establishment check signal.

The transmitting of the ultrasound image data may include transmitting, to the ultrasound image providing apparatus, information about at least one selected from the at least one parameter value and the transmission speed at which the ultrasound image data is transmitted to the ultrasound image providing apparatus in conjunction with the ultrasound image data, and the information about at least one selected from the at least one parameter value and the transmission speed may be usable by the ultrasound image providing apparatus for generating an ultrasound image from the ultrasound image data.

The determining of the at least one parameter value may include adjusting, based on a user input, the at least one parameter value and a transmission speed at which the ultrasound image data is transmitted to the ultrasound image providing apparatus.

The ultrasound probe may be connectable to a plurality of ultrasound image providing apparatuses, including the ultrasound image providing apparatus, via different communication channels, and the transmitting of the ultrasound image data may include: generating a plurality of transmission streams by processing the ultrasound image data, based on respective characteristics of each of the plurality of ultrasound image providing apparatuses; and transmitting each of the plurality of transmission streams to a corresponding one of the plurality of ultrasound image providing apparatuses via a corresponding one of the different communication channels, respectively.

According to one or more exemplary embodiments, a method of operating an ultrasound probe includes: wirelessly connecting the ultrasound probe to an ultrasound image providing apparatus by using a first communication scheme; acquiring bandwidth information that defines a transmission speed of ultrasound image data with respect to the first communication scheme from the ultrasound probe to the ultrasound image apparatus; when the transmission speed is lower than a threshold speed, wirelessly connecting the ultrasound probe to the ultrasound image providing apparatus by using a second communication scheme; and transmitting ultrasound image data that relates to an object to the ultrasound image providing apparatus by using the second communication scheme.

According to one or more exemplary embodiments, a method of operating an ultrasound probe, wirelessly connected to an ultrasound image providing apparatus through a communication channel, includes: acquiring bandwidth information that relates to the communication channel; determining a transmission speed of a frame of an ultrasound image based on the acquired bandwidth information; generating ultrasound image data about an object; and transmitting the ultrasound image data to the ultrasound image providing apparatus at the determined transmission speed.

The determining of the transmission speed may include, when the bandwidth of the communication channel is narrowed, reducing the transmission speed based on an amount of narrowing of the bandwidth.

The transmitting of the ultrasound image data may include, when the bandwidth of the communication channel is narrowed, reducing an amount of data that is contained in each frame of the ultrasound image based on the reduced transmission speed.

The ultrasound probe may be connectable to a plurality of ultrasound image providing apparatuses, including the ultrasound image providing apparatus, via different communication channels, and the transmitting of the ultrasound image data may include: generating a plurality of transmission streams by processing the ultrasound image data, based on respective characteristics of each of the plurality of ultrasound image providing apparatuses; and transmitting each of the plurality of transmission streams to a corresponding one of the plurality of ultrasound image providing apparatuses via a corresponding one of the different communication channels.

According to one or more exemplary embodiments, an ultrasound probe, wirelessly connected to an ultrasound image providing apparatus via a communication channel, includes: an ultrasound transceiver configured to transmit an ultrasound signal to an object, and to receive an echo signal; a signal processor configured to process the echo signal; a controller configured to acquire bandwidth information of the communication channel, to determine at least one parameter value associated with a quality of an ultrasound image, based on the bandwidth information, and to control the ultrasound transceiver and the signal processor to generate ultrasound image data about the object, based on the determined at least one parameter value; and a communicator configured to transmit the ultrasound image data to the ultrasound image providing apparatus.

According to one or more exemplary embodiments, an ultrasound probe, wirelessly connected to an ultrasound image providing apparatus via a communication channel, includes: an ultrasound transceiver configured to transmit an ultrasound signal to an object, and to receive an echo signal; a signal processor configured to process the echo signal; a controller configured to acquire bandwidth information of the communication channel, to determine a transmission speed of a frame constituting an ultrasound image, based on the bandwidth information, and to control at least one selected from among the ultrasound transceiver and the signal processor to generate ultrasound image data about the object; and a communicator configured to transmit the ultrasound image data to the ultrasound image providing apparatus at the determined transmission speed.

According to one or more exemplary embodiments, an ultrasound probe includes: an ultrasound transceiver configured to transmit an ultrasound signal to an object and to receive an echo signal; a signal processor configured to process the echo signal in order to generate ultrasound image data about the object; a communicator configured to transmit the ultrasound image data to an ultrasound image providing apparatus; and a controller configured to control the communicator to wirelessly connect the ultrasound probe to the ultrasound image providing apparatus by using a first communication scheme, to acquire bandwidth information that defines a transmission speed of ultrasound image data based on the first communication scheme, and when the transmission speed is lower than a threshold speed, to control the communicator to wirelessly connect the ultrasound probe to the ultrasound image providing apparatus by using a second communication scheme and to transmit the ultrasound image data to the ultrasound image providing apparatus by using the second communication scheme.

According to one or more exemplary embodiments, an ultrasound probe, wirelessly connected to an ultrasound image providing apparatus, includes: an ultrasound transceiver configured to transmit an ultrasound signal to an object, and to receive an echo signal; a signal processor configured to process the echo signal; a controller configured to determine at least one parameter value associated with ultrasound image quality, based on a user input, and to control at least one selected from among the ultrasound transceiver and the signal processor to generate ultrasound image data about an object, based on the determined at least one parameter value; and a communicator configured to transmit the ultrasound image data to the ultrasound image providing apparatus at the transmission speed determined based on the determined at least one parameter value.

The at least one parameter value associated with the ultrasound image quality may include at least one selected from among a number of scan lines constituting the frame of the ultrasound image, a number of sampling points which are set on a scan line, and a number of bits which are generated by quantizing data which is acquired with respect to a sampling point, and the communicator may be further configured transmit the ultrasound image data at a transmission speed which is reduced based on a reduction in the at least one parameter value.

The ultrasound probe may be connected to the plurality of ultrasound image providing apparatuses, including the ultrasound image providing apparatus, via different communication channels. The controller may be further configured to generate a plurality of transmission streams by processing the ultrasound image data, based on respective characteristics of the plurality of ultrasound image providing apparatuses, and the communicator may be further configured transmit each of the plurality of transmission streams to a corresponding one of the plurality of ultrasound image providing apparatuses via a corresponding one of the different communication channels.

According to one or more exemplary embodiments, an ultrasound probe, wirelessly connected to an ultrasound image providing apparatus, includes: an ultrasound transceiver configured to transmit an ultrasound signal to an object, and to receive an echo signal; a signal processor configured to process the echo signal; a controller configured to determine a transmission speed for transmitting ultrasound image data, based on a user input, to determine at least one parameter value associated with ultrasound image quality, based on the determined transmission speed, and to control the ultrasound transceiver and the signal processor to generate ultrasound image data about an object, based on the determined at least one parameter value; and a communicator configured to transmit the ultrasound image data to the ultrasound image providing apparatus at the determined transmission speed.

The controller may be further configured to decrease the at least one parameter value, based on a reduction in the transmission speed.

The ultrasound probe may be connected to the plurality of ultrasound image providing apparatuses, including the ultrasound image providing apparatus, via different communication channels. Also, the controller may be further configured to generate a plurality of transmission streams by processing the ultrasound image data, based on respective characteristics of the plurality of ultrasound image providing apparatuses, and the communicator may be further configured to transmit each of the plurality of transmission streams to a corresponding one of the plurality of ultrasound image providing apparatuses via a corresponding one of the different communication channels.

According to one or more exemplary embodiments, a method for operating an ultrasound probe includes: acquiring information about an ultrasound image providing apparatus that is wirelessly connected to the ultrasound probe; determining a transmission speed of ultrasound image data about an object, based on the information about the ultrasound image providing apparatus; and transmitting the ultrasound image data to the ultrasound image providing apparatus at the transmission speed.

According to one or more exemplary embodiments, an ultrasound probe includes: an ultrasound transceiver configured to transmit an ultrasound signal to an object and to receive an echo signal; a signal processor configured to process the echo signal to generate ultrasound image data; a controller configured to acquire information about an ultrasound image providing apparatus wirelessly connected to the ultrasound probe and to determine a transmission speed of ultrasound image data about the object, based on the information about the ultrasound image providing apparatus; and a communicator configured to transmit the ultrasound image data to the ultrasound image providing apparatus at the transmission speed.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
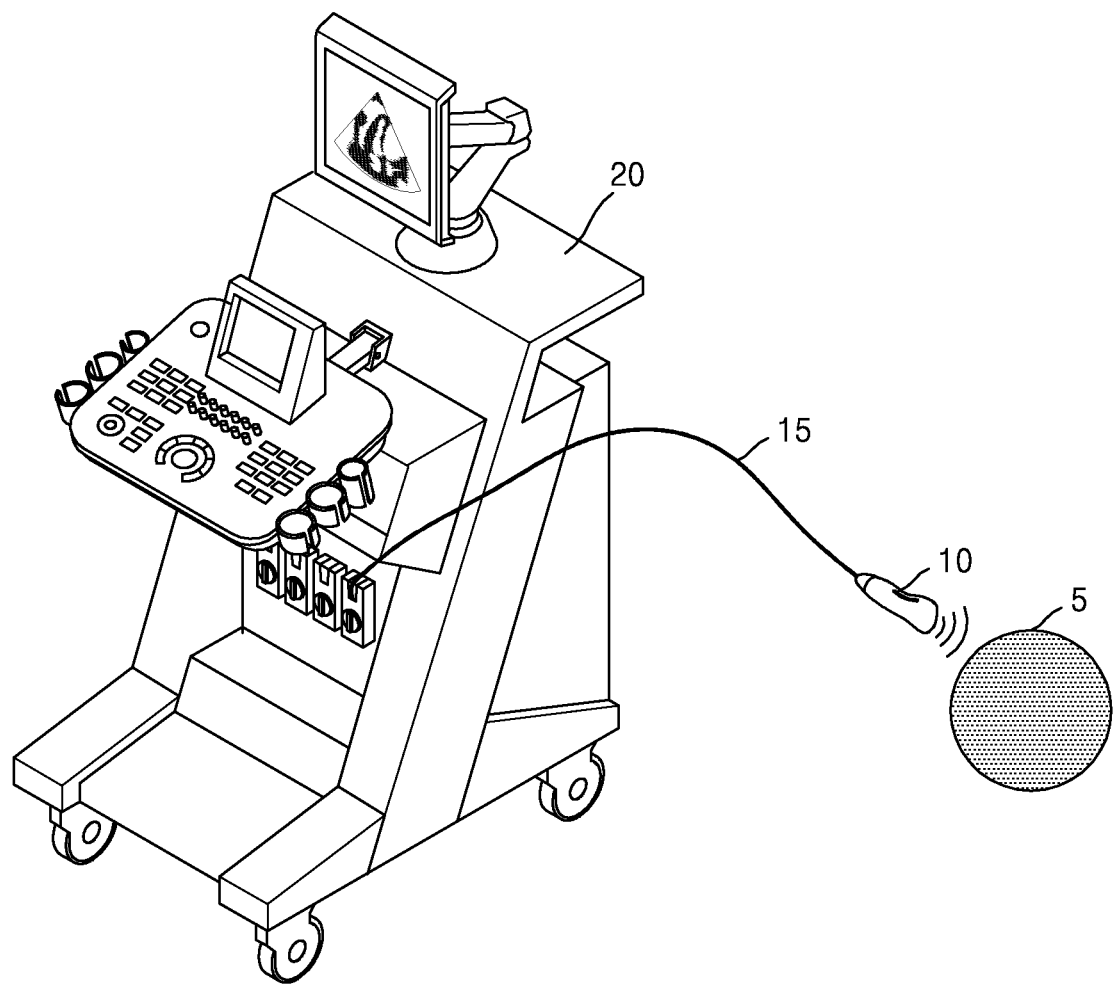
FIG. 1 is a block diagram for describing a general ultrasound system.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

Hereinafter, exemplary embodiments will be described in detail to be easily embodied by those of ordinary skill in the art with reference to the accompanying drawings. The present inventive concept may, however, be embodied in many different forms and should not be construed as being limited to the exemplary embodiments set forth herein. In the accompanying drawings, a portion irrelevant to a description of the present inventive concept will be omitted for clarity. Moreover, like reference numerals refer to like elements throughout.

In this disclosure below, when one part (or element, device, etc.) is referred to as being 'connected' to another part (or element, device, etc.), it should be understood that the former may be 'directly connected' to the latter, or 'electrically connected' to the latter via an intervening part (or element, device, etc.). Furthermore, when it is described that one comprises (or includes or has) some elements, it should be understood that it may comprise (or include or has) only those elements, or it may comprise (or include or have) other elements as well as those elements if there is no specific limitation.

Moreover, each of terms such as " . . . unit", " . . . apparatus" and "module" described in specification denotes an element for performing at least one function or operation, and may be implemented in hardware, software, and/or the combination of hardware and software.

The term "ultrasound image" used herein denotes an image of an object acquired by using an ultrasound wave. The term "object" used herein may include an animate thing or an inanimate thing, which is to be expressed as an image. Also, an object may refer to a part of a human body, and may include an organ such as a liver, a heart, a womb, a brain, breasts, an abdomen, or the like, or a blood vessel.

Moreover, the term "user" used herein may include a medical expert, and may be a doctor, a nurse, a medical technologist, a sonographer, a medical image expert, or the like. However, the user is not limited thereto.

Hereinafter, exemplary embodiments will be described in detail with reference to the accompanying drawings.

FIG. 1 is a block diagram for describing a general ultrasound system.

As illustrated in FIG. 1, the general ultrasound system includes an ultrasound probe 10 and an ultrasound image providing apparatus 20 that is connected to the ultrasound probe 10 by a communication cable 15.

The ultrasound probe 10 transmits an ultrasound signal to an object according to a control signal received from the ultrasound image providing apparatus 20, and receives a response signal (or an ultrasound echo signal) reflected from the object to generate a reception signal. The ultrasound probe 10 focuses the reception signal in order to generate ultrasound image data, and transmits the ultrasound image data to the ultrasound image providing apparatus 20.

The ultrasound image providing apparatus 20 may generate an ultrasound image by using the ultrasound image data received from the ultrasound probe 10, and display the ultrasound image.

A user may experience some difficulty in obtaining an image of the object by using the ultrasound probe 10 of FIG. 1, due to the communication cable 15 that connects the ultrasound probe 10 to the ultrasound image providing apparatus 20, which may cause a manipulability of the ultrasound probe 10 to be degraded.

Moreover, when the ultrasound probe 10 depends on one ultrasound image providing apparatus 20, a plurality of ultrasound probes are provided in proportion to the number of ultrasound image providing apparatuses. This is costly and is difficult to manage. Therefore, it is required to develop a wireless ultrasound probe which does not depend on one diagnostic apparatus, and which is capable of communicating with a plurality of diagnostic apparatuses.

Figure 2:
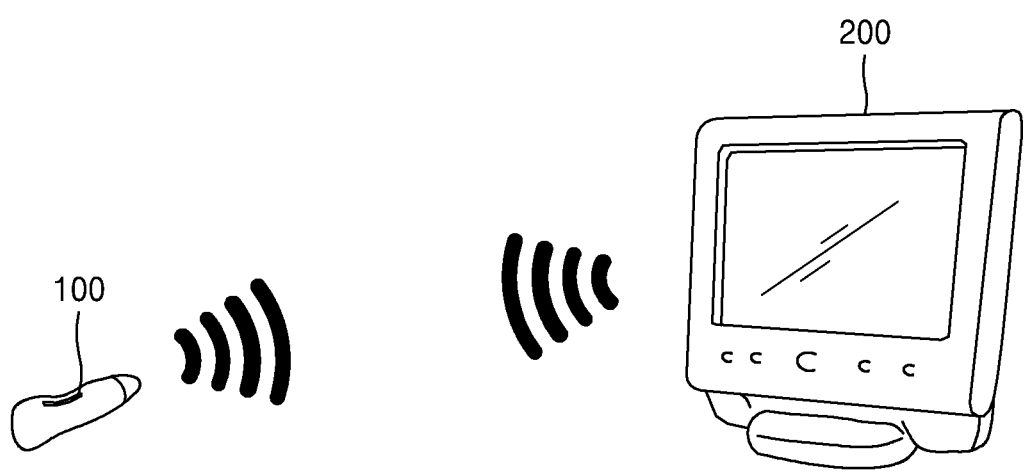
FIG. 2 is a diagram for describing an ultrasound system including an ultrasound probe and an ultrasound image providing apparatus, according to various exemplary embodiments.

FIG. 2 is a diagram for describing an ultrasound system that includes an ultrasound probe and an ultrasound image providing apparatus, according to various exemplary embodiments.

As illustrated in FIG. 2, an ultrasound probe 100 according to various exemplary embodiments may be wirelessly connected to an ultrasound image providing apparatus 200 according to various exemplary embodiments.

The ultrasound probe 100 according to various exemplary embodiments may be wirelessly connected to the ultrasound image providing apparatus 200 via a communication channel. The ultrasound probe 100 may generate ultrasound image data and transmit the generated ultrasound image data to the ultrasound image providing apparatus 200.

In this case, the ultrasound image providing apparatus 200 denotes an apparatus which is connected by wire or wirelessly to the ultrasound probe 100, and provides an ultrasound image to a user by using ultrasound image data received from the ultrasound probe 100.

The ultrasound image providing apparatus 100 may be implemented as a portable type as well as a card type. Examples of portable diagnostic apparatuses may include picture archiving and communication system (PACS) viewers, hand-carried cardiac ultrasound (HCU) equipment, smartphones, laptop computers, personal digital assistants (PDAs), tablet personal computers (PCs), etc., but are not limited thereto.

Moreover, the ultrasound image providing apparatus 200 according to various exemplary embodiments may receive a response signal, which is reflected from an object that has received an ultrasound signal transmitted from the ultrasound probe 100, to generate a reception signal. The ultrasound probe 100 may focus the reception signal according to a control signal received from the ultrasound image providing apparatus 200 to generate ultrasound image data, and transmit the ultrasound image data to the ultrasound image providing apparatus 200.

However, the ultrasound probe 100 according to various exemplary embodiments is not limited to an exemplary embodiment controlled by the ultrasound image providing apparatus 200, and may include a control unit (also referred to herein as a "controller") that controls each element of the ultrasound probe 100 to transmit an ultrasound signal toward an object, receive a response signal reflected from the object, and generate a reception signal. The control unit included in the ultrasound probe 100 may control the ultrasound probe 100 in order for the ultrasound probe 100 to generate ultrasound image data by focusing the reception signal and transmit the ultrasound image data to the ultrasound image providing apparatus 200.

The ultrasound image providing apparatus 200 may be an apparatus that processes ultrasound image data received from the ultrasound probe 100 in order to generate an ultrasound image and displays the generated image, or may be an apparatus that simply performs only an image display function without performing a separate image processing function. In this aspect, the ultrasound image providing apparatus 200 may include a display apparatus that receives an image from the ultrasound probe 100, and displays the received image on a screen without additional processing.

The ultrasound probe 100 according to various exemplary embodiments may transmit ultrasound image data to the ultrasound image providing apparatus 200 at a 60 GHz frequency band. A plurality of transducers included in the ultrasound probe 100 convert the response signal reflected from the object into an electrical signal. A relatively high bandwidth of several gigaHertz (GHz) is needed for wirelessly transmitting the electrical signal which is generated by converting the response signal having sound energy. Also, interference with another wireless electronic device should not occur in transmitting ultrasound image data from the ultrasound probe 100 to the ultrasound image providing apparatus 200.

Therefore, the ultrasound probe 100 according to various exemplary embodiments may transmit the ultrasound image data in a wireless communication scheme using millimeter wave (mmWave) communication. For example, a wireless communication scheme based on WiGig standard of wireless gigabit alliance (WGA) may be used.

However, the ultrasound probe 100 according to various exemplary embodiments is not limited to an exemplary embodiment where ultrasound image data is transmitted to the ultrasound image providing apparatus 200 in a frequency band of 60 GHz. The ultrasound probe 100 may transmit the ultrasound image data to the ultrasound image providing apparatus 200 by using any of various wireless communication schemes (for example, wireless LAN, Wi-Fi, Bluetooth, Zigbee, Wi-Fi direct (WFD), ultra wideband (UWB), infrared data association (IrDA), Bluetooth low energy (BLE), and near field communication (NFC).

The ultrasound probe 100 according to various exemplary embodiments may transmit ultrasound image data to the ultrasound image providing apparatus 200 by using one wireless communication scheme selected from among a plurality of wireless communication schemes.

The ultrasound probe 100 may transmit state information data of the ultrasound probe 100 and control data about the ultrasound image providing apparatus 200 to the ultrasound image providing apparatus 200 by using a separate communication channel (for example, Bluetooth) which differs from a communication channel using the 60 GHz frequency band at which ultrasound image data is transmitted. Also, the ultrasound image providing apparatus 200 may transmit a control signal to the ultrasound probe 100 by using a separate communication channel which differs from the communication channel using the 60 GHz frequency band at which ultrasound image data is received from the ultrasound probe 100.

The ultrasound probe 100 according to various exemplary embodiments may adjust a quality of ultrasound image data transmitted to the ultrasound image providing apparatus 200. The quality of the ultrasound image data may denote a quality of an ultrasound image which is generated by reconstructing the ultrasound image data. The quality of the ultrasound image data, which is transmitted from the ultrasound probe 100 to the ultrasound image providing apparatus 200 in real time, is enhanced in proportion to the amount of data that constitutes one frame. The frame may denote one of a plurality of still images constituting an ultrasound image.

The ultrasound probe 100 may adjust at least one parameter value that relates to the quality of the ultrasound image data. The ultrasound probe 100 may transmit an ultrasound signal to an object, based on the adjusted parameter value, and receive an echo signal in order to generate the ultrasound image data from the echo signal.

For example, the at least one parameter value associated with the quality of the ultrasound image data may include at least one selected from among the number of scan lines constituting one frame of an ultrasound image, the number of sampling points which are set on the scan lines, and the number of bits which are generated by quantizing data acquired from the sampling points.

Moreover, the ultrasound probe 100 according to various exemplary embodiments may adjust a transmission speed at which the ultrasound image data is transmitted to the ultrasound image providing apparatus 200. A transmission speed of the ultrasound image data may be determined based on at least one selected from among the amount of data and a frame rate of one of a plurality of frames that constitute the ultrasound image, namely, the number of frames which are transmitted per unit time. Alternatively, the transmission speed of the ultrasound image data may denote the amount of data which is transmitted per unit time.

As described above, the ultrasound probe 100, according to various exemplary embodiments, may change at least one selected from among the quality of the ultrasound image data, the transmission speed of the ultrasound image data, and a communication scheme which is used for transmitting ultrasound image data. For example, the ultrasound probe 100 may change at least one selected from among the quality of the ultrasound image data, the transmission speed of the ultrasound image data, and a communication scheme depending on a state of a communication channel. Alternatively, the ultrasound probe 100 may change at least one selected from among the quality of the ultrasound image data, the transmission speed of the ultrasound image data, and a communication scheme, based on a user input. Alternatively, the ultrasound probe 100 may change at least one selected from among the quality of the ultrasound image data, the transmission speed of the ultrasound image data, and a communication scheme based on a characteristic of the ultrasound image providing apparatus 200 which is wirelessly connected to the ultrasound probe 100.

Hereinafter, a method of changing, by the ultrasound probe 100 according to various exemplary embodiments, at least one selected from among the quality of the ultrasound image data, the transmission speed of the ultrasound image data, and a communication scheme depending on a state of a communication channel will be described in detail.

As illustrated in FIG. 1, when the ultrasound probe 10 is connected by wire to the ultrasound image providing apparatus 20, a constant data transmission speed is maintained between the ultrasound probe 10 and the ultrasound image providing apparatus 20. Therefore, a constant frame rate and a constant quality of an image are maintained in transmitting ultrasound image data from the ultrasound probe 10 to the ultrasound image providing apparatus 20.

However, as illustrated in FIG. 2, when the ultrasound probe 100 is wirelessly connected to the ultrasound image providing apparatus 200, a communication channel characteristic between the ultrasound image providing apparatus 200 and the ultrasound probe 100 may be changed by an ambient environment. In particular, a data transmission speed between the ultrasound probe 100 and the ultrasound image providing apparatus 200 may be changed due to a change in a bandwidth of a communication channel via which the ultrasound probe 100 is connected to the ultrasound image providing apparatus 200. Therefore, it may be difficult to maintain a constant frame rate and a constant quality of an image when the ultrasound probe 100 wirelessly transmits ultrasound image data to the ultrasound image providing apparatus 200.

To solve the technical problem described above, one or more exemplary embodiments provide an ultrasound probe and an operating method thereof, which adaptively transmits ultrasound image data depending on a state of a communication channel. Hereinafter, a detailed method of operating the ultrasound probe 100 according to an exemplary embodiment will be described in detail with reference to FIG. 3.

Figure 3:
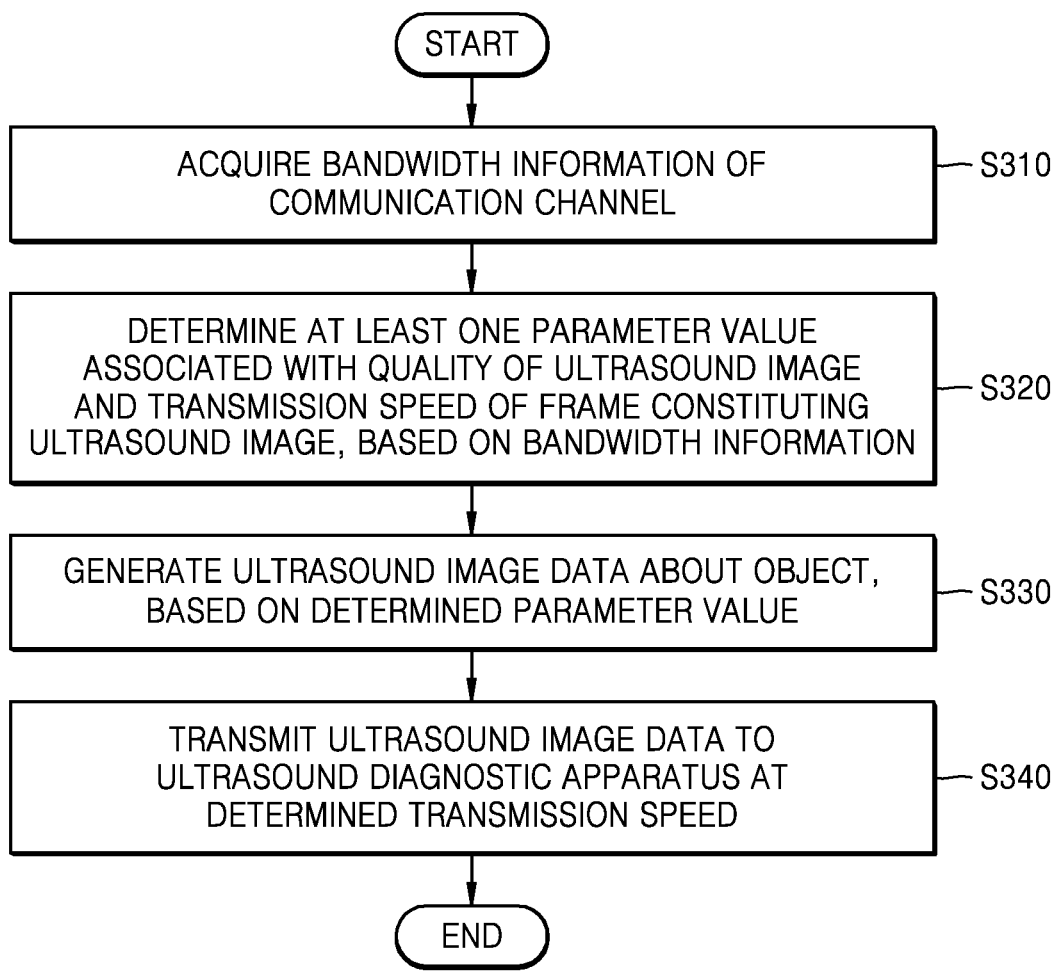
FIG. 3 is a flowchart for describing a method of operating an ultrasound probe which generates and transmits ultrasound image data based on bandwidth information, according to an exemplary embodiment.

FIG. 3 is a flowchart for describing a method of operating an ultrasound probe, according to an exemplary embodiment.

In operation S310, the ultrasound probe 100, according to an exemplary embodiment, may acquire bandwidth information of a communication channel. The ultrasound probe 100 may be wirelessly connected to the ultrasound image providing apparatus 200 via the communication channel.

The communication channel is a communication path for a radio wave, and denotes a frequency band which has previously been allocated for radio wave communication. The ultrasound probe 100 may transmit or receive data to or from the ultrasound image providing apparatus 200 via a certain communication channel. A data transmission rate between the ultrasound probe 100 and the ultrasound image providing apparatus 200 is proportional to a frequency range of a signal which is used for data transmission. Here, the frequency range of the signal used for data transmission is referred to as a bandwidth of a communication channel.

The ultrasound probe 100 may be controlled by a control signal received from the ultrasound image providing apparatus 200 which is connected to the ultrasound probe 100. The ultrasound probe 100 is connectable to a plurality of ultrasound image providing apparatuses, but may be temporarily dependent on the ultrasound image providing apparatus 200 according to a user's motion. Alternatively, the ultrasound probe 100 may be connected to a plurality of ultrasound image providing apparatuses including the ultrasound image providing apparatus 200 via different respective communication channels.

The user's motion may include an operation that contacts the ultrasound probe 100 or places it in close proximity to a diagnostic apparatus 200, selects an ultrasound image providing apparatus, which is to be connected to the ultrasound probe 100, by using the ultrasound probe 100, and/or selects a connection with the ultrasound probe 100 by using the ultrasound image providing apparatus 200.

That the ultrasound probe 100 is temporarily dependent on the ultrasound image providing apparatus 200 may denote that the ultrasound probe 100 is wirelessly connected to the ultrasound image providing apparatus 200, and data is transmittable or receivable. The ultrasound probe 100 being wirelessly connected to the ultrasound image providing apparatus 200 may denote that the ultrasound probe 100 is paired with the ultrasound image providing apparatus 200, and thus, a session is established.

The session may denote a logical connection for communication between the ultrasound image providing apparatus 200 and the ultrasound probe 100. An operation in which the ultrasound image providing apparatus 200 and the ultrasound probe 100 recognize each other by exchanging a message may be performed for establishing the session.

In order to establish a session with the ultrasound image providing apparatus 200, the ultrasound probe 100 may transmit a session establishment request signal to the ultrasound image providing apparatus 200, and receive a session establishment check signal from the ultrasound image providing apparatus 200.

The ultrasound probe 100 may acquire bandwidth information of the communication channel from the ultrasound image providing apparatus 200.

The ultrasound probe 100 may acquire the bandwidth information of the communication channel during the session which is established between the ultrasound image providing apparatus 200 and the ultrasound probe 100. The ultrasound probe 100 may acquire information about the bandwidth of the communication channel in an operation of exchanging a message, used to establish the session, with the ultrasound image providing apparatus 200. For example, the ultrasound probe 100 may extract bandwidth information from the session establishment check signal received from the ultrasound image providing apparatus 200. Alternatively, the ultrasound probe 100 establishes the session with the ultrasound image providing apparatus 200, and then, after a certain time elapses or at certain time intervals, the ultrasound probe 100 may acquire the information about the bandwidth of the communication channel.

The information about the bandwidth of the communication channel, for example, may be a bandwidth value itself of the communication channel, or may include any of information about an operation state of the ultrasound probe 100, information about an operation state of the ultrasound image providing apparatus 200, and a test packet for measuring a bandwidth. The ultrasound probe 100 may receive the test packet from the ultrasound image providing apparatus 200, and analyze the test packet, thereby acquiring the bandwidth information of the communication channel.

Alternatively, the information about the bandwidth of the communication channel may include at least one parameter value, associated with a quality of an ultrasound image, which is determined by the ultrasound image providing apparatus 200 on the basis of the bandwidth of the communication channel, and a transmission speed of a frame constituting the ultrasound image. The ultrasound image providing apparatus 200 may transmit the information about the bandwidth of the communication channel to the ultrasound probe 100 by using a separate communication channel which differs from a communication channel using the 60 GHz frequency band.

In operation S320, the ultrasound probe 100 may determine at least one selected from among at least one parameter value associated with a quality of an ultrasound image and a transmission speed of a frame constituting the ultrasound image, based on the bandwidth information.

The ultrasound probe 100 may determine the bandwidth of the communication channel, based on the bandwidth information which is acquired in operation S310.

For example, the ultrasound probe 100 may receive test data from the ultrasound image providing apparatus 200, and divide (i.e., proportionately reduce) a size of the test data by a time, taken until transmission of the test data is completed, in order to calculate a size of data transmitted per unit time. The ultrasound probe 100 may determine the bandwidth of the communication channel, based on the size of the data transmitted per unit time.

As another example, the ultrasound image providing apparatus 200 may detect a bandwidth value of the communication channel, and transmit the detected bandwidth value to the ultrasound probe 100. The ultrasound probe 100 may extract the bandwidth value of the communication channel from the bandwidth information received from the ultrasound image providing apparatus 200.

The ultrasound probe 100, according to an exemplary embodiment, may determine at least one selected from the at least one parameter value associated with the ultrasound image quality and the transmission speed of the frame constituting the ultrasound image, based on the bandwidth information. For example, the ultrasound probe 100 may determine the at least one parameter value associated with the ultrasound image quality, based on the bandwidth information and determine the transmission speed, based on a predetermined default value or a user input. Alternatively, the ultrasound probe 100 may determine the transmission speed of the frame constituting the ultrasound image, based on the bandwidth information, and determine the at least one parameter value associated with the ultrasound image quality, based on the predetermined default value or the user input.

For example, the at least one parameter value associated with the quality of the ultrasound image may include at least one selected from among the number of scan lines constituting the frame of the ultrasound image, the number of sampling points which are set on a scan line, and the number of bits which are generated by quantizing data which is acquired with respect to a sampling point.

The frame constituting the ultrasound image may correspond to one of a plurality of still images which constitutes a real-time ultrasound image. The transmission speed of the frame constituting the ultrasound image may correspond to the number of frames transmitted per unit time.

For example, the ultrasound probe 100 according an exemplary embodiment may compare a reference bandwidth with the bandwidth of the communication channel between the ultrasound probe 100 and the ultrasound image providing apparatus 200, and determine at least one selected from among the at least one parameter value associated with the quality of the ultrasound image and the transmission speed of the frame constituting the ultrasound image, based on a result of the comparison. The reference bandwidth may be a predetermined value or a value which is set by a user. Alternatively, the ultrasound probe 100 may determine a previously measured bandwidth as the reference bandwidth, and whenever a bandwidth is changed, the ultrasound probe 100 may determine at least one of the at least one parameter value associated with the quality of the ultrasound image and the transmission speed of the frame constituting the ultrasound image.

For example, when the bandwidth of the communication channel becomes narrower than the reference bandwidth, the ultrasound probe 100 may lower the transmission speed of the frame, based on a reduction amount (i.e., an amount of the narrowing) of the bandwidth.

As another example, when the bandwidth of the communication channel is narrowed, the ultrasound probe 100 may decrease at least one selected from the number of scan lines constituting the frame of the ultrasound image, the number of sampling points which are set on a scan line, and the number of bits which are generated by quantizing data which is acquired with respect to a sampling point, based on a reduction amount of the bandwidth.

The ultrasound probe 100 may predetermine and store at least one parameter value associated with ultrasound image quality and a transmission speed of a frame constituting an ultrasound image, based on the bandwidth of the communication channel. The ultrasound probe 100 may map an experimentally optimized parameter value and a transmission speed of a frame to each of a plurality of bandwidths, and store the mapped parameter value and transmission speed. The ultrasound probe 100 may measure the bandwidth of the communication channel, search for pre-stored data on the basis of the measured bandwidth of the communication channel, and determine at least one parameter value and a transmission speed of a frame constituting an ultrasound image, which are searched from the data, as a parameter and a transmission speed which are suitable for the measured bandwidth of the communication channel.

Moreover, the ultrasound probe 100 according to an exemplary embodiment may determine whether to change a quality of an ultrasound image or whether to change a transmission speed of a frame, based on a bandwidth change of the communication channel. Which of the quality of the ultrasound image and the transmission speed of the frame is more important may be selected according to an application, or may be selected by a user.

For example, when the ultrasound probe 100 operates in an image mode (for example, a brightness (B) mode) in a situation in which a quality of an ultrasound image is important for a diagnosis of a disease, the ultrasound probe 100 maintains the quality of the ultrasound image despite a change in the bandwidth of the communication channel. Therefore, when the ultrasound probe 100 operates in the image mode where a quality of an ultrasound image is important, the ultrasound probe 100 maintains the quality of the ultrasound image by changing only a transmission speed of a frame, based on the change in the bandwidth of the communication channel.

Conversely, when the ultrasound probe 100 operates in an image mode (for example, a Doppler mode or an elastic mode) in a situation in which it is more important to maintain a transmission speed of a frame, instead of maintaining the quality of an ultrasound image, for a diagnosis of a disease, the ultrasound probe 100 maintains a constant frame transmission speed despite a change in the bandwidth of the communication channel. Therefore, the ultrasound probe 100 maintains the transmission speed of the frame by changing only a parameter value associated with the quality of the ultrasound image, based on the change in the bandwidth of the communication channel.

The ultrasound probe 100, according to an exemplary embodiment, may determine which of a quality of an ultrasound image and a transmission speed of a frame is more important, based on an application used by the ultrasound probe 100.

The application may include all application software which is used for the ultrasound probe 100 in order to acquire ultrasound image data, and is used for the ultrasound image providing apparatus 200 in order to process the ultrasound image data.

For example, the ultrasound probe 100 may use different applications, based on a diagnosed part from which ultrasound image data is acquired or a diagnosis division which uses the acquired ultrasound image data. For example, the diagnosis division may include any of obstetrics (OB), gynecology (GYN), pediatrics (PD), chest surgery (CS), radiology (RD), neurosurgery (NS), and abdomen.

Alternatively, the ultrasound probe 100 may use different applications, based on a mode of an ultrasound image which is to be generated from ultrasound image data. For example, the mode of the ultrasound image may include any of an amplitude (A) mode, a B mode, a motion (M) mode, and a Doppler mode.

The ultrasound probe 100 may automatically or manually select a certain application from among a plurality of applications, based on one selected from a diagnosis division, a diagnosed part, and an image mode, and may use the selected application.

The ultrasound probe 100 may determine which of a quality of an ultrasound image and a transmission speed of a frame is more important, based on the selected application.

The ultrasound probe 100 may map one of first and second modes to each of a plurality of applications, and store the mapped mode. In particular, the first mode may be a mode in which a transmission speed of a frame is relatively more important, and the second mode may be a mode in which a quality of an ultrasound image is relatively more important.

The ultrasound probe 100 may select a mode which is stored to be mapped to a corresponding application, based on an application used by the ultrasound probe 100.

The ultrasound probe 100 may select one mode from among the first and second modes, based on the application used by the ultrasound probe 100. When the first mode is selected, the ultrasound probe 100 may adjust at least one parameter value associated with a quality of an ultrasound image, based on a change in the bandwidth of the communication channel. When the second mode is selected, the ultrasound probe 100 may adjust a transmission speed of a frame, based on the change in the bandwidth of the communication channel.

For example, when the ultrasound probe 100 uses an application in a circumstance in which it is more important to maintain a transmission speed of a frame, instead of maintaining the quality of an ultrasound image, for a diagnosis of a disease (for example, when an application for scanning a heart image having a lot of movements is used), the ultrasound probe 100 maintains a constant frame transmission speed by adjusting the quality of the ultrasound image, based on a change in the bandwidth of the communication channel.

Alternatively, when the ultrasound probe 100 uses an application in a circumstance in which it is more important to maintain a quality of an ultrasound image, instead of maintaining the transmission speed of a frame, for a diagnosis of a disease (for example, when an application for scanning an abdomen image having few movements is used), the ultrasound probe 100 maintains the quality of the ultrasound image by adjusting the transmission speed of the frame, based on the change in the bandwidth of the communication channel.

Alternatively, the ultrasound probe 100 may determine which of a quality of an ultrasound image and a transmission speed of a frame is more important, based on a user input.

The ultrasound probe 100 may receive a user input about which of the first and second modes the ultrasound probe 100 operates in. The ultrasound probe 100 may select one mode from among the first and second modes, based on the user input.

When the first mode is selected based on a user input (i.e., when a transmission speed of a frame is important), the ultrasound probe 100 may adjust at least one parameter value associated with a quality of an ultrasound image, based on a change in the bandwidth of the communication channel. When the second mode is selected based on a user input (i.e., when a quality of an ultrasound image is important), the ultrasound probe 100 may adjust a transmission speed of a frame, based on the change in the bandwidth of the communication channel.

However, an operation of the ultrasound probe 100 is not limited to the first and second modes. When the bandwidth of the communication channel is changed, the ultrasound probe 100 may adjust at least one of at least one parameter value associated with a quality of an ultrasound image and a transmission speed of a frame constituting the ultrasound image, based on an application or a user input.

The ultrasound image providing apparatus 200 may detect a bandwidth value of the communication channel, and determine at least one parameter value associated with a quality of an ultrasound image and a transmission speed of a frame constituting the ultrasound image, based on the bandwidth value.

The ultrasound image providing apparatus 200 may transmit a control signal, including at least one parameter value associated with a quality of an ultrasound image and a transmission speed of a frame constituting the ultrasound image, to the ultrasound probe 100. The ultrasound image providing apparatus 200 may transmit a control signal to the ultrasound probe 100 by using a separate communication channel which differs from the communication channel using the 60 GHz frequency band.

The ultrasound probe 100 may determine at least one parameter value associated with a quality of an ultrasound image and a transmission speed of a frame constituting the ultrasound image, based on the control signal received from the ultrasound image providing apparatus 200.

In operation S330, the ultrasound probe 100 may generate ultrasound image data about an object, based on the at least one parameter value associated with the ultrasound image quality.

The ultrasound probe 100 may include an ultrasound transmission/reception unit (also referred to herein as an "ultrasound transceiver") 110, which transmits an ultrasound signal toward an object and receives an echo signal, and a signal processing unit (also referred to herein as a "signal processor") 120 that processes the echo signal. The signal processing unit 120 may generate ultrasound image data by using the echo signal. The ultrasound probe 100 according to an exemplary embodiment may control at least one of the ultrasound transmission/reception unit 110 and the control unit 120, based on the at least one parameter value associated with ultrasound image quality.

The ultrasound probe 100 may generate ultrasound image data about the object, based on the parameter value which is determined in operation S320. Alternatively, the ultrasound probe 100 may generate ultrasound image data about the object, based on the parameter value which is predetermined based on a default value or a user input.

Figure 4:
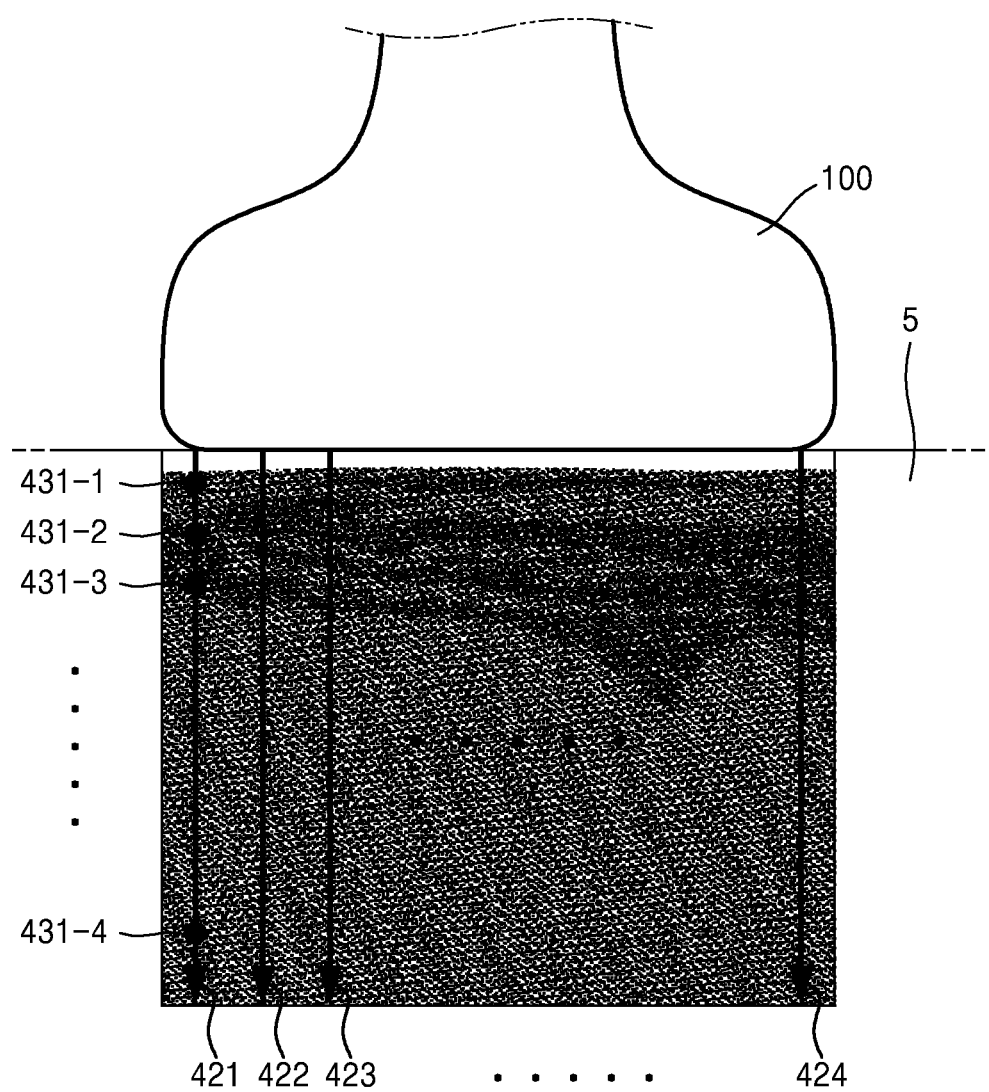
FIG. 4 is a diagram for describing at least one parameter associated with a quality of an ultrasound image, according to various exemplary embodiments.

FIG. 4 is a diagram for describing at least one parameter associated with a quality of an ultrasound image, according to an exemplary embodiment.

As illustrated in FIG. 4, the ultrasound probe 100 may sequentially transmit an ultrasound signal to a plurality of scan lines 421, 422, 423, . . . 424 which are set in an object 5, and acquire ultrasound image data about each of the scan lines 421, 422, 423, . . . 424, based on an echo signal which is received in response to the transmitted ultrasound signal. At this time, the ultrasound probe 100 may acquire data about a plurality of sampling points, which are set on a scan line, from the echo signal, and combine the data about the plurality of sampling points to generate ultrasound image data. For example, as illustrated in FIG. 4, the ultrasound probe 100 may acquire data about a plurality of sampling points 431-1, 431-2, 431-3, . . . 431-4 which are set on a scan line 421, and combine the data about the plurality of sampling points 431-1, 431-2, 431-3, . . . 431-4 to generate ultrasound image data.

The ultrasound probe 100 may adjust at least one selected from among the number of scan lines constituting one frame of an ultrasound image, the number of sampling points which are set on the scan lines, and the number of bits which are generated by quantizing data acquired from the sampling points. The ultrasound probe 100 may adjust the total amount of the generated ultrasound image data by adjusting the at least one parameter value associated with ultrasound image quality.

Moreover, the ultrasound probe 100 may perform additional signal processing on the ultrasound image data, thereby increasing or decreasing the amount of the ultrasound image data.

For example, the ultrasound probe 100 may adjust at least one selected from among the number of scan lines constituting a frame of an ultrasound image, the number of sampling points which are set on a scan line, and the number of bits which are generated by quantizing data which is acquired with respect to a sampling point, based on a change in a bandwidth. The ultrasound probe 100 may adjust at least one parameter value associated with a quality of an ultrasound image in order to adjust a total amount of generated ultrasound image data.

Moreover, the ultrasound probe 100 according to an exemplary embodiment may perform additional signal processing on ultrasound image data on the basis of the bandwidth of the communication channel in order to increase or decrease an amount of the ultrasound image data.

In operation S340, the ultrasound probe 100 according to an exemplary embodiment may transmit the ultrasound image data to the ultrasound image providing apparatus 200 at the determined transmission speed.

The ultrasound image data generated by the ultrasound probe 100 may be used to display an ultrasound image by using the ultrasound image providing apparatus 200.

The ultrasound probe 100 may transmit the ultrasound image data to the ultrasound image providing apparatus 200 at a predetermined transmission speed. For example, the ultrasound probe 100 may transmit the ultrasound image data to the ultrasound image providing apparatus 200 at the transmission speed which is determined in operation S320. Alternatively, the ultrasound probe 100 may generate the ultrasound image data about the object, based on the parameter value which is determined in operation S320. Alternatively, the ultrasound probe 100 may generate ultrasound image data about the object, based on the parameter value which is predetermined based on the default value or the user input.

The ultrasound probe 100 may adjust a transmission speed of a frame constituting an ultrasound image, based on a change in a bandwidth. When the bandwidth of the communication channel is narrowed, the ultrasound probe 100 may lower the transmission speed of the frame constituting the ultrasound image, thereby maintaining the quality of the ultrasound image.

In order to lower a transmission speed of a frame, the ultrasound probe 100 may divide (i.e., reduce an amount of) and transmit data for each frame which is included in ultrasound image data. For example, the ultrasound probe 100 may first transmit data that corresponds to even-numbered scan lines from among a plurality of scan lines constituting a frame of an ultrasound image, and may subsequently transmit data about odd-numbered scan lines, thereby lowering the transmission speed of the frame by half (½, i.e., 50%). However, the exemplary embodiments are not limited thereto, and the ultrasound probe 100 may divide and transmit data for each frame included in ultrasound image data by using any of various schemes.

The ultrasound probe 100 may transmit information about at least one selected from the at least one parameter value and the transmission speed of the frame, which are determined in operation S320, to the ultrasound image providing apparatus 200 in conjunction with the ultrasound image data. Information transmitted to the ultrasound image providing apparatus 200 may be used for the ultrasound image providing apparatus 200 in order to generate an ultrasound image from the ultrasound image data.

The ultrasound probe 100 according to an exemplary embodiment may be connected to a plurality of ultrasound image providing apparatuses via different communication channels. In this case, the ultrasound probe 100 may generate a plurality of transmission streams by processing the ultrasound image data, based on respective characteristics of the plurality of ultrasound image providing apparatuses.

The ultrasound probe 100 may acquire information about a characteristic of the ultrasound image providing apparatus 200 connected to the ultrasound probe 100.

The information about the characteristic of the ultrasound image providing apparatus 200 may include at least one selected from among the kind of data which can be processed by the ultrasound image providing apparatus 200, a wireless communication scheme can be used by the ultrasound image providing apparatus 200, a bandwidth available to the ultrasound image providing apparatus 200, a transmission speed based on a communication channel between the ultrasound image providing apparatus 200 and the ultrasound probe 100, the kind of the communication channel, a version of the ultrasound image providing apparatus 200, a specification of the ultrasound image providing apparatus 200, and an identifier of the ultrasound image providing apparatus 200, but is not limited thereto. The information about the characteristic of the ultrasound image providing apparatus 200 may include, for example, function information of the ultrasound image providing apparatus 200, such as a quality of an ultrasound image capable of being displayed by the ultrasound image providing apparatus 200.

The ultrasound probe 100 may acquire the information about the characteristic of the ultrasound image providing apparatus 200 during a session which is established between the ultrasound image providing apparatus 200 and the ultrasound probe 100. The ultrasound probe 100 may acquire information about the ultrasound image providing apparatus 200 while the ultrasound probe 100 is exchanging a message, which is used to establish the session, with the ultrasound image providing apparatus 200.

The ultrasound probe 100, according to an exemplary embodiment, may acquire respective characteristics of a plurality of ultrasound image providing apparatuses and generate a corresponding plurality of transmission streams by processing the ultrasound image data, based on the acquired characteristics.

The ultrasound probe 100 according to an exemplary embodiment may perform additional signal processing on the ultrasound image data, based on the characteristics of the plurality of ultrasound image providing apparatuses, thereby increasing or decreasing the amount of the ultrasound image data.

The ultrasound probe 100 may generate the plurality of transmission streams by processing the ultrasound image data so that ultrasound images generated from the plurality of ultrasound streams have different respective resolutions, based on corresponding characteristics of communication channels via which a plurality of ultrasound image providing apparatuses are connected to the ultrasound probe 100.

The ultrasound probe 100 according to an exemplary embodiment may transmit each of the plurality of transmission streams to the plurality of ultrasound image providing apparatuses via a corresponding one of the communication channels. The ultrasound probe 100 may transmit pieces of ultrasound image data, having different image qualities, to the plurality of ultrasound image providing apparatuses which are connected to the ultrasound probe 100 through different respective communication channels (i.e., by using different wireless communication schemes).

Details which will be described below with reference to FIG. 24 may be applied to a detailed method of transmitting, the ultrasound probe 100, a plurality of transmission streams to respective ones of a plurality of ultrasound image providing apparatuses. Repetitive descriptions will be omitted.

As described above, when an amount of data capable of being transmitted per unit time is reduced because a characteristic of the communication channel is degraded (i.e., when a bandwidth is reduced), the ultrasound probe 100 according to an exemplary embodiment may reduce at least one parameter value associated with a quality of the ultrasound image, or lower a transmission speed of a frame constituting the ultrasound image.

When a transmission speed of a frame received from the ultrasound probe 100 is lowered or a quality of an ultrasound image generated from received ultrasound image data is degraded, the ultrasound image providing apparatus 200 may perform additional processing on the received ultrasound image data. The ultrasound image providing apparatus 200 may perform the additional processing, thereby preventing a quality of an ultrasound image, provided to a user, from being degraded. For example, the ultrasound image providing apparatus 200 may perform additional processing, such as any of a frame averaging operation, a frame interlacing operation, and an interpolation operation.

Figure 5:
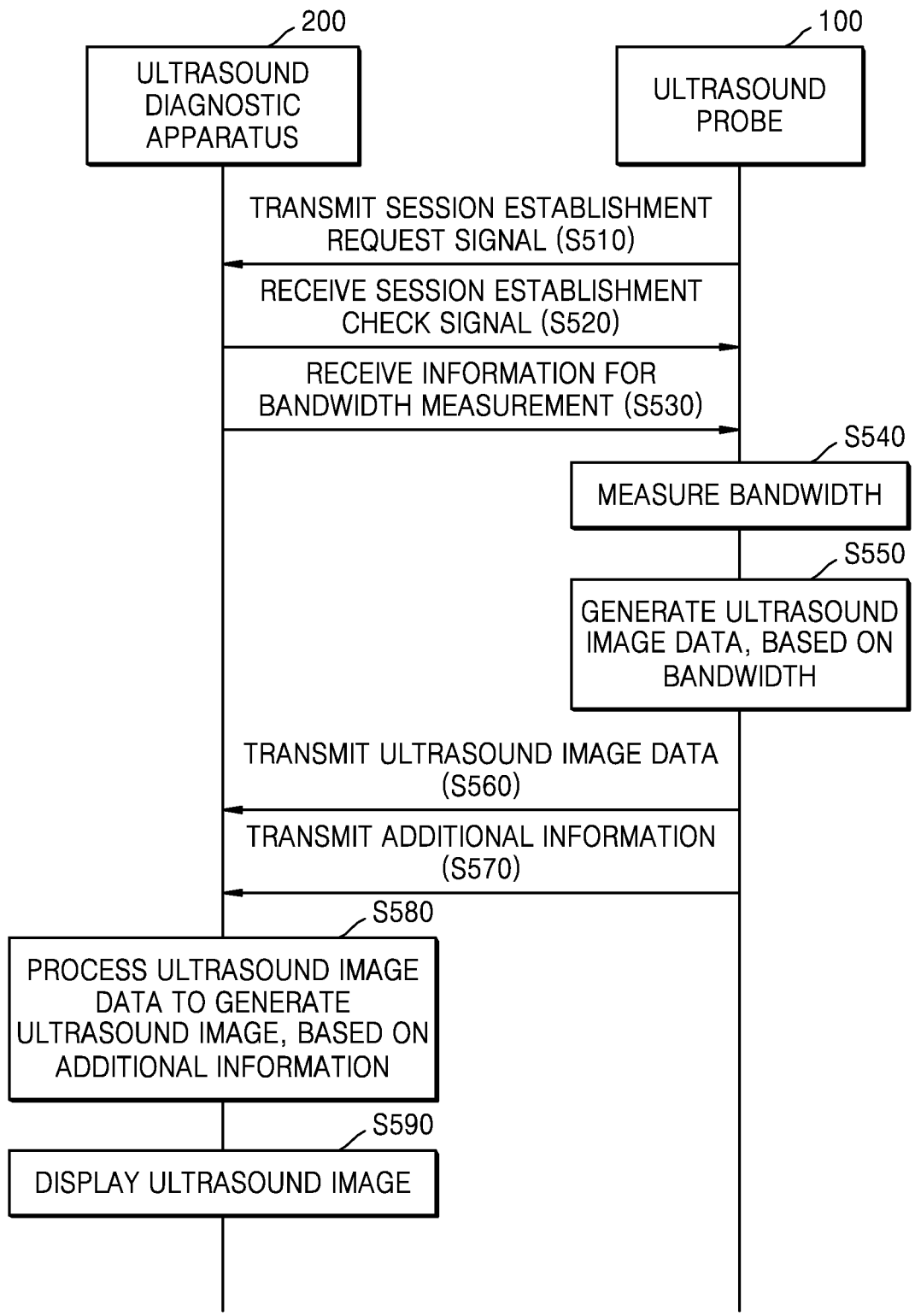
FIG. 5 is a signal flowchart for describing an operation of transmitting ultrasound image data, which is generated based on a bandwidth of a communication channel, from an ultrasound probe to an ultrasound image providing apparatus, according to an exemplary embodiment.

FIG. 5 is a signal flowchart for describing an operation of transmitting ultrasound image data, which is generated based on a bandwidth of a communication channel, from an ultrasound probe to an ultrasound image providing apparatus, according to an exemplary embodiment.

In operation S510, the ultrasound probe 100 according to an exemplary embodiment may transmit a session establishment request signal to the ultrasound image providing apparatus 200, for establishing a session with the ultrasound image providing apparatus 200. The ultrasound image providing apparatus 200 receiving the session establishment request signal may respond to the ultrasound probe 100 that the session establishment request signal has been received. In operation S520, the ultrasound probe 100 may receive a session establishment check signal from the ultrasound image providing apparatus 200.

The ultrasound image providing apparatus 200, which has checked the session establishment request signal from the ultrasound probe 100, may transmit the session establishment check signal and test packets to the ultrasound probe 100 in operation S530.

In operation S540, the ultrasound probe 100 may measure the bandwidth of the communication channel between the ultrasound image providing apparatus 200 and the ultrasound probe 100 in response to the test packets. For example, sizes of the test packets transmitted from the ultrasound image providing apparatus 200 may be previously set to the same size, and moreover, a transmission interval of the test packets may be previously set. The ultrasound probe 100 receiving the test packets may divide a data size of a test packet by the transmission interval of the test packets in order to measure a bandwidth.

In operation S550, the ultrasound probe 100 may generate ultrasound image data, based on the measured bandwidth. In operation S560, the ultrasound probe 100 may transmit the generated ultrasound image data to the ultrasound image providing apparatus 200. At this time, in operation S570, the ultrasound probe 100 may transmit additional information together with the ultrasound image data. The additional information may include information which is usable by the ultrasound image providing apparatus 200 to generate an ultrasound image from the ultrasound image data. For example, the additional information may include a parameter value associated with a quality of an ultrasound image, which is determined based on the bandwidth measured by ultrasound probe 100, or a transmission speed of a frame constituting the ultrasound image.

In operation S580, the ultrasound image providing apparatus 200 may process the ultrasound image data on the basis of the additional information to generate an ultrasound image. The ultrasound image providing apparatus 200 may perform additional processing on the ultrasound image data on the basis of the additional information to generate the ultrasound image. However, the ultrasound image providing apparatus 200 according to an exemplary embodiment is not limited to that the ultrasound image data is processed based on the received additional information. The ultrasound image providing apparatus 200 may actively sense a change in the bandwidth of the communication channel without receiving separate information from the ultrasound probe 100, and may perform additional processing on the ultrasound data, thereby preventing a quality of the ultrasound image from being degraded.

The ultrasound image data received from the ultrasound probe 100 may be data in which an amount of data is reduced based on the bandwidth of the communication channel. In this aspect, when the bandwidth of the communication channel is narrowed and thus a data rate is reduced, the ultrasound probe 100 may transmit ultrasound image data in which a quality of an image is degraded, for maintaining a transmission speed of a frame. The ultrasound image providing apparatus 200 may determine and perform additional processing for enhancing a quality of the received ultrasound image data, based on the additional information. Alternatively, when ultrasound image data in which a transmission speed of a frame is lowered is received, the ultrasound image providing apparatus 200 may perform additional processing on the ultrasound image data so that a disconnection between frames constituting an ultrasound image does not occur.

In operation S590, the ultrasound image providing apparatus 200 may display the generated ultrasound image.

As described above, the ultrasound probe 100 according to an exemplary embodiment may adjust at least one selected from among a quality of ultrasound image data and a transmission speed of the ultrasound image data, based on a state of a communication channel. The ultrasound probe 100 according to an exemplary embodiment may change a transmission speed of a frame, or may change a parameter value associated with the ultrasound image quality, based on a change in a bandwidth of the communication channel. Therefore, even when the state of the communication channel is deteriorated (i.e., when the bandwidth of the communication channel becomes narrower than a reference bandwidth), the ultrasound probe 100 according to an exemplary embodiment may maintain the transmission speed of the frame or the ultrasound image quality.

The ultrasound probe 100 according to an exemplary embodiment may change a communication scheme, which is used to transmit ultrasound image data to the ultrasound image providing apparatus 200, based on a state of a communication channel.

Figure 6:
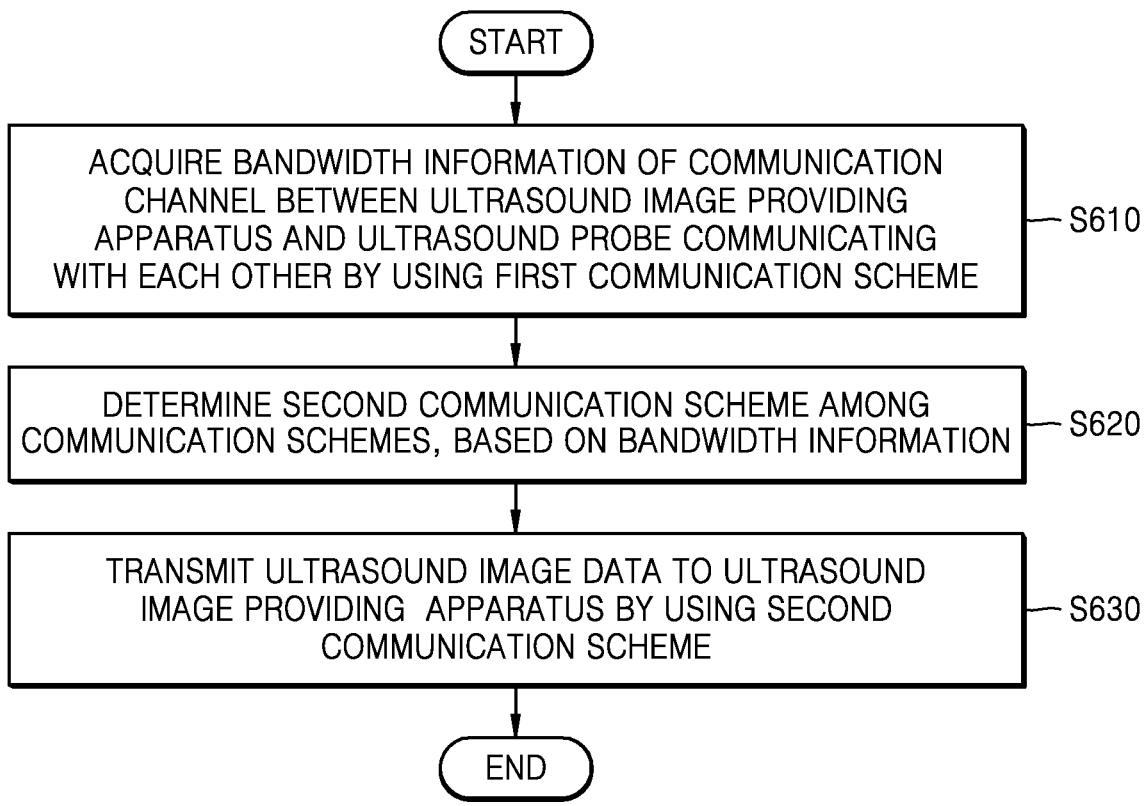
FIG. 6 is a flowchart for describing a method of operating an ultrasound probe which generates and transmits ultrasound image data based on bandwidth information, according to an exemplary embodiment.

FIG. 6 is a flowchart for describing a method of operating an ultrasound probe which determines a communication scheme with the ultrasound image providing apparatus 200 based on bandwidth information, according to an exemplary embodiment.

In operation S610, the ultrasound probe 100, according to an exemplary embodiment, may acquire bandwidth information of a communication channel.

The ultrasound probe 100 may be wirelessly connected to the ultrasound image providing apparatus 200 by using any of a plurality of wireless communication schemes (for example, wireless Gigabit (WiGig), wireless LAN, Wi-Fi, Bluetooth, Zigbee, Wi-Fi direct (WFD), ultra wideband (UWB), infrared data association (IrDA), Bluetooth low energy (BLE), near field communication (NFC), etc.) using various communication channels.

The ultrasound probe 100, according to an exemplary embodiment, may be wirelessly connected to the ultrasound image providing apparatus 200 by using a first communication scheme of the plurality of wireless communication schemes. The ultrasound probe 100 may use the first communication scheme which is predetermined as a default value or is determined based on a user input. The ultrasound probe 100 may acquire bandwidth information that defines a transmission speed of ultrasound image data using the first communication scheme. Operation S610 of FIG. 6 corresponds to operation S310 of FIG. 3, and thus, repetitive descriptions are omitted.

In operation S620, the ultrasound probe 100, according to an exemplary embodiment, may determine a second communication scheme of the plurality of wireless communication schemes, based on the bandwidth information. The ultrasound probe 100 may select one communication scheme from among the plurality of wireless communication schemes used to transmit ultrasound image data to the ultrasound image providing apparatus 200, based on the bandwidth information.

For example, when the transmission speed of the ultrasound image data using the first communication scheme becomes lower than a threshold speed, the ultrasound probe 100 may select the second communication scheme from among the plurality of wireless communication schemes. The ultrasound probe 100 may be wirelessly connected to the ultrasound image providing apparatus 200 by using the second communication scheme.

The ultrasound probe 100 may select the second communication scheme based on priorities allocated to the plurality of wireless communication schemes, or may select the second communication scheme based on bandwidth information of a communication channel used by each of the plurality of wireless communication schemes.

In operation S630, the ultrasound probe 100 according to an exemplary embodiment may transmit the ultrasound image data to the ultrasound image providing apparatus 200 by using the second communication scheme. The ultrasound image data generated by the ultrasound probe 100 may be used for the ultrasound image providing apparatus 200 to display an ultrasound image.

As described above, the ultrasound probe 100 according to an exemplary embodiment may change a communication scheme by which ultrasound image data is transmitted, based on a change in a bandwidth. Therefore, when a communication state of a currently used communication scheme is deteriorated (i.e., when a bandwidth of a communication channel used by the communication scheme is narrowed), the ultrasound probe 100 maintains the smooth transmission of the ultrasound image data by changing the communication scheme.

Figure 7:
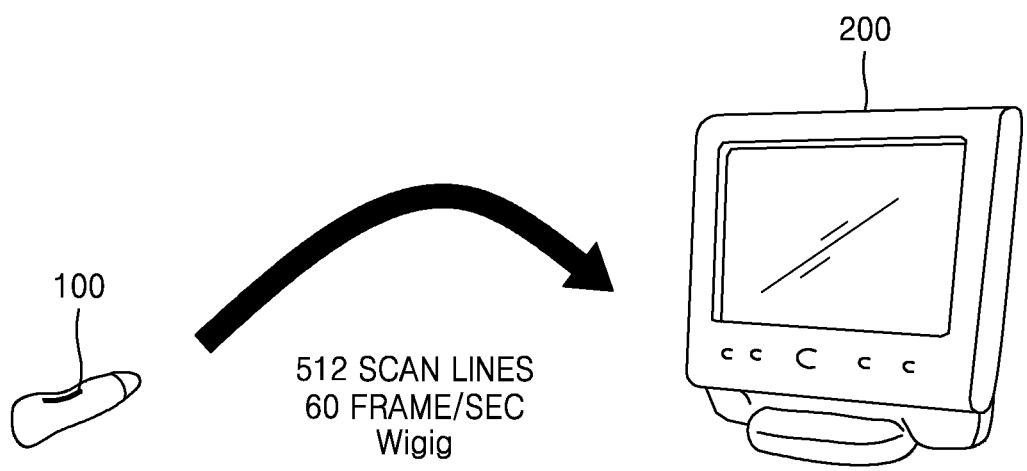
FIGS. 7 and 8 are flowcharts for describing a method of operating an ultrasound probe which transmits ultrasound image data in a communication scheme determined based on bandwidth information, according to an exemplary embodiment.
Figure 8:
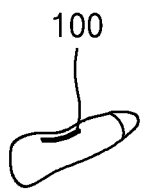
Figure 8:
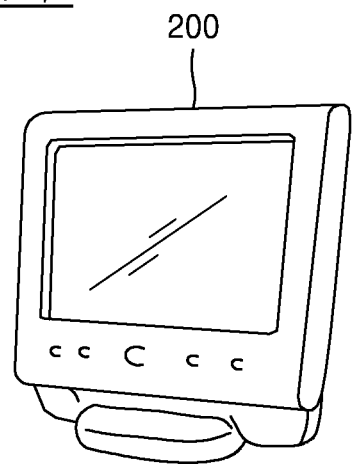
Figure 8:
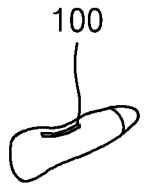
Figure 8:
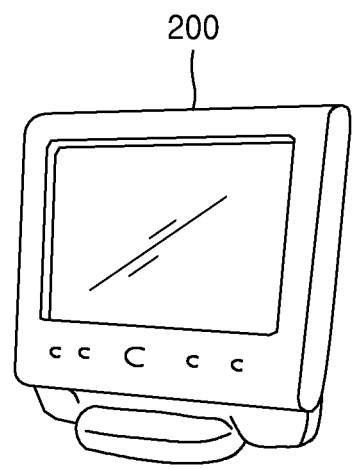
Figure 8:
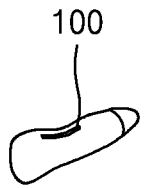
Figure 8:
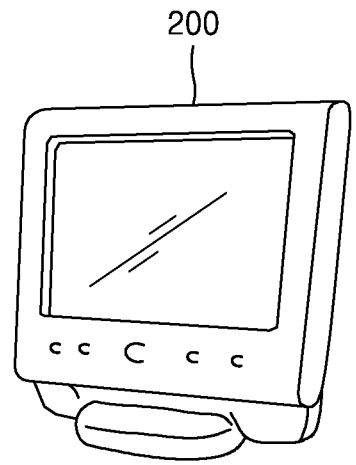

FIGS. 7 and 8 are flowcharts for describing a method of operating an ultrasound probe which transmits ultrasound image data in a communication scheme determined based on bandwidth information, according to an exemplary embodiment.

For example, as illustrated in FIG. 7, the ultrasound probe 100 may transmit an ultrasound signal toward an object and receive an echo signal to generate ultrasound image data which includes frames consisting of 512 scan lines. The ultrasound probe 100 may transmit the ultrasound image data to the ultrasound image providing apparatus 200 at a transmission speed, e.g., a speed at which 60 frames are transmitted per one second, by using WiGig.

As illustrated in FIG. 8, when a bandwidth of a communication channel between the ultrasound probe 100 and the ultrasound image providing apparatus 200 is reduced by ½ (50%), the ultrasound probe 100 according to an exemplary embodiment may change at least one selected from among a quality of ultrasound image data, a transmission speed of the ultrasound image data, and a communication scheme based on a state of the communication channel.

First, as in an image 810, when the bandwidth of the communication channel is reduced by ½, the ultrasound probe 100 may change a parameter value associated with the quality of the ultrasound image data. For example, when the bandwidth of the communication channel is reduced by ½, the ultrasound probe 100 may reduce, by 256, the number of scan lines constituting each of frames of the ultrasound image data and may not change the transmission speed of the ultrasound image data or the communication scheme. Therefore, the ultrasound probe 100 maintains a constant frame transmission speed despite a change in the bandwidth of the communication channel.

The ultrasound probe 100 may operate in an image mode for which the quality of the ultrasound image data being maintained is more important than a transmission speed of a frame of the ultrasound image data being maintained. In this case, as in an image 820, when the bandwidth of the communication channel is reduced by ½, the ultrasound probe 100 may change the transmission speed of the frame of the ultrasound image data. For example, when the bandwidth of the communication channel is reduced by ½, the ultrasound probe 100 may reduce the transmission speed of the frame by 30 frames/second and may not change a parameter associated with the quality of the ultrasound image data or the communication scheme. Therefore, the ultrasound probe 100 maintains the constant quality of the ultrasound image data despite the change in the bandwidth of the communication channel.

Moreover, as in an image 830, when the bandwidth of the communication channel is reduced by ½, the ultrasound probe 100 may change a wireless communication scheme which is used for transmitting the ultrasound image data. For example, when the bandwidth of the communication channel is reduced by ½, by using Wi-Fi instead of WiGig, the ultrasound probe 100 may not change the parameter associated with the quality of the ultrasound image data or the transmission speed of the ultrasound image data. Therefore, the ultrasound probe 100 maintains the smooth transmission of the ultrasound image data despite the change in the bandwidth of the communication channel.

The ultrasound probe 100, according to another exemplary embodiment, may change at least one selected from among the quality of the ultrasound image data, the transmission speed of the ultrasound image data, and the communication scheme, based on a user input. Hereinafter, a method of operating the ultrasound probe 100 according to another exemplary embodiment will be described in detail with reference to FIGS. 9 to 23.

Figure 9:
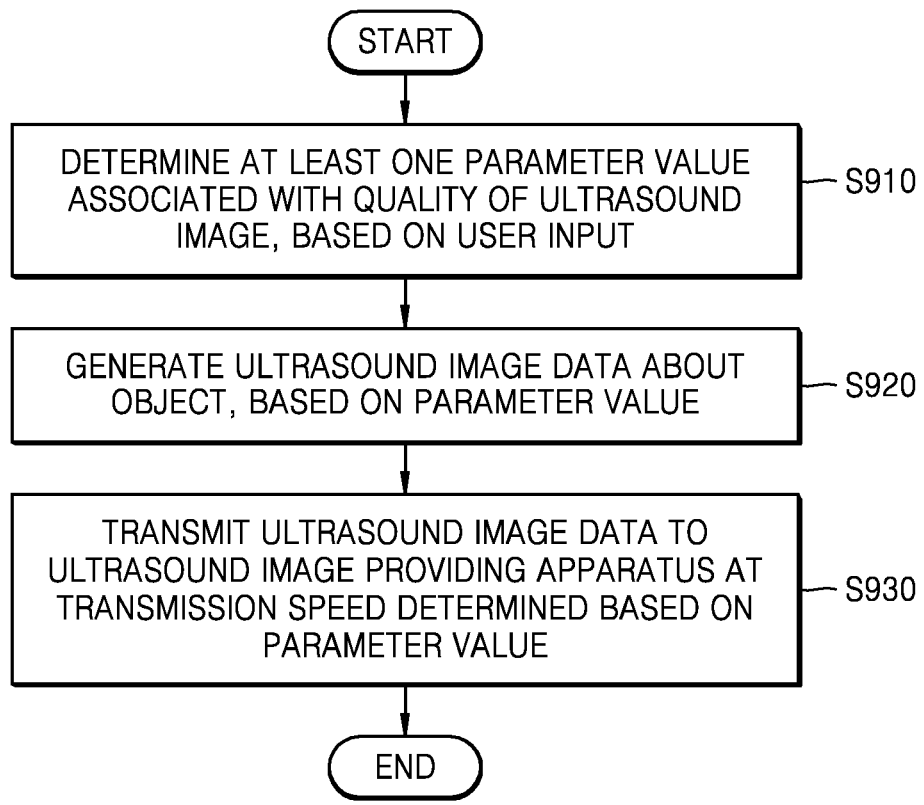
FIG. 9 is a flowchart for describing a method of operating an ultrasound probe which generates and transmits ultrasound image data based on a user input, according to another exemplary embodiment.

FIG. 9 is a flowchart for describing a method of operating an ultrasound probe which generates and transmits ultrasound image data based on a user input, according to another exemplary embodiment.

In operation S910, the ultrasound probe 100 according to another exemplary embodiment may determine at least one parameter value associated with ultrasound image quality, based on a user input.

For example, the user input for determining the at least one parameter value associated with the ultrasound image quality may include any of a parameter value itself or a command for changing the at least one parameter value associated with the ultrasound image quality.

Alternatively, the user input for determining the at least one parameter value associated with the ultrasound image quality may include a user input for determining the quality of the ultrasound image, which is displayed via the ultrasound image providing apparatus 200, as one selected from among high image quality, general image quality, and low image quality. The user input for determining the at least one parameter value associated with the ultrasound image quality may include a user input for determining the quality of the ultrasound image, which is displayed via the ultrasound image providing apparatus 200, as one of a plurality of representative values which are displayed having high image quality, general image quality, or low image quality.

Alternatively, the user input for determining the at least one parameter value associated with the ultrasound image quality may include a user input for selecting an application used by the ultrasound probe 100. The ultrasound probe 100 may map at least one parameter value, associated with a quality of an ultrasound image used by each of a plurality of applications, to each application, and store the mapped parameter value. The ultrasound probe 100 may determine at least one parameter value associated with a quality of an ultrasound image corresponding to the selected application.

The at least one parameter value associated with the quality of the ultrasound image data may include at least one selected from among the number of scan lines constituting one frame of an ultrasound image, the number of sampling points which are set on the scan lines, and the number of bits which are generated by quantizing data acquired from the sampling points.

For example, when a user input for degrading the ultrasound image quality more than a reference image quality is received, the ultrasound probe 100 according to an exemplary embodiment may decrease at least one selected from among the number of scan lines constituting one frame of an ultrasound image, the number of sampling points which are set on the scan lines, and the number of bits which are generated by quantizing data acquired from the sampling points, based on the user input. The reference image quality, a default value, may be a predetermined image quality or an image quality which is set by a user.

For example, the ultrasound probe 100 may include a user input unit (also referred to herein as a "user input device") 160 and may receive, via the user input unit 160, a user input for determining the at least one parameter value associated with the ultrasound image quality.

The ultrasound probe 100 may predetermine and store parameter values associated with the ultrasound image quality according to various user inputs. The ultrasound probe 100 may map an experimentally optimized parameter value to a user input and store the mapped parameter value. When a user input is received, the ultrasound probe 100 may search for pre-stored data, based on the user input, and may acquire the data for at least one parameter value corresponding to the user input.

As another example, the ultrasound probe 100 may receive a user input from the ultrasound image providing apparatus 200. The ultrasound image providing apparatus 200 may receive the user input and transmit a control signal, including information about the user input, to the ultrasound probe 100. The ultrasound probe 100 may determine the at least one parameter value associated with the ultrasound image quality, based on the control signal received from the ultrasound image providing apparatus 200. The ultrasound probe 100 may extract the information about the user input from the received control signal, search for the pre-stored data based on the extracted user input, and acquire the data for the at least one parameter value corresponding to the user input.

As another example, the ultrasound probe 100 may receive, from the ultrasound image providing apparatus 200, information about at least one parameter value associated with ultrasound image quality which is determined based on a user input. The ultrasound image providing apparatus 200 may receive the user input and transmit a control signal, including the information about the at least one parameter value associated with the ultrasound image quality which is determined based on the user input, to the ultrasound probe 100.

The ultrasound image providing apparatus 200 may transmit the control signal to the ultrasound probe 100 by using a communication channel that is different from a communication channel using a frequency band of 60 GHz. The ultrasound probe 100 may determine the at least one parameter value associated with the ultrasound image quality, based on the control signal received from the ultrasound image providing apparatus 200.

Figure 10:
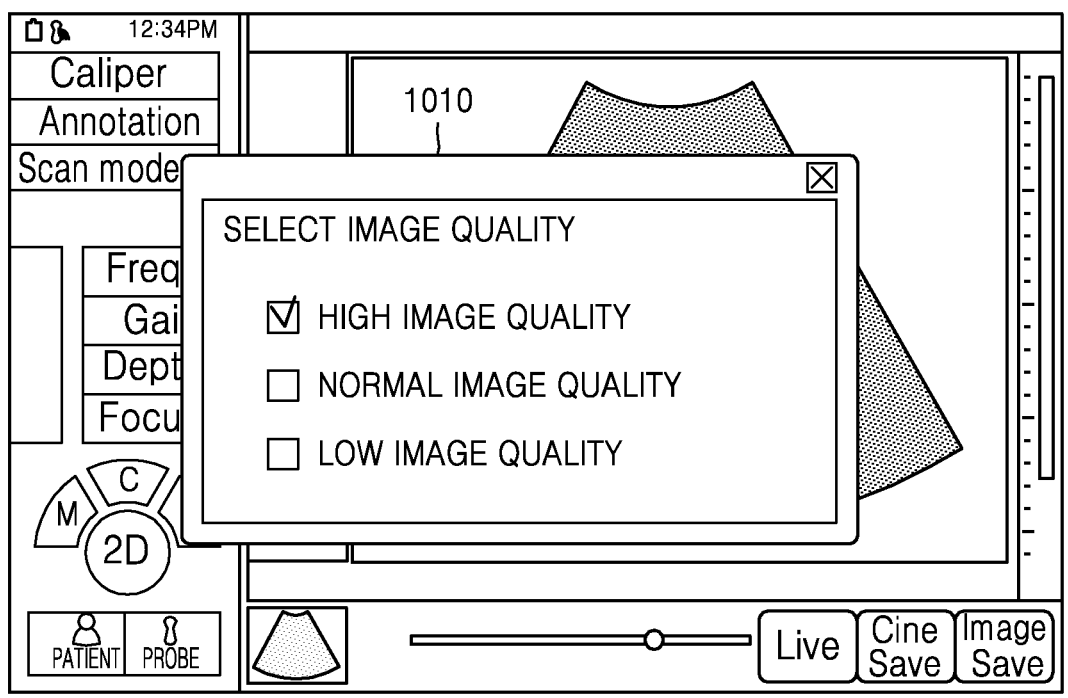
FIGS. 10, 11, and 12 illustrate examples of a user interface display which is configured for receiving a user input that determines a parameter value associated with a quality of an ultrasound image, according to another exemplary embodiment.
Figure 11:
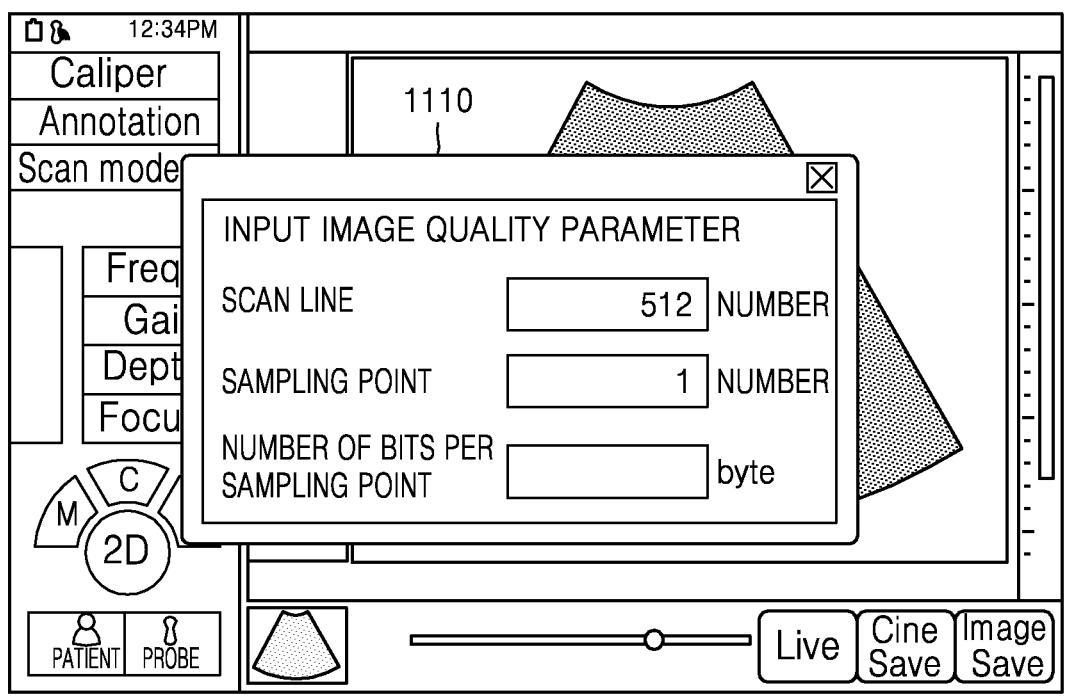
Figure 12:
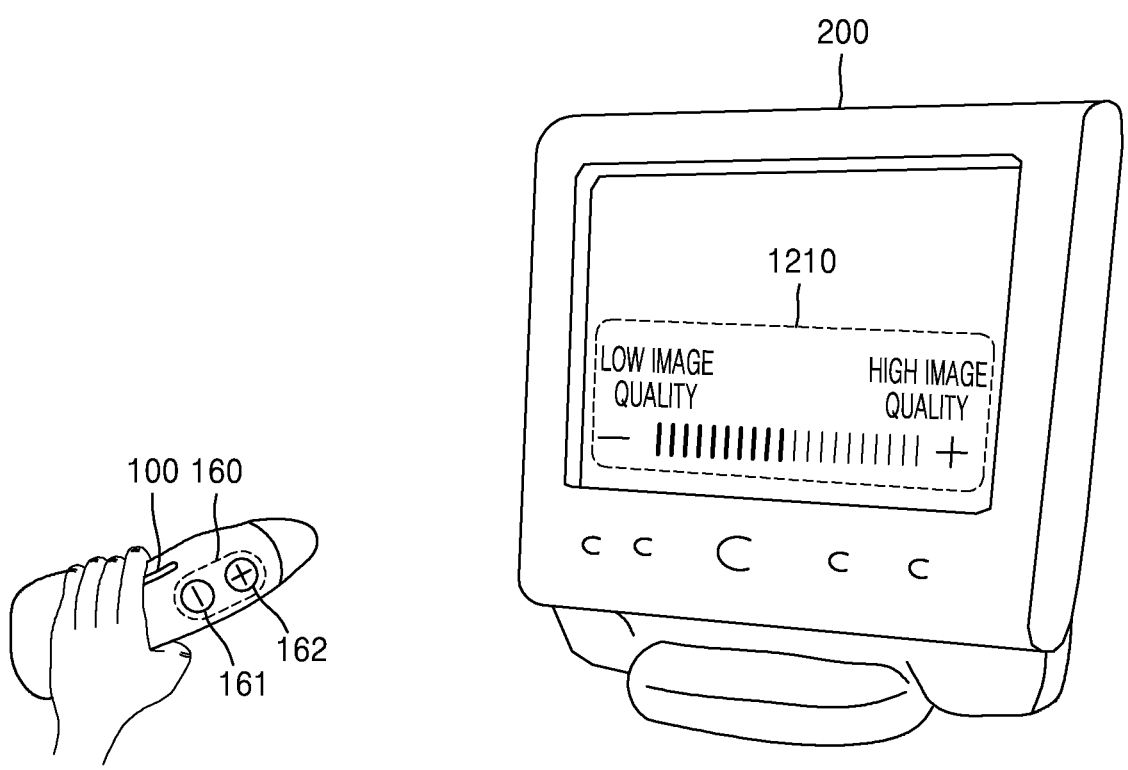

FIGS. 10, 11, and 12 illustrate examples of a user interface display which is configured for receiving a user input that determines a parameter value associated with a quality of an ultrasound image, according to another exemplary embodiment.

As illustrated in FIG. 10, the ultrasound image providing apparatus 200 may display a user interface 1010 for receiving a user input that determines a parameter value associated with a quality of ultrasound image data received from the ultrasound probe 100. A user may select, via the user interface 1010, a quality of the ultrasound image data, to be transmitted by the ultrasound probe 100, as one of high image quality, normal image quality, and low image quality.

The ultrasound probe 100 may extract information about the user input from a control signal received from the ultrasound image providing apparatus 200 and determine at least one parameter value that corresponds to an image quality selected by the user.

Alternatively, as illustrated in FIG. 11, the ultrasound image providing apparatus 200 may display a user interface 1110 for receiving a user input that determines a parameter value associated with a quality of ultrasound image data received from the ultrasound probe 100. A user may input, via the user interface 1110, parameter values associated with the quality of the ultrasound image data to be transmitted by the ultrasound probe 100. For example, the ultrasound image providing apparatus 200 may receive, via the user interface 1110 from the user, the number of scan lines constituting one frame of an ultrasound image, the number of sampling points which are set on the scan lines, and the number of bits which are generated by quantizing data acquired from the sampling points.

The ultrasound probe 100 may extract information about the user input from a control signal received from the ultrasound image providing apparatus 200 and determine at least one parameter value that corresponds to an image quality selected by the user.

Alternatively, as illustrated in FIG. 12, the ultrasound probe 100 may receive, via the user input unit 160, a user input for determining at least one parameter value associated with a quality of an ultrasound image. A user may increase or lower, via the user input unit 160, a quality of ultrasound image data to be received from the ultrasound probe 100.

The ultrasound probe 100 may receive the user input via the user input unit 160 and transmit information about the received user input to the ultrasound image providing apparatus 200. The ultrasound image providing apparatus 200 may display a user interface 1210 that provides information about a quality of ultrasound image data determined by the user, based on the information about the user input received from the ultrasound probe 100.

For example, the ultrasound probe 100 may determine at least one parameter value in order for a quality of ultrasound image data to be lowered, based on a user input that is made by pushing a button 161. When the quality of the ultrasound image data transmitted from the ultrasound probe 100 is lowered, the number of bars representing image quality may be reduced in the user interface 1210. Alternatively, the ultrasound probe 100 may determine at least one parameter value in order for the quality of the ultrasound image data to increase, based on a user input that is made by pushing a button 162. When the quality of the ultrasound image data to be transmitted by the ultrasound probe 100 increases, the number of bars representing image quality may be increased in the user interface 1210.

In operation S920, the ultrasound probe 100 according to another exemplary embodiment may generate ultrasound image data about an object, based on the parameter value which is determined in operation S910.

The ultrasound probe 100 may include an ultrasound transmission/reception unit (also referred to herein as an "ultrasound receiver") 110, which transmits an ultrasound signal to an object and receives an echo signal, and a signal processing unit (also referred to herein as a "signal processor") 120 that processes the echo signal. The signal processing unit 120 may generate ultrasound image data by using the echo signal. Also, the signal processing unit 120 may perform additional signal processing on the ultrasound image data in order to increase or decrease the amount of the ultrasound image data.

The ultrasound probe 100 according to another exemplary embodiment may control at least one of the ultrasound transmission/reception unit 110 and the signal processing unit 120, based on the parameter value which is determined in operation S910. The description of FIG. 4 may be applied to an operation in which the ultrasound probe 100 according to another exemplary embodiment generates the ultrasound image data about the object, based on the parameter value which is determined in operation S910. Repetitive descriptions will be omitted.

The ultrasound probe 100 may control the ultrasound transmission/reception unit 110 based on a user input. For example, the ultrasound probe 100 may adjust the number of scan lines constituting one frame of an ultrasound image or the number of sampling points which are set on the scan lines, based on a user input.

Alternatively, the ultrasound probe 100 may control the signal processing unit 120 based on a user input. For example, based on a user input, the ultrasound probe 100 may adjust the number of bits which are generated by quantizing data acquired from the sampling points, or may perform additional signal processing on pre-acquired ultrasound image data, thereby increasing or decreasing the amount of the ultrasound image data.

In operation S930, the ultrasound probe 100 according to another exemplary embodiment may transmit the ultrasound image data to the ultrasound image providing apparatus 200 at the transmission speed determined based on the parameter value which is determined in operation S910.

For example, when at least one parameter value for degrading the ultrasound image quality (i.e., decreasing the amount of the ultrasound image data) is determined, the ultrasound probe 100 according to another exemplary embodiment may lower a transmission speed of the ultrasound image data according to the determined parameter value. The transmission speed of the ultrasound image data may denote the amount of data which is transmitted per unit time.

For example, the ultrasound probe 100 may determine the transmission speed of the ultrasound image data, based on the parameter value which is determined in operation S910.

The ultrasound probe 100 may predetermine and store transmission speeds of the ultrasound image data, based on parameter values associated with the ultrasound image quality. The ultrasound probe 100 may map an experimentally optimized transmission speed to a parameter value and store the mapped transmission speed and parameter value. When the at least one parameter value associated with the ultrasound image quality is determined in operation S910, the ultrasound probe 100 may search for pre-stored data, based on the determined parameter value, and may determine the data for a transmission speed that corresponds to a predetermined parameter value.

As another example, the ultrasound probe 100 may receive, from the ultrasound image providing apparatus 200, information about the transmission speed of the ultrasound image data determined based on the parameter value which is determined in operation S910.

The ultrasound image providing apparatus 200 may determine a transmission speed of the ultrasound image data, based on the parameter value which is determined in operation S910. The ultrasound image providing apparatus 200 may transmit a control signal, including information about the determined transmission speed, to the ultrasound probe 100. The ultrasound image providing apparatus 200 may transmit the control signal to the ultrasound probe 100 by using a communication channel that is different from a communication channel using a frequency band of 60 GHz. The ultrasound probe 100 may extract the information about the transmission speed of the ultrasound image data from the control signal received from the ultrasound image providing apparatus 200.

The ultrasound probe 100, according to another exemplary embodiment, may determine a parameter value associated with the ultrasound image quality, based on a user input and transmit the ultrasound image data to the ultrasound image providing apparatus 200 at a transmission speed adjusted based on the determined parameter value.

The ultrasound image data generated by the ultrasound probe 100 may be used to display an ultrasound image via the ultrasound image providing apparatus 200.

As described above, the ultrasound probe 100 according to another embodiment may change a transmission speed of ultrasound image data, based on a change in a parameter value associated with a quality of the ultrasound based on a user input.

For example, when the ultrasound probe 100 determines at least one parameter value for degrading a quality of an ultrasound image, the amount of the ultrasound image data may be reduced.

As the amount of ultrasound image data to be transmitted is reduced, the ultrasound probe 100 may reduce the amount of data which is transmitted per unit time, thereby narrowing a bandwidth of a communication channel that connects the ultrasound probe 100 to the ultrasound image providing apparatus 200.

Figure 13:
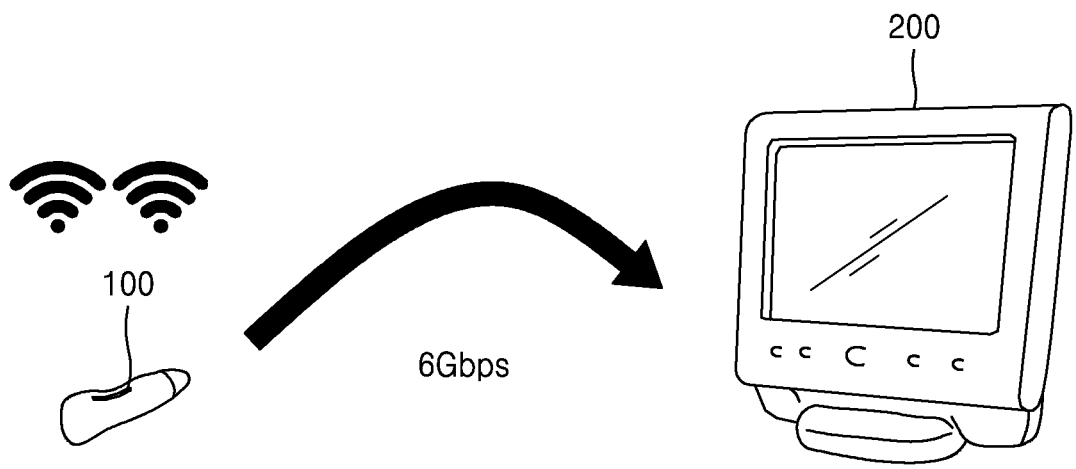
FIG. 13 is a diagram for describing a method of operating an ultrasound probe which generates and transmits ultrasound image data based on a user input, according to another exemplary embodiment.
Figure 13:
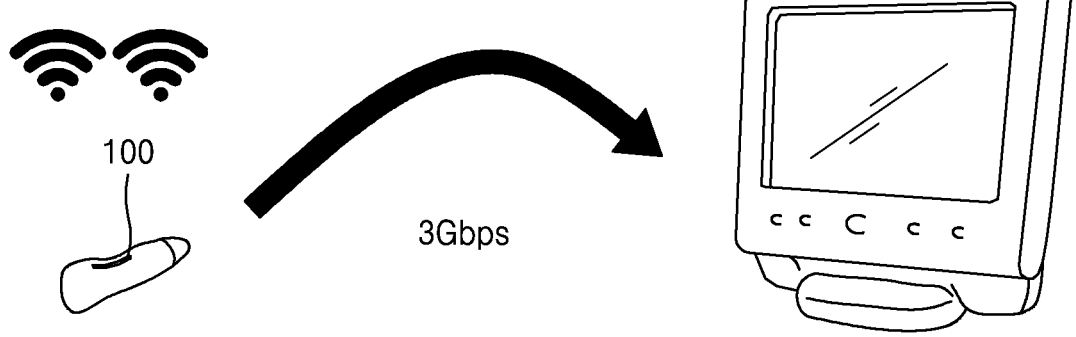

FIG. 13 is a diagram for describing a method of operating an ultrasound probe which generates and transmits ultrasound image data based on a user input, according to another exemplary embodiment.

As in an image 1310, the ultrasound probe 100 may transmit ultrasound image data to the ultrasound image providing apparatus 200 at a transmission speed of 6 Gbps.

An image 1320 shows a method of operating the ultrasound probe 100 according to another exemplary embodiment when a parameter value associated with a quality of ultrasound image data is reduced by ½ based on a user input. As in the image 1320, when the quality of the ultrasound image data is reduced by ½ based on the user input (i.e., when the amount of ultrasound image data to be transmitted by the ultrasound probe 100 is reduced), the ultrasound probe 100 may decrease a transmission speed (i.e., the amount of data which is transmitted per unit time) of the ultrasound image data to 3 Gbps.

When a transmission speed of ultrasound image data transmitted by the ultrasound probe 100 is lowered, the ultrasound probe 100 may decrease an output that wirelessly transmits data, thereby reducing the amount of consumed power. Alternatively, when the transmission speed of the ultrasound image data is lowered, the ultrasound probe 100 that uses a plurality of antennas for wirelessly transmitting data may not use some of the plurality of antennas, thereby reducing the amount of consumed power. Therefore, according to another exemplary embodiment, the ultrasound probe 100 may lower the transmission speed of the ultrasound image data, thereby reducing the amount of power which is consumed when the ultrasound probe 100 transmits data.

In FIGS. 9 to 13, an example in which the ultrasound probe 100 adjusts a quality of ultrasound image data based on a user input is illustrated. However, the ultrasound probe 100 according to another exemplary embodiment is not limited to the example illustrated in FIGS. 9 to 13. For example, as illustrated in FIG. 14, the ultrasound probe 100 according to another exemplary embodiment may adjust a transmission speed of ultrasound image data, based on a user input.

Figure 14:
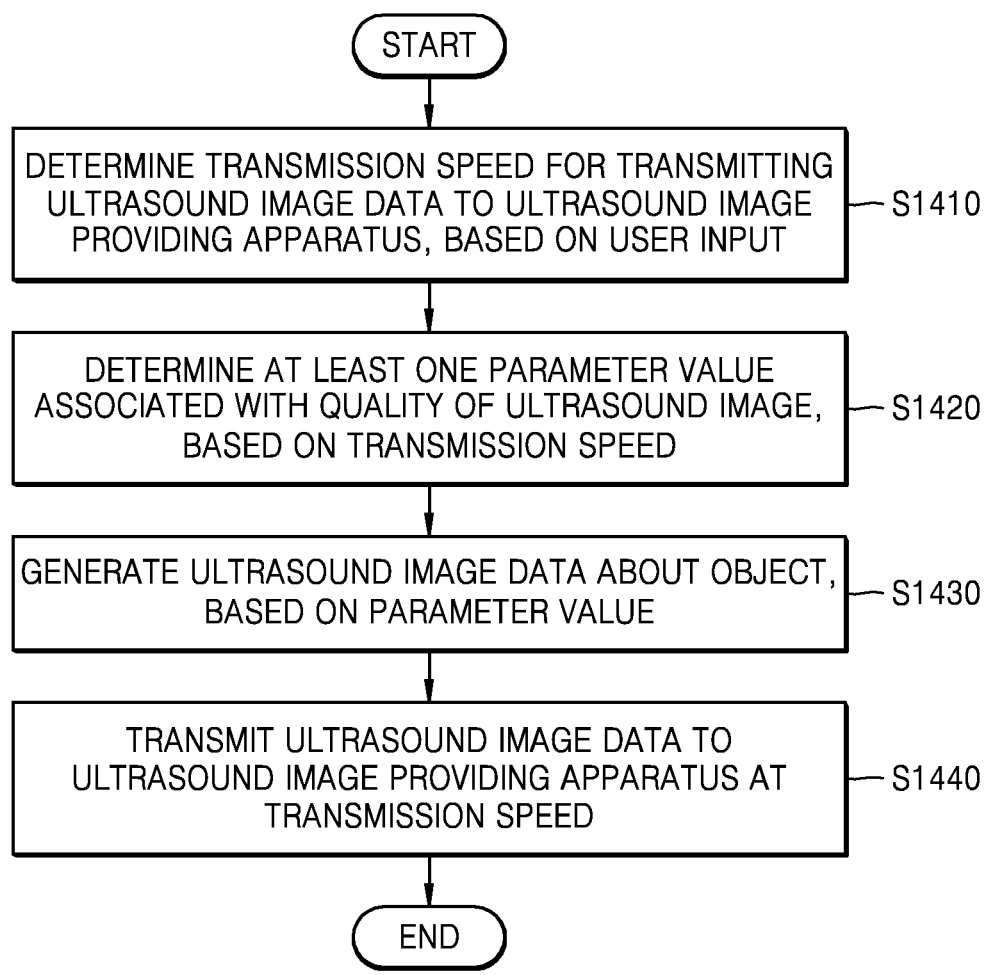
FIG. 14 is a flowchart for describing a method of operating an ultrasound probe which generates and transmits ultrasound image data based on a user input, according to another exemplary embodiment.

FIG. 14 is a flowchart for describing a method of operating an ultrasound probe which generates and transmits ultrasound image data based on a user input, according to another exemplary embodiment.

In operation S1410, the ultrasound probe 100 according to an exemplary embodiment may determine a transmission speed for transmitting ultrasound image data to the ultrasound image providing apparatus 200, based on a user input.

For example, the user input for determining the transmission speed of the ultrasound image data may be a transmission speed value itself of ultrasound image data. Alternatively, the user input for determining the transmission speed of the ultrasound image data may include a user input for determining a transmission speed as at least one selected from among a high speed, a normal speed, and a lower speed.

Alternatively, the user input for determining the transmission speed of the ultrasound image data may include a user input for selecting an application used by the ultrasound probe 100. The ultrasound probe 100 may map each of a plurality of applications to a transmission speed of ultrasound image data used by each application and store the mapped transmission speed. The ultrasound probe 100 may determine a transmission speed of ultrasound image data that corresponds to the selected application.

A transmission speed of the ultrasound image data may be determined based on at least one selected from among the amount of data and a frame rate of one of a plurality of frames constituting the ultrasound image, namely, the number of frames which are transmitted per unit time. Alternatively, the transmission speed of the ultrasound image data may denote the amount of data which is transmitted per unit time.

For example, the ultrasound probe 100 may include a user input unit (also referred to herein as a "user input device") 160 and receive, via the user input unit 160, a user input for determining the transmission speed of the ultrasound image data.

The ultrasound probe 100 may predetermine and store transmission speeds of the ultrasound image data according to various user inputs. The ultrasound probe 100 may map an experimentally optimized transmission speed to a user input and store the mapped transmission speed. When a user input is received, the ultrasound probe 100 may search for pre-stored data, based on the user input and acquire the data for a transmission speed that corresponds to the user input.

As another example, the ultrasound probe 100 may receive a user input from the ultrasound image providing apparatus 200. The ultrasound image providing apparatus 200 may receive the user input and transmit a control signal, including information about the user input, to the ultrasound probe 100. The ultrasound probe 100 may determine the transmission speed of the ultrasound image data, based on the control signal received from the ultrasound image providing apparatus 200. The ultrasound probe 100 may extract the information about the user input from the received control signal, search for the pre-stored data based on the extracted user input, and acquire the data for a transmission speed that corresponds to the user input.

As another example, the ultrasound probe 100 may receive, from the ultrasound image providing apparatus 200, information about a transmission speed of ultrasound image data which is determined based on a user input. The ultrasound image providing apparatus 200 may receive the user input and transmit a control signal, including the information about the transmission speed of the ultrasound image data which is determined based on the user input, to the ultrasound probe 100.

The ultrasound image providing apparatus 200 may transmit the control signal to the ultrasound probe 100 by using a communication channel that is different from a communication channel which uses a frequency band of 60 GHz. The ultrasound probe 100 may determine the transmission speed of the ultrasound image data, based on the control signal received from the ultrasound image providing apparatus 200.

Figure 15:
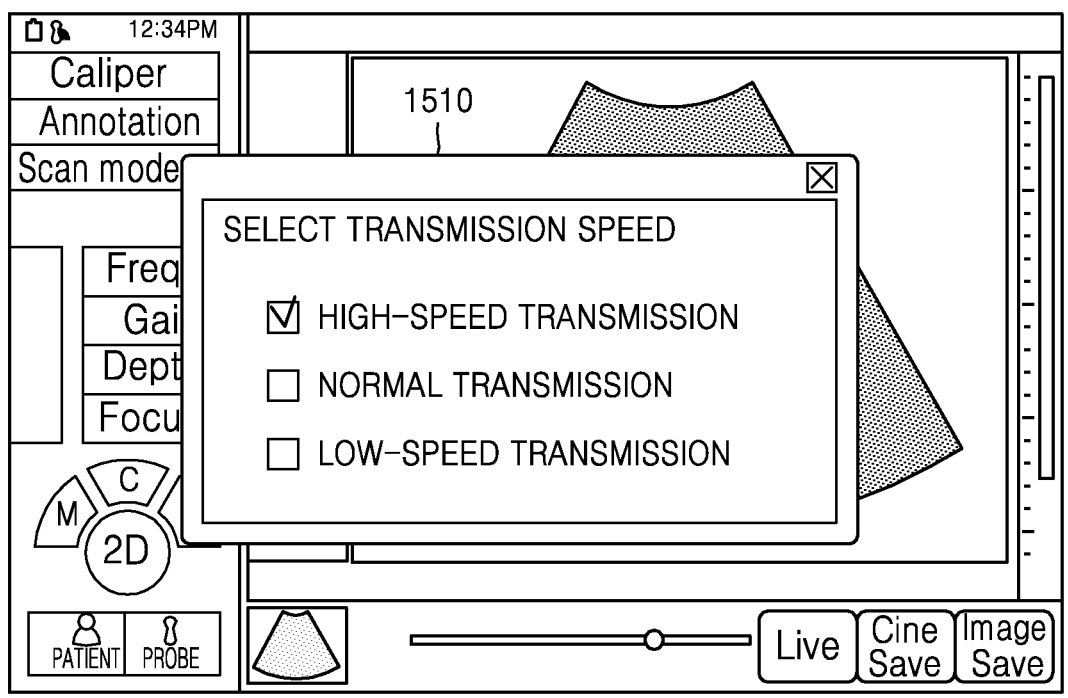
FIGS. 15 and 16 illustrate examples of a user interface display which is configured for receiving a user input that determines a transmission speed at which ultrasound image data is transmitted, according to another exemplary embodiment.
Figure 16:
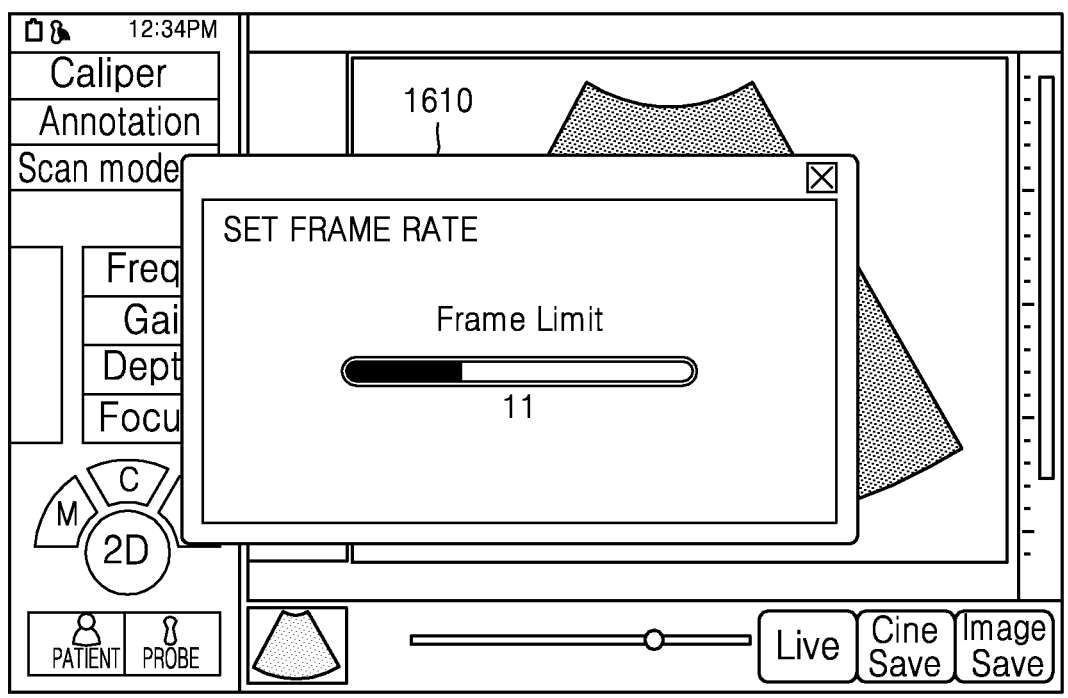

FIGS. 15 and 16 illustrate examples of a user interface display which is configured for receiving a user input that determines a transmission speed at which ultrasound image data is transmitted, according to another exemplary embodiment.

As illustrated in FIG. 15, the ultrasound image providing apparatus 200 may display a user interface 1510 for receiving a user input that determines a transmission speed of ultrasound image data received from the ultrasound probe 100. A user may select, via the user interface 1510, the transmission speed of the ultrasound image data, to be transmitted by the ultrasound probe 100, as one of a high speed, a normal speed, and a low speed.

The ultrasound probe 100 may extract information about a user input from a control signal received from the ultrasound image providing apparatus 200 and determine the transmission speed of the ultrasound image data, based on the user input.

Alternatively, as illustrated in FIG. 16, the ultrasound image providing apparatus 200 may display a user interface 1610 for receiving a user input that determines a transmission speed of ultrasound image data received from the ultrasound probe 100. A user may input, via the user interface 1610, a frame rate of the ultrasound image data to be transmitted by the ultrasound probe 100. The ultrasound probe 100 may acquire information about a transmission speed, determined by the user, from a control signal received from the ultrasound image providing apparatus 200.

In operation S1420, the ultrasound probe 100 according to an exemplary embodiment may determine at least one parameter value associated with ultrasound image quality, based on the transmission speed which is determined in operation S1410.

The at least one parameter value associated with the quality of the ultrasound image data may include at least one selected from among the number of scan lines constituting one frame of an ultrasound image, the number of sampling points which are set on the scan lines, and the number of bits which are generated by quantizing data acquired from the sampling points.

For example, when the transmission speed of the ultrasound image data is lowered, the ultrasound probe 100 according to another exemplary embodiment may decrease at least one selected from among the number of scan lines constituting one frame of an ultrasound image, the number of sampling points which are set on the scan lines, and the number of bits which are generated by quantizing data acquired from the sampling points.

For example, the ultrasound probe 100 may predetermine and store parameter values associated with the ultrasound image quality, based on various transmission speeds. The ultrasound probe 100 may map an experimentally optimized parameter value to a transmission speed and store the mapped transmission speed and parameter value. When the transmission speed is determined in operation S1410, the ultrasound probe 100 may search for pre-stored data, based on the determined transmission speed and acquire the data for at least one parameter value that corresponds to a transmission speed.

As another example, the ultrasound probe 100 may receive, from the ultrasound image providing apparatus 200, information about at least one parameter value associated with the ultrasound image quality, which is determined based on the transmission speed of the ultrasound image data. The ultrasound image providing apparatus 200 may transmit a control signal, including the information about at least one parameter value associated with the ultrasound image quality, which is determined based on the transmission speed of the ultrasound image data, to the ultrasound probe 100. The ultrasound image providing apparatus 200 may transmit the control signal to the ultrasound probe 100 by using a communication channel that is different from a communication channel which uses a frequency band of 60 GHz. The ultrasound probe 100 may determine the at least one parameter value associated with the ultrasound image quality, based on the control signal received from the ultrasound image providing apparatus 200.

In operation S1430, the ultrasound probe 100 according to an exemplary embodiment may generate ultrasound image data about the object, based on the parameter value which is determined in operation S1420.

The ultrasound probe 100 may include an ultrasound transmission/reception unit (also referred to herein as an "ultrasound transceiver") 110, which transmits an ultrasound signal to an object and receives an echo signal, and a signal processing unit (also referred to herein as a "signal processor") 120 that processes the echo signal. The signal processing unit 120 may generate ultrasound image data by using the echo signal. Also, the signal processing unit 120 may perform additional signal processing on the ultrasound image data, based on the user input, thereby increasing or decreasing the amount of the ultrasound image data.

The ultrasound probe 100 according to another exemplary embodiment may control at least one of the ultrasound transmission/reception unit 110 and the signal processing unit 120, based on the parameter value which is determined in operation S1420. The description of FIG. 4 may be applied to an operation in which the ultrasound probe 100 according to another exemplary embodiment generates the ultrasound image data about the object, based on the parameter value which is determined in operation S1420. Repetitive descriptions will be omitted.

The ultrasound probe 100 according to another exemplary embodiment may adjust at least one selected from among the number of scan lines constituting one frame of an ultrasound image, the number of sampling points which are set on the scan lines, and the number of bits which are generated by quantizing data acquired from the sampling points, based on the transmission speed which is determined based on the user input. The ultrasound probe 100 may change the total amount of the generated ultrasound image data by changing the at least one parameter value associated with the ultrasound image quality. Also, the ultrasound probe 100 may perform additional signal processing on the ultrasound image data, based on the user input, thereby increasing or decreasing the amount of the ultrasound image data.

In operation S1440, the ultrasound probe 100 according to another exemplary embodiment may transmit the ultrasound image data to the ultrasound image providing apparatus 200 at the transmission speed which is determined in operation S1410.

The ultrasound probe 100 according to another exemplary embodiment may determine a transmission speed of ultrasound image data, based on a user input, and transmit the ultrasound image data, which is generated from the adjusted parameter value, to the ultrasound image providing apparatus 200 at the determined transmission speed.

The ultrasound image data generated by the ultrasound probe 100 may be used to display an ultrasound image via the ultrasound image providing apparatus 200.

As described above, the ultrasound probe 100 according to another exemplary embodiment may change a parameter value associated with a quality of ultrasound image data, based on a change in a transmission speed of the ultrasound image data which is based on a user input.

For example, as the transmission speed of the ultrasound image data is lowered based on a user input, the amount of data which is transmitted from the ultrasound probe 100 to the ultrasound image providing apparatus 200 per unit time may be reduced. When the transmission speed of the ultrasound image data is lowered based on a user input, the ultrasound probe 100 may determine a parameter value associated with a quality of the ultrasound image data so as to decrease the amount of the ultrasound image data. The ultrasound probe 100 may degrade the quality of the ultrasound image data, based on the determined parameter value.

Figure 17:
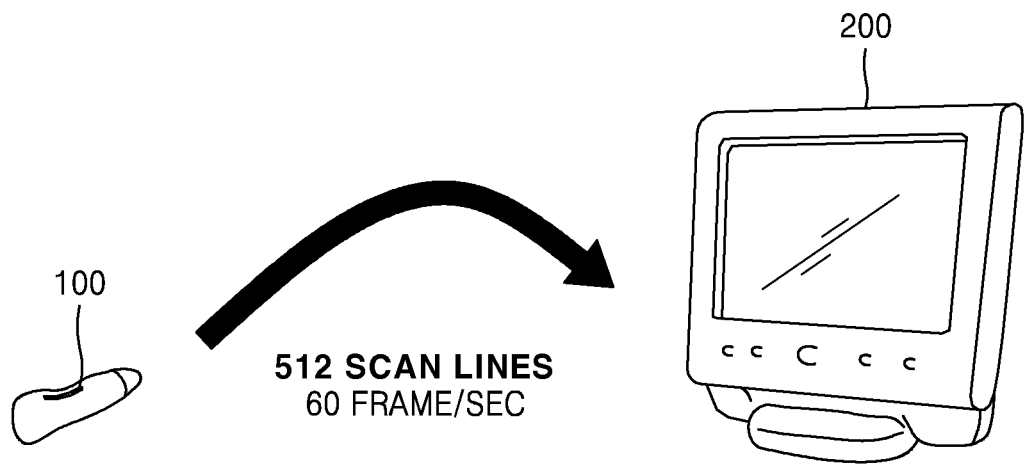
FIG. 17 is a diagram for describing a method of operating an ultrasound probe which generates and transmits ultrasound image data based on a user input, according to another exemplary embodiment.
Figure 17:
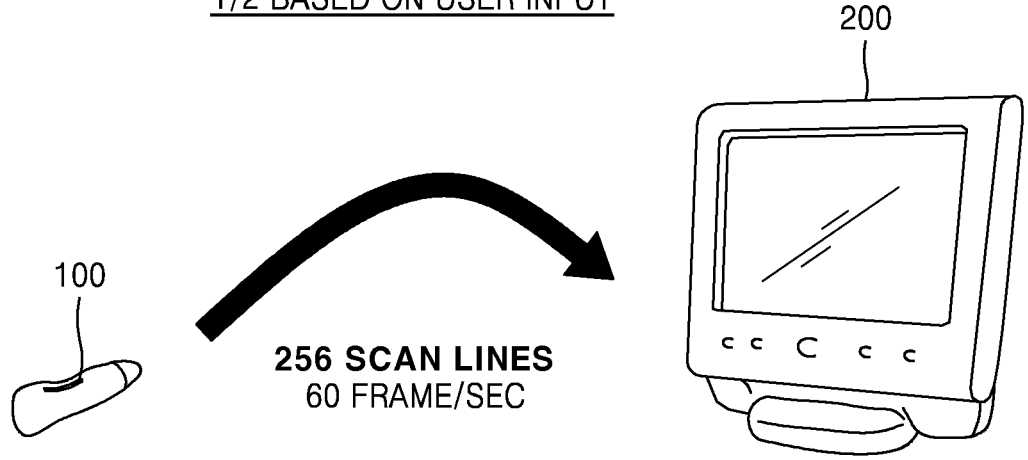

FIG. 17 is a diagram for describing a method of operating an ultrasound probe which generates and transmits ultrasound image data based on a user input, according to another exemplary embodiment.

As in an image 1710, the ultrasound probe 100 may transmit an ultrasound signal toward an object and receive an echo signal to generate ultrasound image data including frames consisting of 512 scan lines. The ultrasound probe 100 may transmit the ultrasound image data to the ultrasound image providing apparatus 200.

An image 1720 shows a method of operating the ultrasound probe 100 according to another exemplary embodiment when a transmission speed of ultrasound image data is reduced by ½ (i.e., 50%) based on a user input. As in the image 1720, when the amount of image data which is transmitted by the ultrasound probe 100 per unit time is reduced by ½ based on a user input, the ultrasound probe 100 may reduce, by 256, the number of scan lines constituting each frame of ultrasound image data.

As the amount of data which is transmitted to the ultrasound image providing apparatus 200 per unit time is reduced, the ultrasound probe 100 according to another exemplary embodiment may degrade a quality of ultrasound image data, thereby maintaining a frame rate of the ultrasound image data.

Therefore, according to another exemplary embodiment, the ultrasound probe 100 may maintain a constant frame rate of ultrasound image data even when the amount of data which is transmitted per unit time is changed based on a user input. In a case of using an application with respect to which it is important to maintain a frame rate (for example, a case of using an application which scans a heart image having a number of motions), the ultrasound probe 100 according to another exemplary embodiment is very useful.

The ultrasound probe 100 according to another exemplary embodiment may be connected to a plurality of ultrasound image providing apparatuses via different respective communication channels. In this case, the ultrasound probe 100 may generate a plurality of transmission streams by processing the ultrasound image data, based on respective characteristics of the plurality of ultrasound image providing apparatuses.

The ultrasound probe 100 according to another exemplary embodiment may acquire the respective characteristics of each of the plurality of ultrasound image providing apparatuses and generate the plurality of transmission streams by processing the ultrasound image data, based on the acquired characteristics.

The ultrasound probe 100 according to another exemplary embodiment may perform additional signal processing on the ultrasound image data, based on the respective characteristics of the plurality of ultrasound image providing apparatuses, thereby increasing or decreasing the amount of the ultrasound image data.

The ultrasound probe 100 may generate the plurality of transmission streams by processing the ultrasound image data so that respective ultrasound images generated from the plurality of ultrasound streams have different resolutions, based on respective characteristics of communication channels via which a plurality of ultrasound image providing apparatuses are connected to the ultrasound probe 100.

The ultrasound probe 100 according to another exemplary embodiment may transmit each of a plurality of transmission streams to a corresponding one of a plurality of ultrasound image providing apparatuses via a corresponding one of a plurality of communication channels. The ultrasound probe 100 may transmit pieces of ultrasound image data having different image qualities to the plurality of ultrasound image providing apparatuses which are connected to the ultrasound probe 100 via different communication channels (i.e., by using different wireless communication schemes), respectively.

Details which will be described below with reference to FIG. 24 may be applied to a detailed method of transmitting, by the ultrasound probe 100, a plurality of transmission streams to corresponding ones of a plurality of ultrasound image providing apparatuses. Repetitive descriptions will be omitted.

Figure 18:
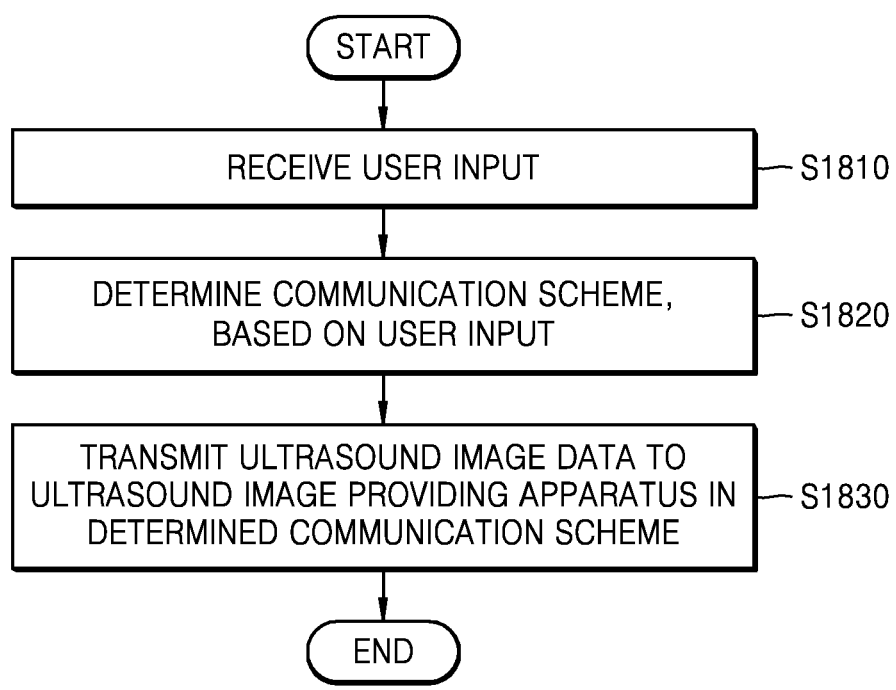
FIG. 18 is a flowchart for describing a method of operating an ultrasound probe which transmits ultrasound image data in a communication scheme determined based on a user input, according to another exemplary embodiment.

FIG. 18 is a flowchart for describing a method of operating an ultrasound probe which transmits ultrasound image data in a communication scheme determined based on a user input, according to another exemplary embodiment.

In operation S1810, the ultrasound probe 100 according to another exemplary embodiment may receive a user input.

The ultrasound probe 100 may include the user input unit 160 and receive, via the user input unit 160, a user input for determining a communication scheme which is used to transmit ultrasound image data.

Alternatively, the ultrasound probe 100 may receive a user input from the ultrasound image providing apparatus 200. The ultrasound image providing apparatus 200 may receive the user input and transmit a control signal, including information about the received user input, to the ultrasound probe 100. The ultrasound probe 100 may receive a user input for determining a communication scheme, which is used to transmit ultrasound image data, from the control signal received from the ultrasound image providing apparatus 200.

Figure 19:
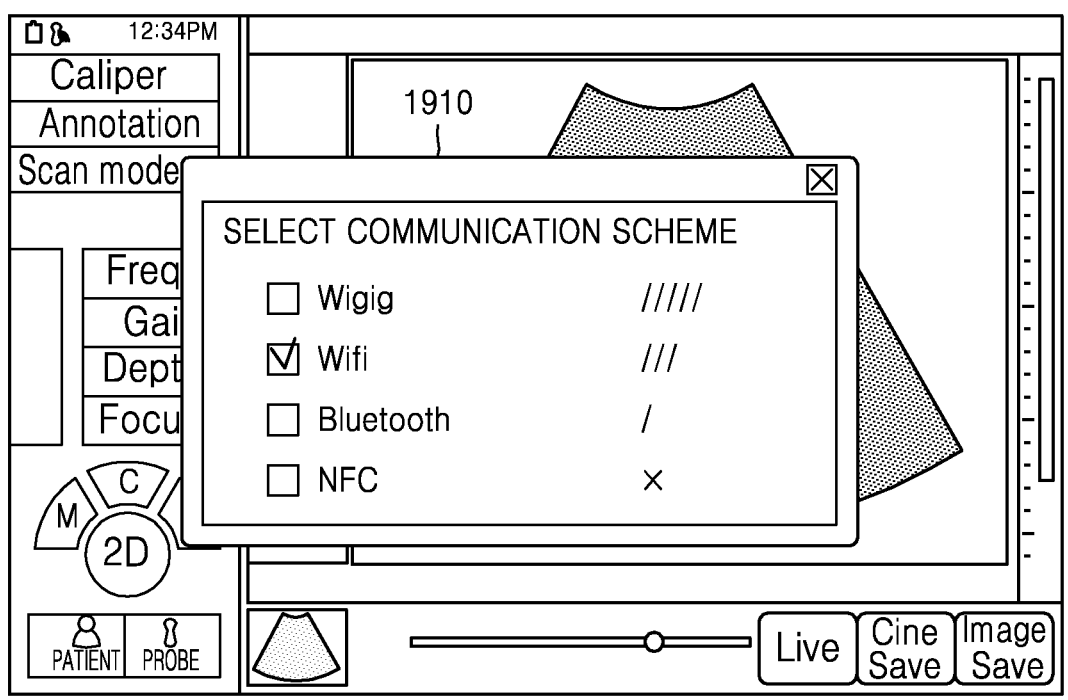
FIG. 19 illustrates an example of a user interface display which is configured for receiving a user input that determines a communication scheme according to which ultrasound image data is transmitted, according to another exemplary embodiment.

FIG. 19 illustrates an example of a user interface displayed for receiving a user input that determines a communication scheme according to which ultrasound image data is transmitted, according to another exemplary embodiment.

As illustrated in FIG. 19, the ultrasound image providing apparatus 200 may display a user interface 1910 for receiving a user input that determines a communication scheme which is used for the ultrasound probe 100 to transmit ultrasound image data.

The user interface 1910 may include a menu within which various communication schemes available to the ultrasound probe 100 are listed or various communication schemes available to the ultrasound image providing apparatus 200 are listed.

The user interface 1910 may display information, indicating whether a corresponding communication scheme is suitable for receiving ultrasound image data from the ultrasound probe 100, as any of a figure, an image, light and shade, a letter, a sign, or a color. For example, as illustrated in FIG. 19, the user interface 1910 may display an intensity of a signal, to be transmitted by the ultrasound probe 100, as the number of rods.

A user may select, via the user interface 1910, a communication scheme, which is used for the ultrasound probe 100 to transmit the ultrasound image data, as one of WiGig, Wi-Fi, Bluetooth, and NFC. The ultrasound probe 100 may extract information about a user input from a control signal received from the ultrasound image providing apparatus 200.

In operation S1820, the ultrasound probe 100 according to another exemplary embodiment may determine a communication scheme, based on the user input.

The ultrasound probe 100 may select one wireless communication scheme from among a plurality of wireless communication schemes supported by the ultrasound probe 100, based on the user input. The ultrasound probe 100 may be wirelessly connected to the ultrasound image providing apparatus 200 by using any of the plurality of wireless communication schemes (for example, wireless Gigabit (WiGig), wireless LAN, Wi-Fi, Bluetooth, Zigbee, Wi-Fi direct (WFD), ultra wideband (UWB), infrared data association (IrDA), Bluetooth low energy (BLE), near field communication (NFC), etc.) using any of various communication channels.

In operation S1830, the ultrasound probe 100 according to another exemplary embodiment may transmit ultrasound image data to the ultrasound image providing apparatus 200 by using the communication scheme which is determined in operation S1820. The ultrasound image data generated by the ultrasound probe 100 may be used by the ultrasound image providing apparatus 200 in order to display an ultrasound image.

As described above, the ultrasound probe 100 according to an exemplary embodiment may transmit the ultrasound image data to the ultrasound image providing apparatus 200 by using a suitable communication scheme which is determined based on the user input. Therefore, the ultrasound probe 100 may seamlessly transmit the ultrasound image data to the ultrasound image providing apparatus 200, thereby providing stable wireless communication.

Figure 20:
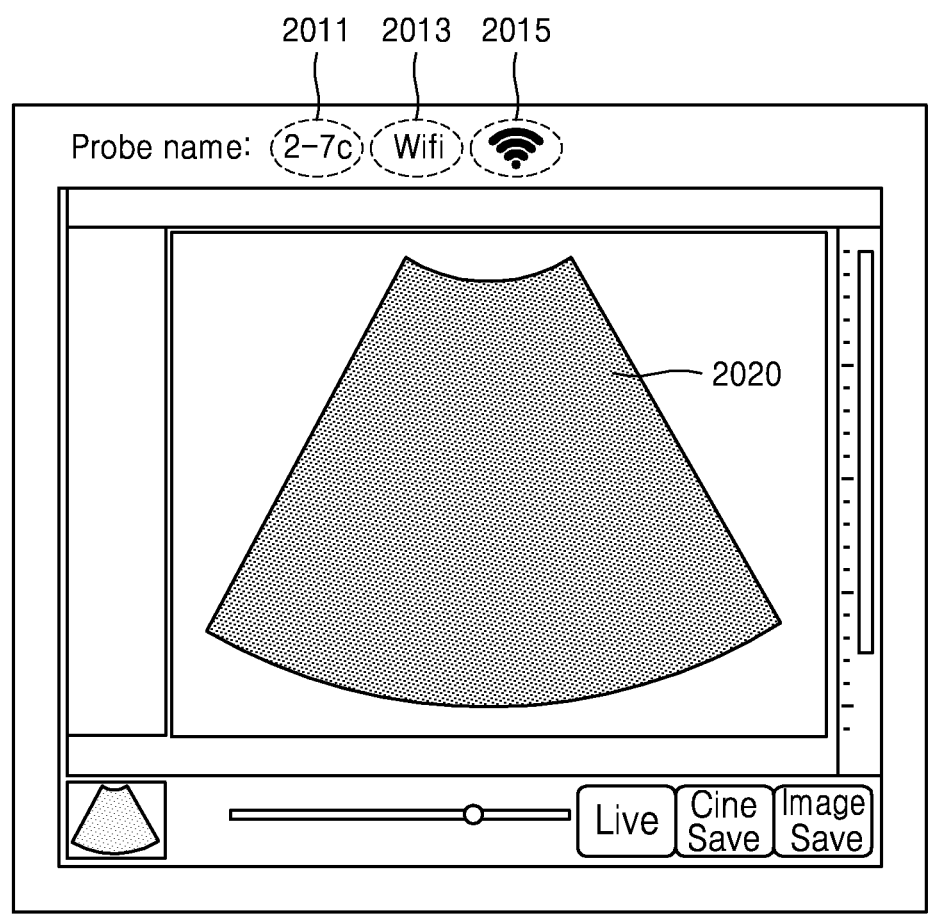
FIG. 20 illustrates an example of a screen for providing information about an ultrasound probe communicating with an ultrasound image providing apparatus, according to various exemplary embodiments.

According to various exemplary embodiments, when the ultrasound probe 100 is wirelessly connected to the ultrasound image providing apparatus 200, the ultrasound image providing apparatus 200 may provide information about the ultrasound probe 100. FIG. 20 illustrates an example of a screen for providing information about an ultrasound probe communicating with an ultrasound image providing apparatus, according to various exemplary embodiments.

As illustrated in FIG. 20, the ultrasound image providing apparatus 200 may receive ultrasound image data from the ultrasound probe 100 and display an ultrasound image 2020 which is generated based on the ultrasound image data. Also, the ultrasound image providing apparatus 200 may display information about an identifier 2011 of the ultrasound probe 100 connected to the ultrasound image providing apparatus 200, a communication scheme 2013 which is used by the ultrasound probe 100 for transmitting the ultrasound image data, and an intensity 2015 of a signal transmitted by the ultrasound probe 100.

The ultrasound probe 100 according to another exemplary embodiment may receive a user input that determines at least one of a quality of ultrasound image data, the amount of data which is transmitted per unit time, a transmission speed of the ultrasound image data, and a communication scheme in consideration of consumption of a battery of the ultrasound probe 100.

Figure 21:
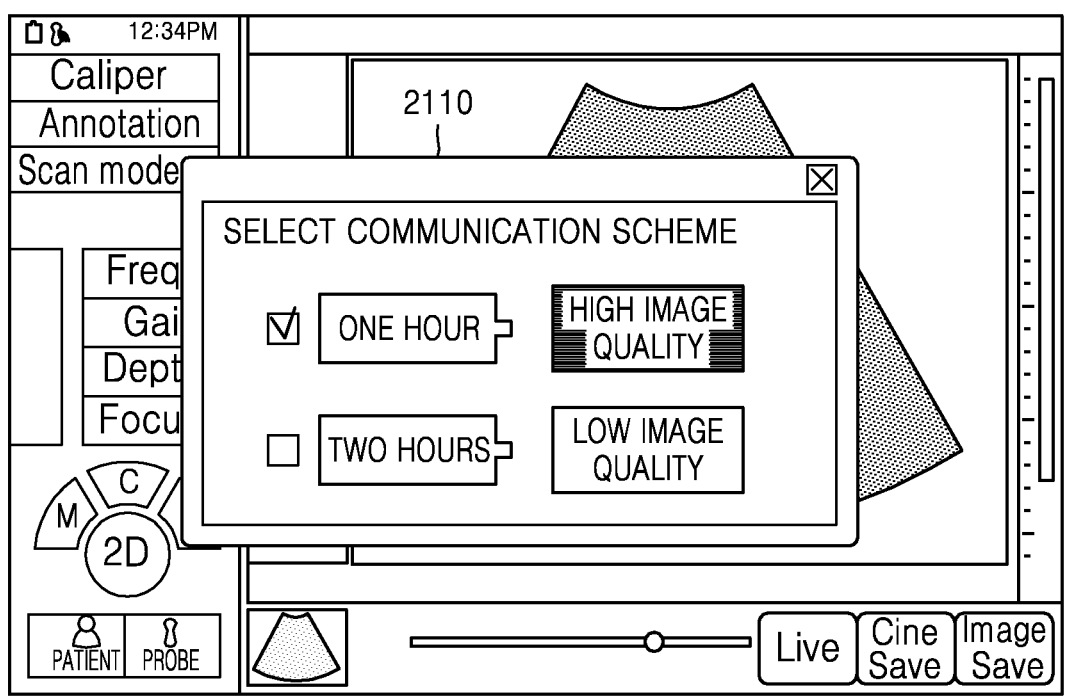
FIG. 21 illustrates an example of a user interface display which is configured for receiving a user input that determines a quality of ultrasound image data in consideration of consumption of a battery of an ultrasound probe, according to another exemplary embodiment.
Figure 22:
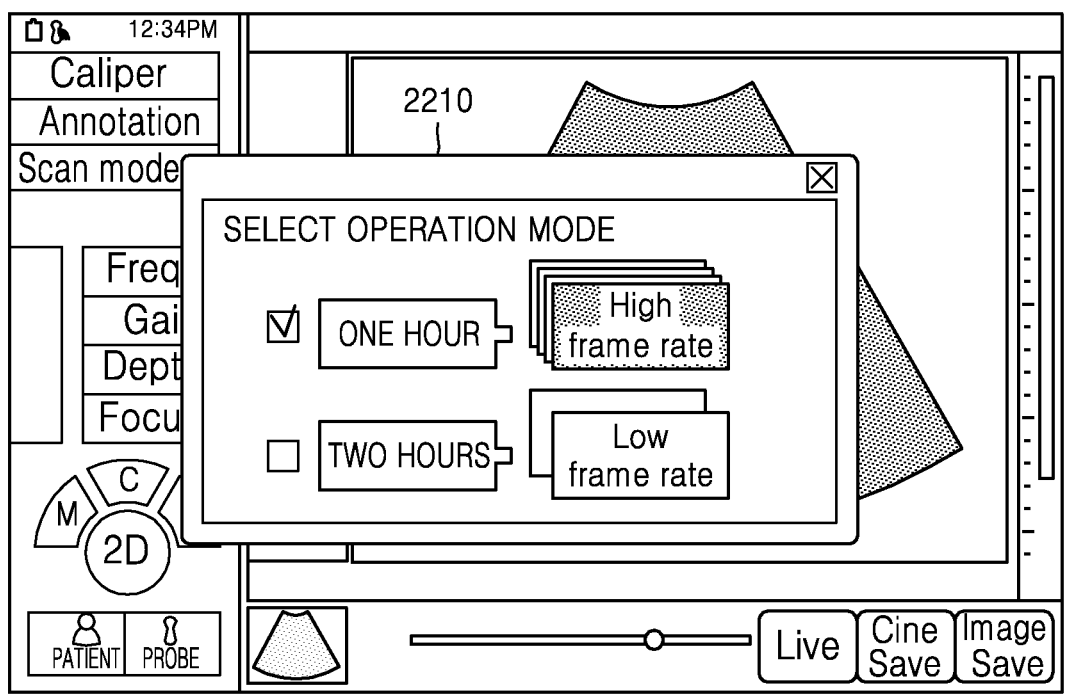
FIG. 22 illustrates an example of a user interface display which is configured for receiving a user input that determines a transmission speed, at which ultrasound image data is transmitted, in consideration of consumption of a battery of an ultrasound probe, according to another exemplary embodiment.
Figure 23:
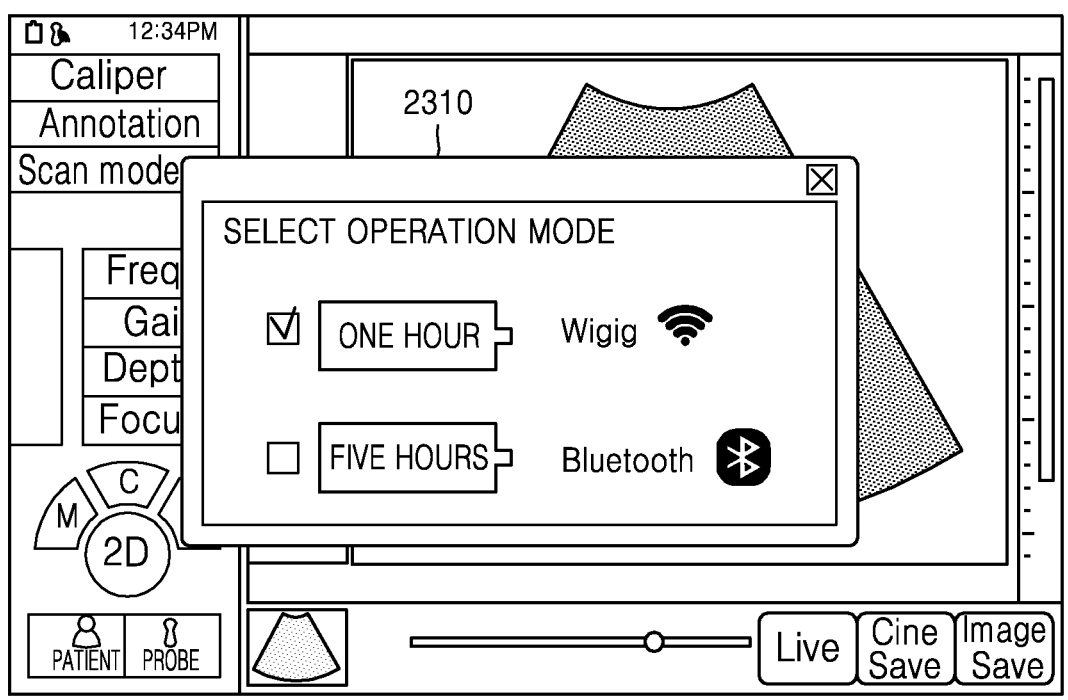
FIG. 23 illustrates an example of a user interface display which is configured for receiving a user input that determines a communication scheme, where ultrasound image data is transmitted, in consideration of consumption of a battery of an ultrasound probe, according to another exemplary embodiment.

FIGS. 21, 22, and 23 illustrate examples of a user interface display which is configured for receiving a user input based on consumption of a battery of an ultrasound probe, according to another exemplary embodiment.

As illustrated in FIG. 21, the ultrasound image providing apparatus 200 may display a user interface 2110 for receiving a user input that determines a quality of ultrasound image data received from the ultrasound probe 100 in consideration of consumption of the battery of the ultrasound probe 100.

For example, the battery of the ultrasound probe 100 connected to the ultrasound image providing apparatus 200 may support transmission of high-quality ultrasound image data for one hour and may support transmission of low-quality ultrasound image data for two hours. A user may select, via the user interface 2110, the quality of the ultrasound image data, to be transmitted by the ultrasound probe 100, as one of high image quality and low image quality.

The ultrasound probe 100 may extract information about a user input from a control signal received from the ultrasound image providing apparatus 200 and determine at least one parameter value that corresponds to an image quality selected by the user.

Alternatively, as illustrated in FIG. 22, the ultrasound image providing apparatus 200 may display a user interface 2210 for receiving a user input that determines a transmission speed of ultrasound image data received from the ultrasound probe 100 in consideration of consumption of the battery of the ultrasound probe 100.

For example, the battery of the ultrasound probe 100 connected to the ultrasound image providing apparatus 200 may support transmission of high-speed ultrasound image data for one hour and may support transmission of low-speed ultrasound image data for two hours. The user may select, via the user interface 2210, the transmission speed of the ultrasound image data, to be transmitted by the ultrasound probe 100, as one of a high speed and a low speed.

The ultrasound probe 100 may extract the information about the user input from the control signal received from the ultrasound image providing apparatus 200 and determine the transmission speed of the ultrasound image data, based on the user input.

Alternatively, as illustrated in FIG. 23, the ultrasound image providing apparatus 200 may display a user interface 2310 for receiving a user input that determines a transmission scheme, which is used by the ultrasound probe 100 to transmit ultrasound image data, in consideration of consumption of the battery of the ultrasound probe 100.

For example, the battery of the ultrasound probe 100 connected to the ultrasound image providing apparatus 200 may support transmission of ultrasound image data using WiGig for one hour and may support transmission of ultrasound image data using Bluetooth for five hours. The user may select, via the user interface 2310, a communication scheme, according to which the ultrasound probe 100 transmits the ultrasound image data, as one of WiGig and Bluetooth.

The ultrasound probe 100 may extract the information about the user input from the control signal received from the ultrasound image providing apparatus 200 and determine a communication scheme according to which the ultrasound image data is transmitted, based on the user input.

When an ultrasound probe is dependent on one ultrasound image providing apparatus, a plurality of ultrasound probes may need to be provided in correspondence to each ultrasound image providing apparatus, which is costly and difficult to manage. Therefore, an ultrasound probe needs to communicate with a plurality of ultrasound image providing apparatuses without being dependent on a single ultrasound image providing apparatus. Characteristics and/or specifications of a plurality of ultrasound image providing apparatuses connectable to an ultrasound probe may differ. Accordingly, an ultrasound probe and a method of operating the same, which transmit appropriate ultrasound image data according to a characteristic and/or a specification of an ultrasound image providing apparatus connected to an ultrasound probe, is needed.

The ultrasound probe 100, according to another exemplary embodiment, may adjust at least one selected from among the quality of the ultrasound image data, the transmission speed of the ultrasound image data, and a communication scheme, based on a characteristic of the ultrasound image providing apparatus 200 which is wirelessly connected to the ultrasound probe 100.

Figure 24:
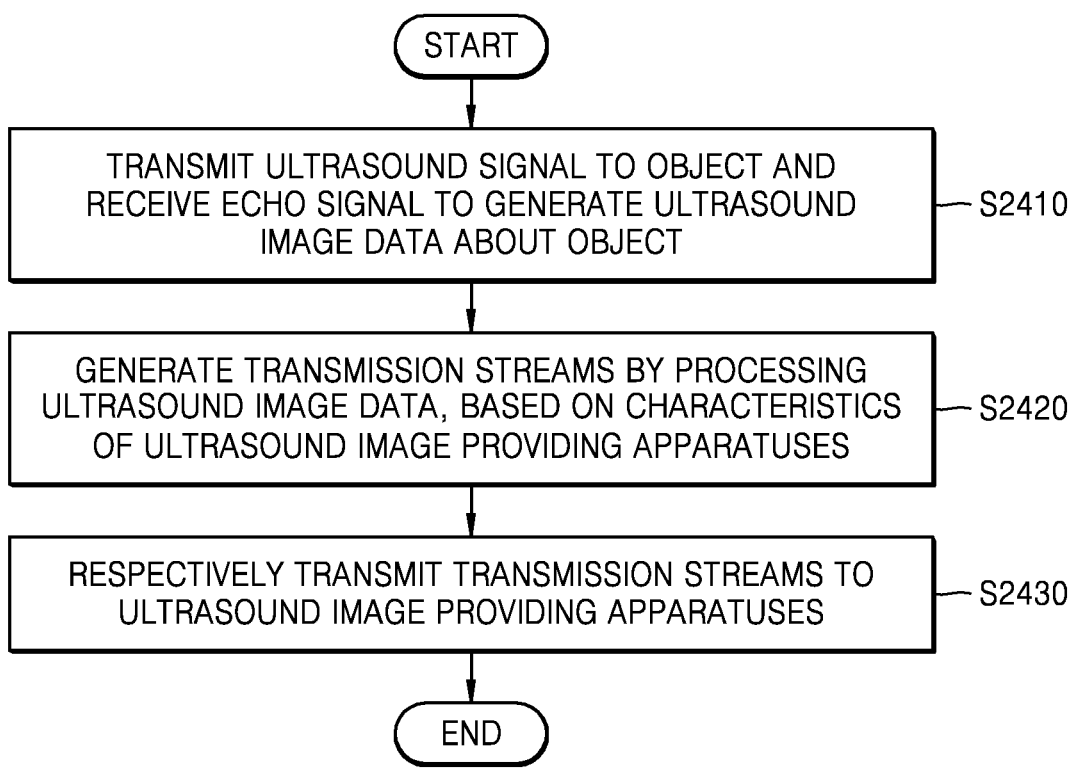
FIG. 24 is a flowchart for describing a method of operating an ultrasound probe which transmits ultrasound image data to a plurality of ultrasound image providing apparatuses, according to another exemplary embodiment.

FIG. 24 is a flowchart for describing a method of operating an ultrasound probe which is wirelessly connected to a plurality of ultrasound image providing apparatuses via different communication channels, according to another exemplary embodiment.

In operation S2410, the ultrasound probe 100 according to another exemplary embodiment may transmit an ultrasound signal toward an object and receive an echo signal to generate ultrasound image data about the object.

In operation S2420, the ultrasound probe 100 according to another exemplary embodiment may generate a plurality of transmission streams by processing the ultrasound image data, based on respective characteristics of a plurality of ultrasound image providing apparatuses.

The ultrasound probe 100 according to another exemplary embodiment may be wirelessly connected to the plurality of ultrasound image providing apparatuses via different respective communication channels.

The ultrasound probe 100 may be wirelessly connected to the ultrasound image providing apparatus 200 by using any of various wireless communication schemes (for example, wireless LAN, Wi-Fi, Bluetooth, Zigbee, Wi-Fi direct (WFD), ultra wideband (UWB), infrared data association (IrDA), Bluetooth low energy (BLE), and near field communication (NFC)) using any of various communication channels.

The ultrasound probe 100 may be wirelessly connected to the ultrasound image providing apparatus 200 by a user's motion. The user's motion may include an operation that contacts the ultrasound probe 100 or places it in close proximity to a diagnostic apparatus 200, selects an ultrasound image providing apparatus, which is to be connected to the ultrasound probe 100, by using the ultrasound probe 100, and/or selects a connection with the ultrasound probe 100 by using the ultrasound image providing apparatus 200.

The ultrasound probe 100 may acquire information about a characteristic of the ultrasound image providing apparatus 200 connected to the ultrasound probe 100.

The information about the characteristic of the ultrasound image providing apparatus 200 may include at least one selected from among a kind of data which can be processed by the ultrasound image providing apparatus 200, a wireless communication scheme which can be used by the ultrasound image providing apparatus 200, a bandwidth available to the ultrasound image providing apparatus 200, a transmission speed based on a communication channel between the ultrasound image providing apparatus 200 and the ultrasound probe 100, the kind of the communication channel, a version of the ultrasound image providing apparatus 200, a specification of the ultrasound image providing apparatus 200, and an identifier of the ultrasound image providing apparatus 200, but is not limited thereto. The information about the characteristic of the ultrasound image providing apparatus 200 may include, for example, function information of the ultrasound image providing apparatus 200, such as a quality of an ultrasound image capable of being displayed by the ultrasound image providing apparatus 200.

The ultrasound probe 100 may acquire the information about the characteristic of the ultrasound image providing apparatus 200 during a session which is established between the ultrasound image providing apparatus 200 and the ultrasound probe 100. The ultrasound probe 100 may acquire information about the ultrasound image providing apparatus 200 while the ultrasound probe 100 is exchanging a message, which is used to establish the session, with the ultrasound image providing apparatus 200.

For example, the ultrasound probe 100 may receive the information about the characteristic of the ultrasound image providing apparatus 200 from the ultrasound image providing apparatus 200 which is connected to the ultrasound probe 100.

The ultrasound probe 100 may request, from the ultrasound image providing apparatus 200, transmission of the information about the characteristic of the ultrasound image providing apparatus 200. In response to the received request, the ultrasound image providing apparatus 200 may transmit information about the ultrasound image providing apparatus 200 to the ultrasound probe 100.

For example, the ultrasound probe 100 may receive information about at least one selected from the kind of data which is to be processed by the ultrasound image providing apparatus 200, a wireless communication scheme which is to be used by the ultrasound image providing apparatus 200, a bandwidth which is to be used by the ultrasound image providing apparatus 200, and the kind of a communication channel which is to be used by the ultrasound image providing apparatus 200.

Alternatively, the ultrasound probe 100 may receive information about a capability of the ultrasound image providing apparatus 200 from the ultrasound image providing apparatus 200. For example, the ultrasound probe 100 may receive information about at least one selected from among all the kinds of data which are to be processed by the ultrasound image providing apparatus 200, all wireless communication schemes which are supported by the ultrasound image providing apparatus 200, a bandwidth which is to be used by the ultrasound image providing apparatus 200, and all the kinds of communication channels which are to be supported by the ultrasound image providing apparatus 200.

The ultrasound probe 100 may select at least one from among the kind of data which is the most suitable for the ultrasound image providing apparatus 200, a wireless communication scheme which is the most suitable for the ultrasound image providing apparatus 200, a bandwidth which is the most suitable for the ultrasound image providing apparatus 200, and a communication channel which is the most suitable for the ultrasound image providing apparatus 200. For example, the ultrasound probe 100 may select a communication scheme, a communication channel, or a kind of data that enables the ultrasound image providing apparatus 200 to provide an ultrasound image to a user at a highest resolution or a highest frame rate.

As another example, the ultrasound probe 100 may acquire only an identifier of the ultrasound image providing apparatus 200 from the ultrasound image providing apparatus 200 that is connected to the ultrasound probe 100. The ultrasound probe 100 may search for information stored in the ultrasound probe 100, based on the acquired identifier, thereby acquiring information about a characteristic of the ultrasound image providing apparatus 200.

The ultrasound probe 100 may acquire information about the characteristic of the ultrasound image providing apparatus 200, based on a user input. For example, the ultrasound probe 100 may acquire information about a communication channel, through which the ultrasound probe 100 is connected to the ultrasound image providing apparatus 200, from a user input.

The ultrasound probe 100, according to another exemplary embodiment, may acquire respective characteristics of a plurality of ultrasound image providing apparatuses and generate a plurality of transmission streams by processing the ultrasound image data, based on the acquired characteristics.

The ultrasound probe 100 according to another exemplary embodiment may perform additional signal processing on the ultrasound image data, based on the characteristics of the plurality of ultrasound image providing apparatuses, thereby increasing or decreasing the amount of the ultrasound image data.

The ultrasound probe 100 may generate the plurality of transmission streams by processing the ultrasound image data so that respective ultrasound images generated from the plurality of ultrasound streams have different resolutions, based on respective characteristics of communication channels via which a plurality of ultrasound image providing apparatuses are connected to the ultrasound probe 100. For example, the ultrasound probe 100 may process ultrasound image data so that an ultrasound image has a lower resolution as a bandwidth of a communication channel, via which an ultrasound image providing apparatus is connected to the ultrasound probe 100, becomes narrower (i.e., the amount of data which is transmitted via the communication channel per unit time is reduced). The ultrasound probe 100 may generate a transmission stream that includes the processed ultrasound image data.

In operation S2430, the ultrasound probe 100 according to another exemplary embodiment may respectively transmit each of the plurality of transmission streams, which are generated in operation S2420, to a corresponding one of a plurality of ultrasound image providing apparatuses. In this case, the ultrasound probe 100 may adjust a transmission speed of each of the transmission streams, based on respective characteristics of the plurality of ultrasound image providing apparatuses.

The plurality of transmission streams transmitted from the ultrasound probe 100 may be used to display an ultrasound image via corresponding ones of the plurality of ultrasound image providing apparatuses.

Figure 25:
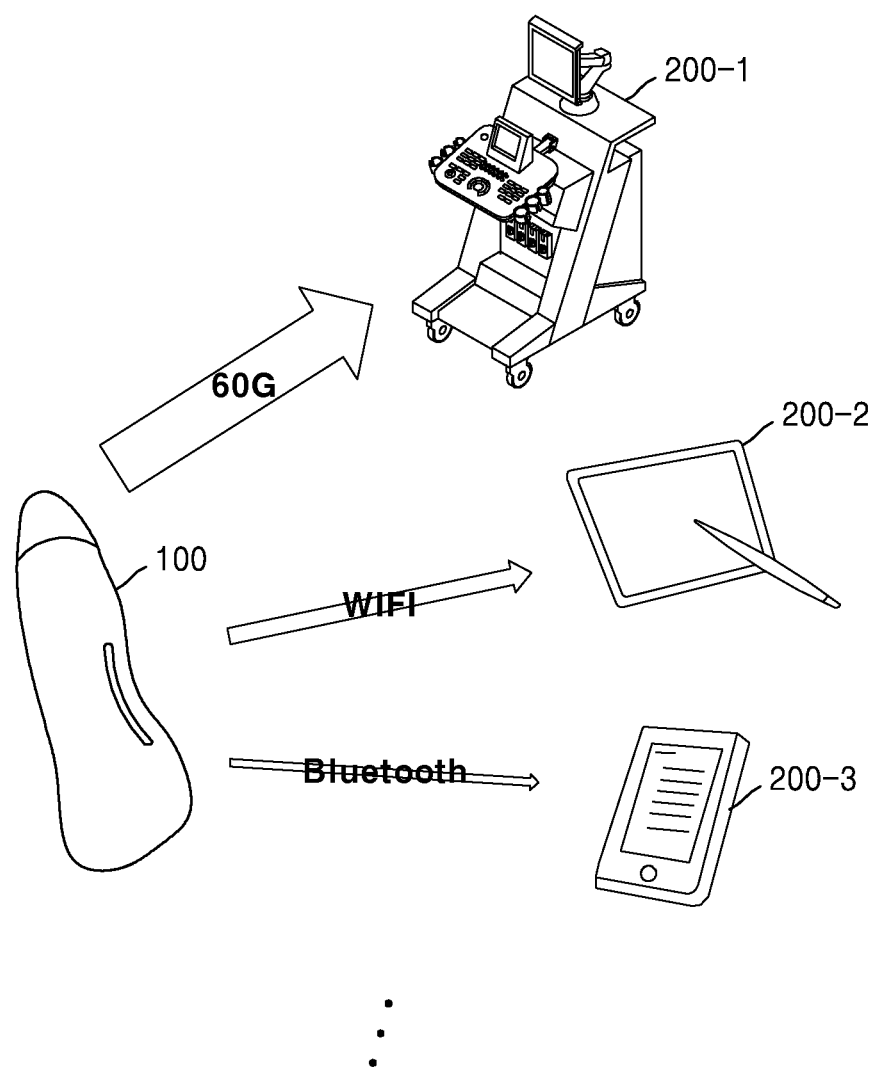
FIG. 25 is a diagram for describing a method of transmitting, by an ultrasound probe according to another exemplary embodiment, ultrasound image data to a plurality of ultrasound image providing apparatuses.

FIG. 25 is a diagram for describing a method of transmitting, by an ultrasound probe according to another exemplary embodiment, ultrasound image data to a plurality of ultrasound image providing apparatuses.

For example, as illustrated in FIG. 25, an ultrasound probe 100 according to another exemplary embodiment may be wirelessly connected to a plurality of ultrasound image providing apparatuses 200-1, 200-2, and 200-3. The plurality of ultrasound image providing apparatuses 200-1, 200-2, and 200-3 may respectively include a cart type ultrasound diagnostic apparatus 200-1, a tablet personal computer (PC) 200-2, and a smartphone 200-3. The ultrasound image providing apparatuses of FIG. 25 may have different characteristics and/or specifications. Also, the ultrasound image providing apparatuses 200-1, 200-2, and 200-3 may use different respective wireless communication schemes. As illustrated in FIG. 9, examples of a wireless communication scheme used by the ultrasound image providing apparatuses 200-1, 200-2, and 200-3 may include 60 G, Wi-Fi, and Bluetooth.

The ultrasound probe 100 according to another exemplary embodiment may transmit pieces of ultrasound image data, having different respective image qualities, to the plurality of ultrasound image providing apparatuses 200-1, 200-2, and 200-3 which are connected to the ultrasound probe 100 via different communication channels (i.e., by using different wireless communication schemes), respectively.

As illustrated in FIG. 25, the ultrasound probe 100 may be wirelessly connected to the cart type ultrasound diagnostic apparatus 200-1 in a frequency band of 60 GHz. The ultrasound probe 100 may transmit high-quality ultrasound image data to the cart type ultrasound diagnostic apparatus 200-1, based on a characteristic of the cart type ultrasound diagnostic apparatus 200-1. For example, the ultrasound probe 100 may transmit raw data, which is generated from an echo signal acquired from an object, to the cart type ultrasound diagnostic apparatus 200-1. The cart type ultrasound diagnostic apparatus 200-1 may process the received raw data. The ultrasound probe 100 may transmit the raw data to the cart type ultrasound diagnostic apparatus 200-1 and enable the cart type ultrasound diagnostic apparatus 200-1 to process the transmitted raw data into various types.

The ultrasound probe 100 may be connected to the tablet PC 200-2 in a Wi-Fi scheme. The ultrasound probe 100 may perform post-processing based on a characteristic of the tablet PC 200-2 and transmit ultrasound image data (for example, ultrasound image data having a relatively low image quality) to the tablet PC 200-2. The ultrasound probe 100 may perform additional processing on the raw data and transmit data, having a resolution that is suitable for the tablet PC 200-2, to the tablet PC 200-2.

The ultrasound probe 100 may be connected to the smartphone 200-3 in a Bluetooth scheme. The ultrasound probe 100 may transmit ultrasound image data having a very low frame rate to the smartphone 200-3, based on a characteristic of the smartphone 200-3. For example, the ultrasound probe 100 may perform additional processing on raw data and thus transmit the ultrasound image data having a very low frame rate to the smartphone 200-3. Alternatively, the ultrasound probe 100 may transmit only a still image to the smartphone 200-3. In this case, the ultrasound image data or the still image transmitted to the smartphone 200-3 may be data on which additional processing has been performed to have a very low resolution.

As described above, the ultrasound probe 100 according to another exemplary embodiment transmits pieces of ultrasound image data having the different respective image qualities to a plurality of ultrasound image providing apparatuses at different transmission speeds, respectively.

In FIGS. 24 and 25, a case where the ultrasound probe 100 is connected to a plurality of ultrasound image providing apparatuses is illustrated as an example. However, the ultrasound probe 100 according to an exemplary embodiment or another exemplary embodiment is not limited to that shown in FIGS. 24 and 25.

In order to be connected to one ultrasound image providing apparatus, the ultrasound probe 100 may adjust at least one of a quality of ultrasound image data, a transmission speed of the ultrasound image data, and a communication scheme, based on a characteristic of the ultrasound image providing apparatus 200 wirelessly connected to the ultrasound probe 100.

Figure 26:
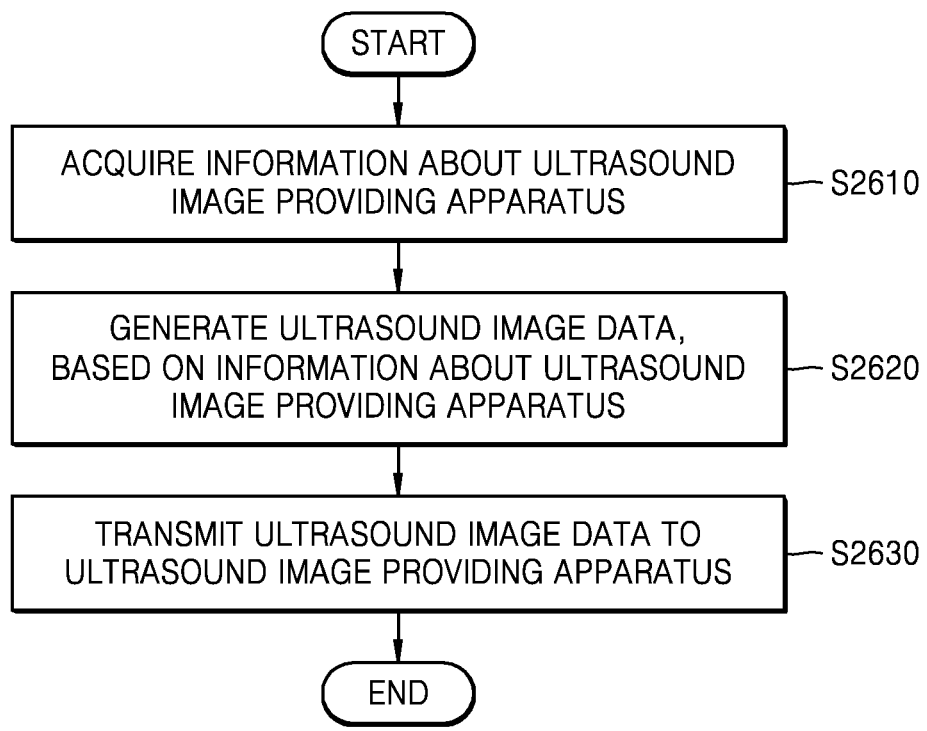
FIG. 26 is a flowchart for describing a method of operating an ultrasound probe which generates and transmits ultrasound image data based on information about an ultrasound image providing apparatus, according to another exemplary embodiment.

FIG. 26 is a flowchart for describing a method of operating an ultrasound probe which generates and transmits ultrasound image data based on information about an ultrasound image providing apparatus, according to another exemplary embodiment.

In operation S2610, the ultrasound probe 100 according to another exemplary embodiment may acquire information about the ultrasound image providing apparatus 200.

The information about the ultrasound image providing apparatus 200 may include at least one of an identifier of the ultrasound image providing apparatus 200, function information of the ultrasound image providing apparatus 200, and state information of the ultrasound image providing apparatus 200.

The function information of the ultrasound image providing apparatus 200 may include at least one selected from among the kind of data which is to be processed by the ultrasound image providing apparatus 200, a quality of ultrasound image data supportable by the ultrasound image providing apparatus 200, a wireless communication scheme used by the ultrasound image providing apparatus 200, a bandwidth available to the ultrasound image providing apparatus 200, a transmission speed based on a communication channel between the ultrasound image providing apparatus 200 and the ultrasound probe 100, the kind of the communication channel, a version of the ultrasound image providing apparatus 200, an application used by the ultrasound image providing apparatus 200, a diagnosis division or a diagnosis part available to the ultrasound image providing apparatus 200, and a class of the ultrasound image providing apparatus 200.

The application may include all application software which is used by the ultrasound image providing apparatus 200 for processing an image. For example, the ultrasound image providing apparatus 200 may be configured to use different applications according to a diagnosis or a diagnosis part where an ultrasound image processed by the ultrasound image providing apparatus 200 is used. For example, the diagnosis division may include any of obstetrics (OB), gynecology (GYN), pediatrics (PD), chest surgery (CS), radiology (RD), neurosurgery (NS), and abdomen.

The class of the ultrasound image providing apparatus 200 may be determined based on a quality of an ultrasound image provided by the ultrasound image providing apparatus 200 or the number of applications, or may be determined by a user or a manufacturer of the ultrasound image providing apparatus 200.

Moreover, the state information of the ultrasound image providing apparatus 200 may include at least one selected from among whether the ultrasound image providing apparatus 200 is communicating with the ultrasound probe 100, information about the ultrasound probe 100 which is communicating with the ultrasound image providing apparatus 200, a wireless communication intensity between the ultrasound image providing apparatus 200 and the ultrasound probe 100, and a position of the ultrasound image providing apparatus 200.

The ultrasound probe 100 may acquire information about the ultrasound image providing apparatus 200, based on a data signal received from the ultrasound image providing apparatus 200 wirelessly connected to the ultrasound probe 100. Also, based on a user input, the ultrasound probe 100 may acquire the information about the ultrasound image providing apparatus 200 and acquire pre-stored information from a storage unit.

For example, the ultrasound probe 100 may acquire the information about the ultrasound image providing apparatus 200 during a session which is established between the ultrasound image providing apparatus 200 and the ultrasound probe 100. The ultrasound probe 100 may acquire the information about the ultrasound image providing apparatus 200 in a process of exchanging a message for establishing a session with the ultrasound image providing apparatus 200.

The ultrasound probe 100 may issue a request, to the ultrasound image providing apparatus 200, to transmit information about a characteristic of the ultrasound image providing apparatus 200. In response to the request received from the ultrasound probe 100, the ultrasound image providing apparatus 200 may transmit the information about the ultrasound image providing apparatus 200 to the ultrasound probe 100.

Alternatively, the ultrasound probe 100 may receive information about a capability of the ultrasound image providing apparatus 200 from the ultrasound image providing apparatus 200. For example, the ultrasound probe 100 may receive information about at least one selected from among all the kinds of data which are to be processed by the ultrasound image providing apparatus 200, a quality of ultrasound image data capable of being supported by the ultrasound image providing apparatus 200, all wireless communication schemes capable of being supported by the ultrasound image providing apparatus 200, a bandwidth available to the ultrasound image providing apparatus 200, a reception speed (i.e., a transmission speed at which the ultrasound probe 100 transmits the ultrasound image data to the ultrasound image providing apparatus 200 when the ultrasound image providing apparatus 200 smoothly receives the ultrasound image data transmitted by the ultrasound probe 100) at which the ultrasound image providing apparatus 200 receives the ultrasound image data, and all the kinds of communication channels capable of being supported by the ultrasound image providing apparatus 200.

The ultrasound probe 100 may select at least one from among the kind of ultrasound image data which is the most suitable for the ultrasound image providing apparatus 200, a quality of the ultrasound image data which is the most suitable for the ultrasound image providing apparatus 200, a wireless communication scheme which is the most suitable for the ultrasound image providing apparatus 200, a bandwidth which is the most suitable for the ultrasound image providing apparatus 200, a communication channel which is the most suitable for the ultrasound image providing apparatus 200, and a transmission speed of the ultrasound image data which is the most suitable for the ultrasound image providing apparatus 200, based on the information about the capability of the ultrasound image providing apparatus 200. For example, the ultrasound probe 100 may select a transmission speed, a quality, a communication scheme, or a kind of ultrasound image data that enables the ultrasound image providing apparatus 200 to provide an ultrasound image to a user at a highest resolution or a highest frame rate.

As another example, the ultrasound probe 100 may acquire only an identifier of the ultrasound image providing apparatus 200 from the ultrasound image providing apparatus 200 connected to the ultrasound probe 100. The ultrasound probe 100 may search for information pre-stored in the ultrasound probe 100 to acquire the information about the characteristic of the ultrasound image providing apparatus 200, based on the acquired identifier.

As another example, the ultrasound probe 100 may acquire information about the ultrasound image providing apparatus 200, based on a user input. For example, the ultrasound probe 100 may acquire at least one selected from an identifier of the ultrasound image providing apparatus 200, a quality of ultrasound image data capable of being supported by the ultrasound image providing apparatus 200, a wireless communication scheme available to the ultrasound image providing apparatus 200, and a transmission speed of the ultrasound image data transmitted to the ultrasound image providing apparatus 200, based on a user input.

In operation S2620, the ultrasound probe 100 according to an exemplary embodiment or another exemplary embodiment may generate ultrasound image data, based on the information about the ultrasound image providing apparatus 200.

For example, based on the information about the ultrasound image providing apparatus 200, the ultrasound probe 100 may transmit an ultrasound signal toward an object in order to receive an echo signal, thereby generating ultrasound image data about the object.

The ultrasound probe 100 may determine at least one selected from among the kind of ultrasound image data which is the most suitable for the ultrasound image providing apparatus 200, a quality of the ultrasound image data which is the most suitable for the ultrasound image providing apparatus 200, and a transmission speed of the ultrasound image data which is the most suitable for the ultrasound image providing apparatus 200, based on the information about the ultrasound image providing apparatus 200. For example, the ultrasound probe 100 may determine a frame rate or a quality of ultrasound image data that enables the ultrasound image providing apparatus 200 to provide an ultrasound image to the user at a highest resolution or a highest frame rate.

The ultrasound probe 100 may generate process the echo signal to generate ultrasound image data, based on the determined transmission speed or quality.

As another example, the ultrasound probe 100 may acquire pre-generated and pre-stored ultrasound image data from the storage unit and perform additional signal processing on the ultrasound image data, based on the information about the ultrasound image providing apparatus 200.

The ultrasound probe 100 may determine at least one from among the kind of ultrasound image data which is the most suitable for the ultrasound image providing apparatus 200, a quality of the ultrasound image data which is the most suitable for the ultrasound image providing apparatus 200, a wireless communication scheme which is the most suitable for the ultrasound image providing apparatus 200, a bandwidth which is the most suitable for the ultrasound image providing apparatus 200, a communication channel which is the most suitable for the ultrasound image providing apparatus 200, and a transmission speed of the ultrasound image data which is the most suitable for the ultrasound image providing apparatus 200, based on the information about the ultrasound image providing apparatus 200. For example, the ultrasound probe 100 may determine a transmission speed, a quality, a communication scheme, or a kind of ultrasound image data that enables the ultrasound image providing apparatus 200 to provide an ultrasound image to the user at a highest resolution or a highest frame rate.

The ultrasound probe 100 may additionally process the ultrasound image data according to the determined transmission speed, quality, or communication scheme. The ultrasound probe 100 may perform additional signal processing on the ultrasound image data, thereby increasing or decreasing the amount of the ultrasound image data. For example, the ultrasound probe 100 may generate ultrasound image data having various image qualities, based on the information about the ultrasound image providing apparatus 200.

In operation S2630, the ultrasound probe 100 according to an exemplary embodiment may transmit the ultrasound image data, which is generated in operation S2520, to the ultrasound image providing apparatus 200.

For example, the ultrasound probe 100 may transmit the ultrasound image data at a transmission speed which is determined based on the information about the ultrasound image providing apparatus 200. Alternatively, the ultrasound probe 100 may transmit the ultrasound image data by using a communication scheme which is determined based on the information about the ultrasound image providing apparatus 200.

Figure 27:
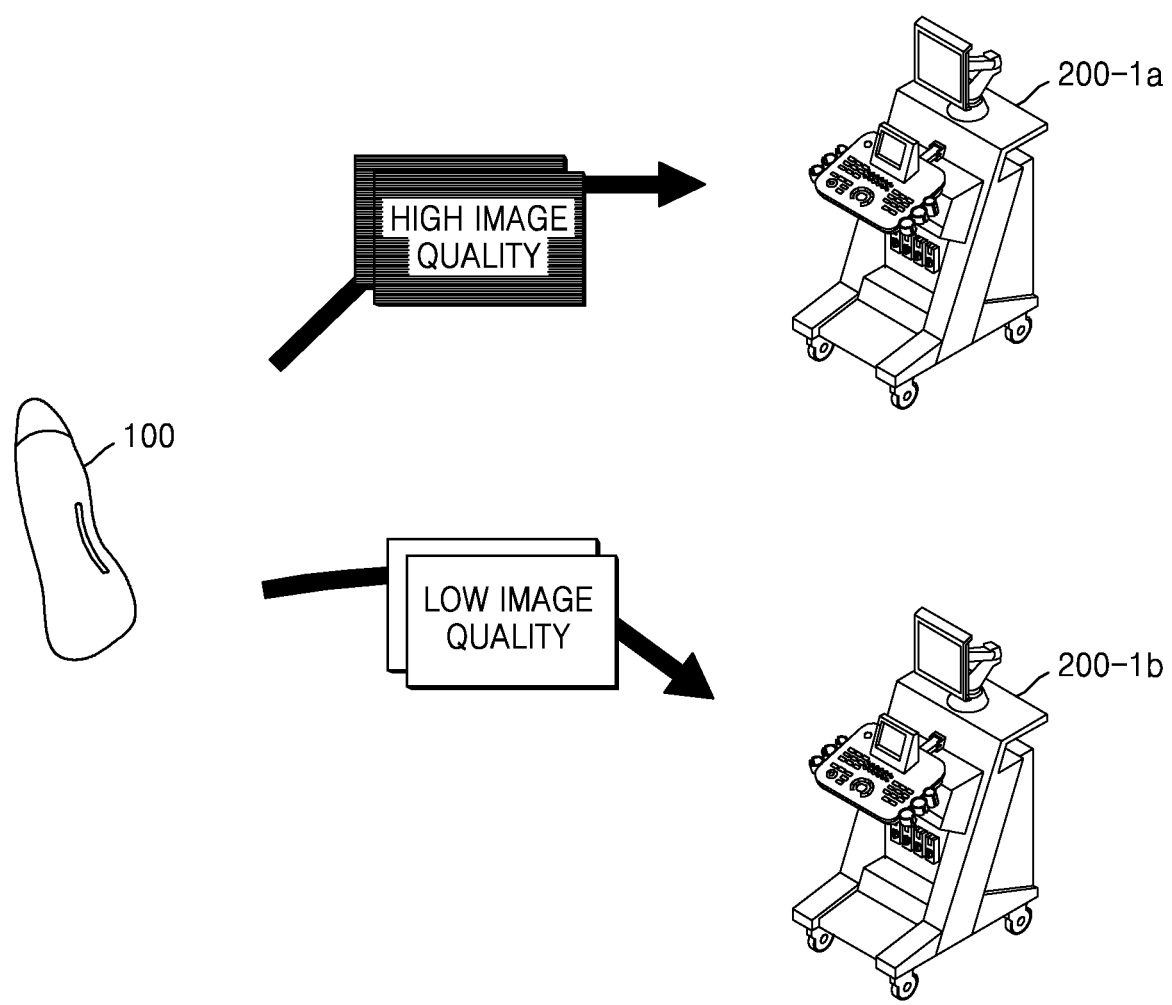
FIGS. 27 and 28 are diagrams for describing a method of operating an ultrasound probe which generates and transmits ultrasound image data based on information about an ultrasound image providing apparatus, according to another exemplary embodiment.
Figure 28:
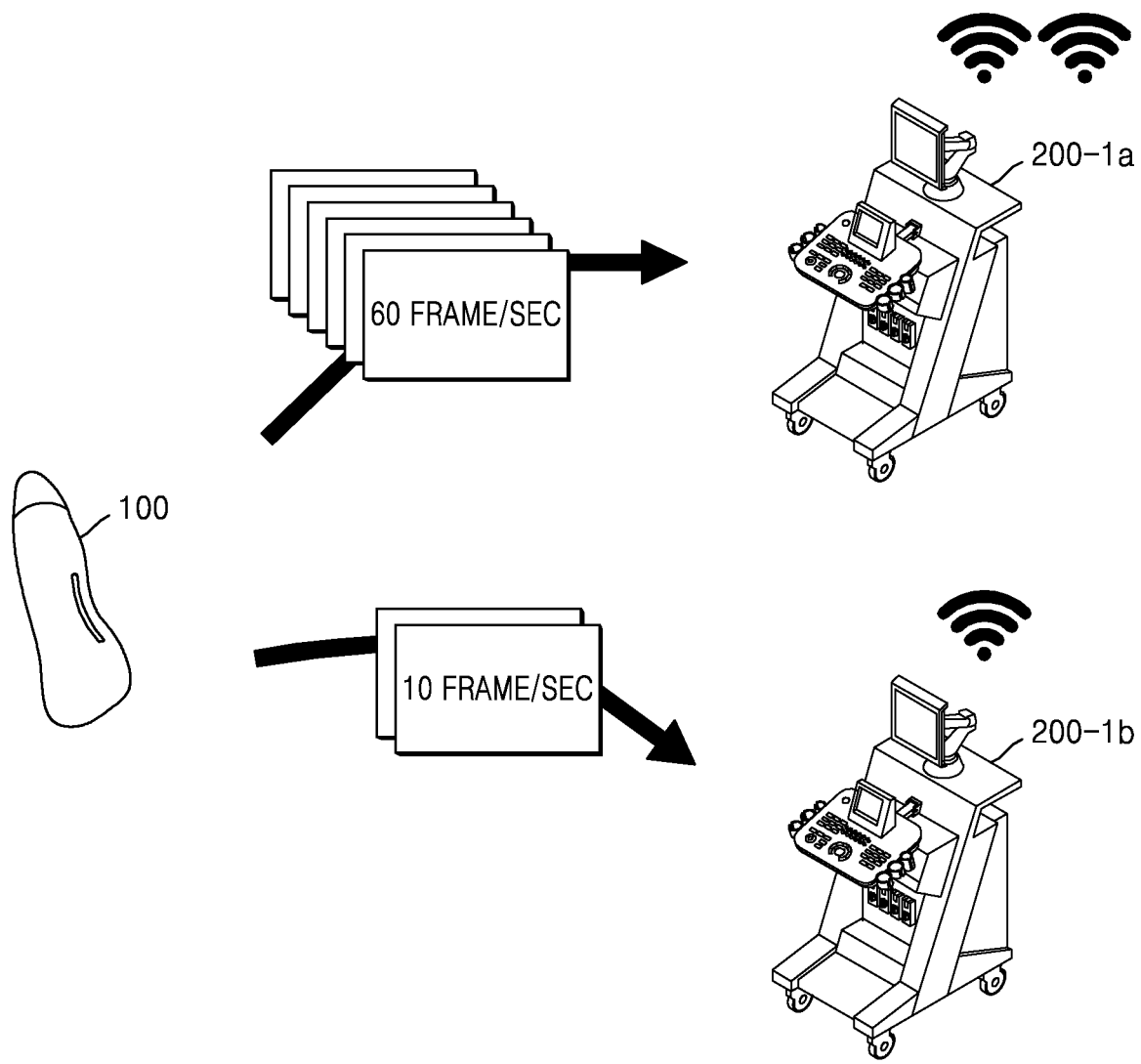

FIGS. 27 and 28 are diagrams for describing a method of operating an ultrasound probe which generates and transmits ultrasound image data based on information about an ultrasound image providing apparatus, according to another exemplary embodiment.

As illustrated in FIG. 27, the ultrasound probe 100 may acquire information about the ultrasound image providing apparatus 200 and generate ultrasound image data, based on the acquired information about the ultrasound image providing apparatus 200.

For example, when an ultrasound image providing apparatus 200-1a connected to the ultrasound probe 100 is capable of receiving and processing high-quality ultrasound image data, the ultrasound probe 100 may transmit the high-quality ultrasound image data to the ultrasound image providing apparatus 200-1a. Conversely, when an ultrasound image providing apparatus 200-1b connected to the ultrasound probe 100 is capable of receiving and processing low-quality ultrasound image data, the ultrasound probe 100 may transmit the low-quality ultrasound image data to the ultrasound image providing apparatus 200-1b.

As illustrated in FIG. 28, the ultrasound probe 100 may acquire information about the ultrasound image providing apparatus 200 and generate and transmit ultrasound image data, based on the acquired information about the ultrasound image providing apparatus 200.

For example, when an ultrasound image providing apparatus 200-1a connected to the ultrasound probe 100 includes a multi-antenna and thus is capable of receiving ultrasound image data having a high frame rate, the ultrasound probe 100 may transmit the ultrasound image data having a relatively high frame rate (e.g., 60 frames/second) to the ultrasound image providing apparatus 200-1a. Conversely, when an ultrasound image providing apparatus 200-1b connected to the ultrasound probe 100 includes a multi-antenna and thus is capable of receiving ultrasound image data having a low frame rate, the ultrasound probe 100 may transmit the ultrasound image data having a relatively low frame rate (e.g., 10 frames/second) to the ultrasound image providing apparatus 200-1b.

Figure 29:
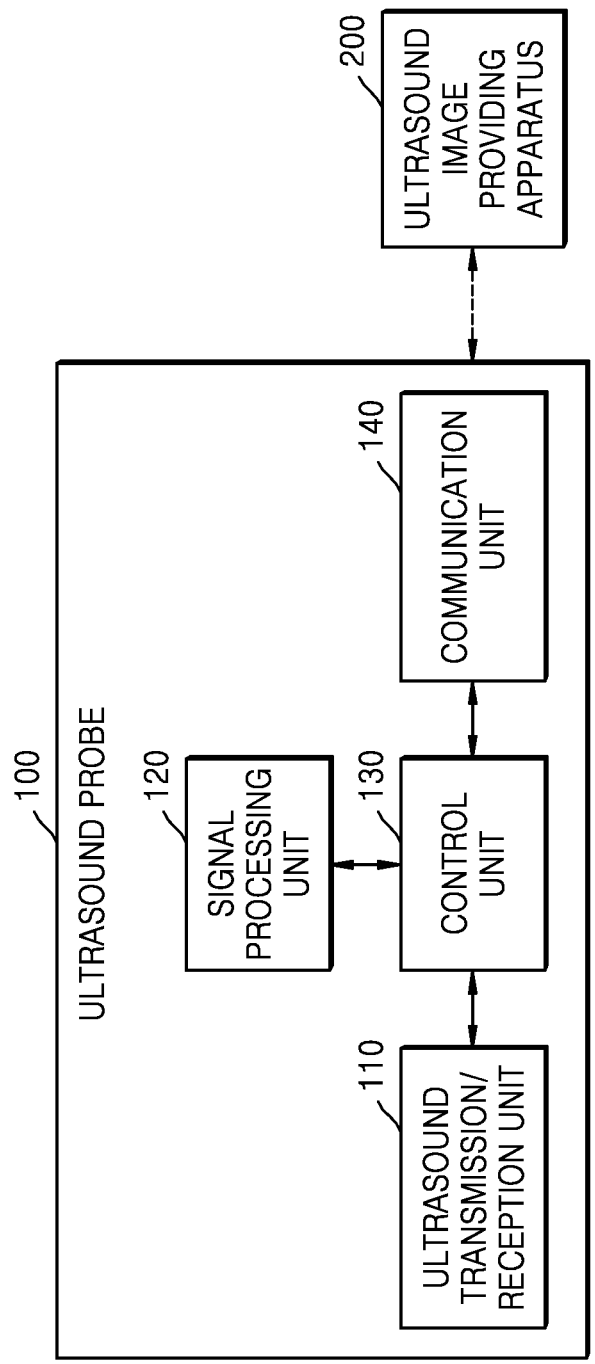
FIG. 29 is a block diagram of an ultrasound probe, according to various exemplary embodiments.
Figure 30:
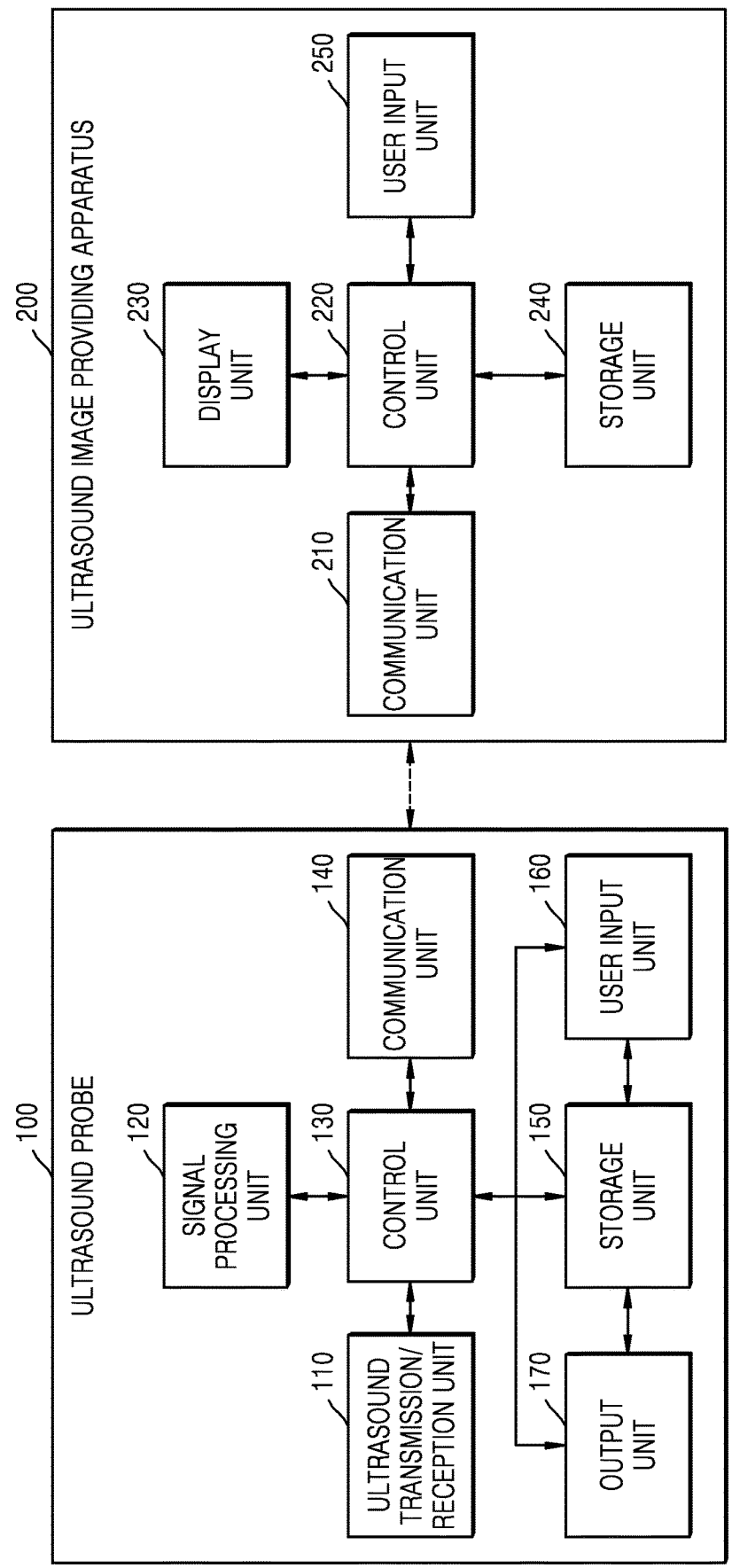
FIG. 30 is a block diagram of an ultrasound probe and an ultrasound image providing apparatus, according to various exemplary embodiments.

FIGS. 29 and 30 are block diagrams of ultrasound probes, according to various exemplary embodiments.

The elements of the ultrasound probe 100 according to an exemplary embodiment perform the operations of the method of operating the ultrasound probe 100 illustrated in FIGS. 3, 6, 9, 14, 18, 24, and 26. Thus, although not described below, the above-described details of the method of operating the ultrasound probe 100 illustrated in FIGS. 3, 6, 9, 14, 18, 24, and 26 may be applied to an ultrasound probe 100 of FIGS. 29 and 30.

As illustrated in FIG. 29, an ultrasound probe 100 according to various exemplary embodiments includes an ultrasound transmission/reception unit (also referred to herein as an "ultrasound transceiver") 110, a signal processing unit (also referred to herein as a "signal processor") 120, a control unit (also referred to herein as a "controller") 130, and a communication unit (also referred to herein as a "communicator") 140.

The ultrasound probe 100 according to various exemplary embodiments may be wirelessly connected to an ultrasound image providing apparatus 200 via a communication channel. Also, the ultrasound probe 100 according to various exemplary embodiments may be connected to a plurality of ultrasound image providing apparatuses via different respective communication channels (i.e., by using different wireless communication schemes). The ultrasound probe 100 according to various exemplary embodiments may simultaneously or sequentially transmit pieces of ultrasound image data about an object to the plurality of ultrasound image providing apparatuses via the different communication channels.

The ultrasound transmission/reception unit 110 may transmit an ultrasound signal toward an object, and receive an echo signal.

The ultrasound transmission/reception unit 110 generates pulses for forming transmission ultrasound waves based on a predetermined pulse repetition frequency (PRF). The ultrasound transmission/reception unit 110 applies a delay time for determining transmission directionality to the pulses. Pulses to which a delay time is applied correspond to a plurality of piezoelectric vibrators included in a transducer, respectively. The ultrasound transmission/reception unit 110 applies a driving signal (or a driving pulse) to the probe 20 as a timing that corresponds to each pulse to which a delay time is applied, thereby transmitting an ultrasound signal toward the object.

The signal processing unit 120 may process the echo signal received from the ultrasound transmission/reception unit 110 in order to generate ultrasound image data. The signal processing unit 120 may amplify the echo signal in each channel, and analog-to-digital convert an amplified response signal. The signal processing unit 120 may apply a delay time, used to determine reception directionality, to the digital-converted response signal. The signal processing unit 120 may perform a summation of echo signals, to which the delay time is applied, in order to generate the ultrasound image data.

The ultrasound image data may be used for displaying an ultrasound image via the ultrasound image providing apparatus 200. The ultrasound image providing apparatus 200 may generate an ultrasound image from the ultrasound image data received from the ultrasound probe 100, and display the ultrasound image. The ultrasound image displayed by the ultrasound image providing apparatus 200 may include not only a grayscale ultrasound image obtained by scanning an object in any of an amplitude (A) mode, a brightness (B) mode, and a motion (M) mode, but also any of a blood flow Doppler image showing flow of blood (also referred to as a color Doppler image), a tissue Doppler image showing movement of tissues, and a spectral Doppler image showing moving speed of an object as a waveform.

The control unit 130 may control an overall operation of the ultrasound probe 100. The control unit 130 may control the ultrasound transmission/reception unit 110, the signal processing unit 120, and the communication unit 140, and control an operation between the ultrasound probe 100 and the ultrasound image providing apparatus 200.

The control unit 130 may determine at least one selected from among at least one parameter value associated with a quality of ultrasound image data, a transmission speed of the ultrasound image data, and a communication scheme which is used to transmit the ultrasound image data.

The at least one parameter value associated with the quality of the ultrasound image may include at least one selected from among the number of scan lines constituting the frame of the ultrasound image, the number of sampling points which are set on a scan line, and the number of bits which are generated by quantizing data which is acquired with respect to a sampling point.

For example, the control unit 130 may change at least one selected from among a quality of ultrasound image data, a transmission speed of the ultrasound image data, and a communication scheme, based on a state of a communication channel.

For example, when the bandwidth of the communication channel is narrowed, the control unit 130 may adjust the at least one parameter value associated with the quality of the ultrasound image, based on a reduction amount (i.e., an amount of narrowing) of the bandwidth. The control unit 130 may control at least one selected from among the ultrasound transmission/reception unit 110 and the signal processing unit 120 so as to generate ultrasound image data about the object, based on a determined parameter value.

Alternatively, when the bandwidth of the communication channel is narrowed, the control unit 130 may lower the transmission speed of the frame, based on the reduction amount of the bandwidth. In order to lower the transmission speed of the frame, the control unit 130 may divide and transmit data for each frame which is included in the ultrasound image data.

The control unit 130 may select one mode from among first and second modes, based on an application used by the ultrasound probe 100. When the first mode is selected, the ultrasound probe 100 may adjust the at least one parameter value, based on a change in the bandwidth of the communication channel. When the second mode is selected, the ultrasound probe 100 may adjust the transmission speed of the frame, based on the change in the bandwidth of the communication channel.

As another example, the control unit 130 may change at least one selected from among a quality of ultrasound image data, a transmission speed of the ultrasound image data, and a communication scheme, based on a user input.

The control unit 130 may determine at least one parameter value associated with ultrasound image quality, based on a user input. The control unit 130 may control at least one selected from among the ultrasound transmission/reception unit 110 and the signal processing unit 120 to generate ultrasound image data about an object, based on the determined parameter value.

The control unit 130 may determine a transmission speed of the ultrasound image data, based on the determined parameter value. When at least one parameter value for degrading the ultrasound image quality is determined, the control unit 130 may lower the transmission speed of the ultrasound image data.

Alternatively, the control unit 130 may determine a transmission speed at which the ultrasound image data is transmitted, based on a user input. The control unit 130 may determine the at least one parameter value associated with the ultrasound image quality. The control unit 130 may control at least one selected from among the ultrasound transmission/reception unit 110 and the signal processing unit 120 to generate the ultrasound image data about the object, based on the determined parameter value.

The control unit 130 may determine the at least one parameter value associated with the ultrasound image quality, based on the determined transmission speed. When the transmission speed of the ultrasound image data is lowered, the control unit 130 may decrease at least one selected from among the number of scan lines constituting one frame of an ultrasound image, the number of sampling points which are set on the scan lines, and the number of bits which are generated by quantizing data acquired from the sampling points.

As another example, the control unit 130 may change at least one selected from among the quality of the ultrasound image data, the transmission speed of the ultrasound image data, and a communication scheme depending on a characteristic of the ultrasound image providing apparatus 200 which is wirelessly connected to the ultrasound probe 100.

Alternatively, the control unit 130 may generate a plurality of transmission streams by processing the ultrasound image data, based on respective characteristics of a plurality of ultrasound image providing apparatuses. For example, the control unit 130 may process the ultrasound image data so that respective ultrasound images generated from the plurality of ultrasound streams have different resolutions, based on respective characteristics of communication channels via which the plurality of ultrasound image providing apparatuses are connected to the ultrasound probe 100, and may generate the plurality of transmission streams including the processed ultrasound image data.

The communication unit 140 may transmit ultrasound image data to the ultrasound image data to the ultrasound image providing apparatus 200 at a transmission speed of a frame determined by the control unit 130. The ultrasound image data may be used to display an ultrasound image by using the ultrasound image providing apparatus 200. The communication unit 140 may communicate by wire or wirelessly with the ultrasound image providing apparatus 200. Also, the communication unit 140 may receive a control signal, used to control the ultrasound probe 100, from the ultrasound image providing apparatus 200.

The communication unit 140 may transmit a session establishment request signal to the ultrasound image providing apparatus 200, and receive a session establishment check signal from the ultrasound image providing apparatus 200. The session establishment check signal may include bandwidth information.

The communication unit 140 may transmit information about at least one selected from among the at least one parameter value and the transmission speed of the frame to the ultrasound image providing apparatus 200 in conjunction with the ultrasound image data. The information about the at least one selected from among the at least one parameter value and the transmission speed may be used by the ultrasound image providing apparatus 200 for generating an ultrasound image from the ultrasound image data.

The communication unit 140 is connected to a network 30 in a wired or wireless manner in order to communicate with an external device or server. The communicator 140 may exchange data with a hospital server or a medical apparatus of a hospital which is connected thereto through a medical image information system (a PACS). Also, the communicator 140 may perform data communication according to the digital imaging and communications in medicine (DICOM) standard.

The communication unit 140 may transmit and receive data, such as an ultrasound image, ultrasound data, Doppler data, etc. of an object, associated with a diagnosis of the object over a network, and may also transmit and receive a medical image captured by a medical apparatus such as a computed tomography (CT) apparatus, a magnetic resonance imaging (MRI) apparatus, or an X-ray apparatus. Furthermore, the communication unit 140 may receive information on a diagnosis history or treatment schedule of a patient from a server, and use a diagnosis of an object. In addition, the communication unit 140 may perform data communication with a portable terminal of a doctor or a patient, in addition to a server or medical apparatus of a hospital.

Short-distance communication technology, which may be used by the communication unit 140, may include any of wireless LAN, Wi-Fi, Bluetooth, Zigbee, Wi-Fi direct (WFD), ultra wideband (UWB), infrared data association (IrDA), Bluetooth low energy (BLE), and near field communication (NFC), but the short-distance communication technology is not limited thereto.

When the ultrasound probe 100 is wirelessly connected to a plurality of ultrasound image providing apparatuses via different respective communication channels, the communication unit 140 may transmit each of a plurality of transmission streams to a corresponding one of the plurality of ultrasound image providing apparatuses via the different respective communication channels. In this case, the plurality of transmission streams may be transmission streams which are generated by the control unit 130 processing ultrasound image data, based on respective characteristics of the plurality of ultrasound image providing apparatuses.

Moreover, as illustrated in FIG. 30, the ultrasound probe 100 according to various exemplary embodiments may further include at least one selected from a storage unit (also referred to herein as a "storage device" and/or as a "storage") 150, a user input unit (also referred to herein as a "user input device") 160, and an output unit (also referred to herein as an "output device") 170.

The storage unit 150 stores various pieces of information processed by the ultrasound probe 100. For example, the storage unit 150 may store medical data, such as input/output ultrasound data and ultrasound images, associated with a diagnosis of an object, and may also store an algorithm or a program which is executed in the ultrasound probe 100.

The storage unit 150 may be configured with any of various kinds of storage mediums such as a flash memory, a hard disk, an EEPROM, etc. Also, the ultrasound probe 100 may operate web storage or a cloud server which performs a storage function of the storage unit 150 on a web.

Moreover, the storage unit 150 according to an exemplary embodiment may map one of first and second modes to each of a plurality of applications, and store the mapped mode. The control unit 130 may select a mode, which is stored to be mapped to an application used by the ultrasound probe 100, from among the first and second modes.

Parameter values, associated with ultrasound image quality, which are respectively mapped to various user inputs, may be stored in the storage unit 150. The control unit 130 may search for pre-stored data, based on a user input, and search the data for at least one parameter value corresponding to the user input.

The storage unit 150 may store transmission speeds of ultrasound image data which are mapped to parameter values associated with the ultrasound image quality. When at least one parameter value associated with the ultrasound image quality is determined, the control unit 130 may search for pre-stored data, based on the determined parameter value, and search the data for a transmission speed corresponding to the parameter value.

Moreover, the transmission speeds of the ultrasound image data which are respectively mapped to various user inputs may be stored in the storage unit 150. The control unit 130 may search for pre-stored data, based on a user input, and search the data for a transmission speed of the ultrasound image data that corresponds to the user input.

The parameter values, associated with the ultrasound image quality, which are respectively mapped to the transmission speeds of the ultrasound image data, may be stored in the storage unit 150. When a transmission speed of the ultrasound image data is determined, the control unit 130 may search for pre-stored data, based on the determined transmission speed, and search the data for at least one parameter value that corresponds to the transmission speed.

Moreover, the storage unit 150 may store information about respective characteristics of a plurality of ultrasound image providing apparatuses which are connectable to the ultrasound probe 100. The storage unit 150 may store information about a characteristic of an ultrasound image providing apparatus, which is mapped to a transmission speed of ultrasound image data and a parameter value associated with a quality of the ultrasound image data. The control unit 130 may search for pre-stored data, based on the information about the characteristic of the ultrasound image providing apparatus, and search the data for a transmission speed and a parameter value, which is suitable for the ultrasound image providing apparatus.

Alternatively, the storage unit 150 may store information about a method of processing ultrasound image data for generating a transmission stream which is to be transmitted to an ultrasound image providing apparatus, which is mapped to information about a characteristic of the ultrasound image providing apparatus. For example, the storage unit 150 may store a resolution of an ultrasound image, generated from a transmission stream received from the ultrasound image providing apparatus, which is mapped to the information about the characteristic of the ultrasound image providing apparatus. The control unit 130 may search for pre-stored data, based on the information about the characteristic of the ultrasound image providing apparatus and generate a transmission stream which is suitable for the ultrasound image providing apparatus by processing the ultrasound image data, based on found data.

The user input unit 160 denotes a device that receives data for controlling the ultrasound probe 100.

The user input unit 160 may receive a user input that selects an operation of determining which of a quality of an ultrasound image and a transmission speed of a frame is more important. The control unit 130 may select one from among a first mode and a second mode, based on a user input received by the user input unit 160. When the first mode is selected, the user input unit 160 may adjust the at least one parameter value, based on a change in a bandwidth of a communication channel. When the second mode is selected, the user input unit 160 may adjust a transmission speed, based on the change in the bandwidth of the communication channel.

Alternatively, the user input unit 160 may receive a user input for determining at least one selected from at least one parameter value associated with a quality of ultrasound image data and a transmission speed of the ultrasound image data.

The user input unit 160 may include any of hardware elements such as a keypad, a mouse, a touch pad, a trackball, a jog switch, but is not limited thereto. As another example, the user input unit 160 may further include any of various input devices such as an electrocardiogram (ECG) measurement module, a breath measurement sensor, a voice recognition sensor, a gesture recognition sensor, a fingerprint recognition sensor, an iris recognition sensor, a depth sensor, a distance sensor, etc.

The output unit 170 may output any of various types of information processed by the ultrasound probe 100. For example, the output unit 170 may output the various information, processed by the ultrasound probe 100, in the form of sound, light, vibration, images, or letters. For example, the output unit 170 may display the various information, processed by the ultrasound probe 100, on a screen. The output unit 170 may display a user interface (UI) or a graphic user interface (GUI), associated with a function setting of the ultrasound probe 100, on a screen.

Moreover, as illustrated in FIG. 30, the ultrasound image providing apparatus 200 connected to the ultrasound probe 100 according to various exemplary embodiments may include a communication unit (also referred to herein as a "communicator") 210, a control unit (also referred to herein as a "controller") 220, a display (also referred to herein as a "display device" and/or as a "display unit") 230, a storage unit (also referred to herein as a "storage device" and/or as a "storage") 240, and a user input unit (also referred to herein as a "user input device") 250.

The ultrasound image providing apparatus 200 may communicate with the ultrasound probe 100 via the communication unit 210. The communication unit 210 may receive ultrasound image data from the ultrasound probe 100 and transmit a control signal to the ultrasound probe 100.

The control unit 220 may control an overall operation of the ultrasound image providing apparatus 200. For example, the control unit 220 may control at least one selected from among the communication unit 210, the control unit 220, the display 230, the storage unit 240, and the user input unit 250.

The display 230 may display information processed by the ultrasound image providing apparatus 200. For example, the display 230 may display an ultrasound image generated from the ultrasound image data received from the ultrasound probe 100 and/or display a user interface associated with the ultrasound image.

In order to display the information processed by the ultrasound image providing apparatus 200, the display 230 may include at least one selected from among a liquid crystal display (LCD), a thin film transistor-liquid crystal display, an organic light-emitting diode (OLED), a flexible display, a 3D display, and an electrophoretic display.

The display 230 may be configured in the form of a touch screen which forms a layer structure with a touch pad.

The display 230 may display a user interface for receiving various user inputs. For example, the display 230 may display at least one selected from among a user interface for receiving a user input that determines a parameter value associated with a quality of ultrasound image data, a user interface for receiving a user input that determines a transmission speed at which the ultrasound image data is transmitted, a user interface for receiving a user input that determines a communication scheme according to which the ultrasound probe 100 transmits the ultrasound image data, and a user interface for providing information about the ultrasound probe 100 which communicates with the ultrasound image providing apparatus 200.

The storage unit 240 may store a program for processing and control performed by the control unit 220 and/or store data input or output to or from the ultrasound image providing apparatus 200. For example, the storage unit 240 may store an ultrasound image displayed by the ultrasound image providing apparatus 200.

The user input unit 250 may denote a device for inputting data used for a user to control the ultrasound image providing apparatus 200 or the ultrasound probe 100. For example, the user input unit 250 may include any of a keypad, a dome switch, a button, a wheel, a trackball, a touch pad, a jog wheel, a jog switch, and/or the like.

The user input unit 250 may receive at least one selected from among a user input that determines a parameter value associated with a quality of ultrasound image data, a user input that determines a transmission speed at which the ultrasound image data is transmitted, a user input that determines a communication scheme according to which the ultrasound probe 100 transmits the ultrasound image data, and a user input for the ultrasound probe 100 which communicates with the ultrasound image providing apparatus 200.

Figure 31:
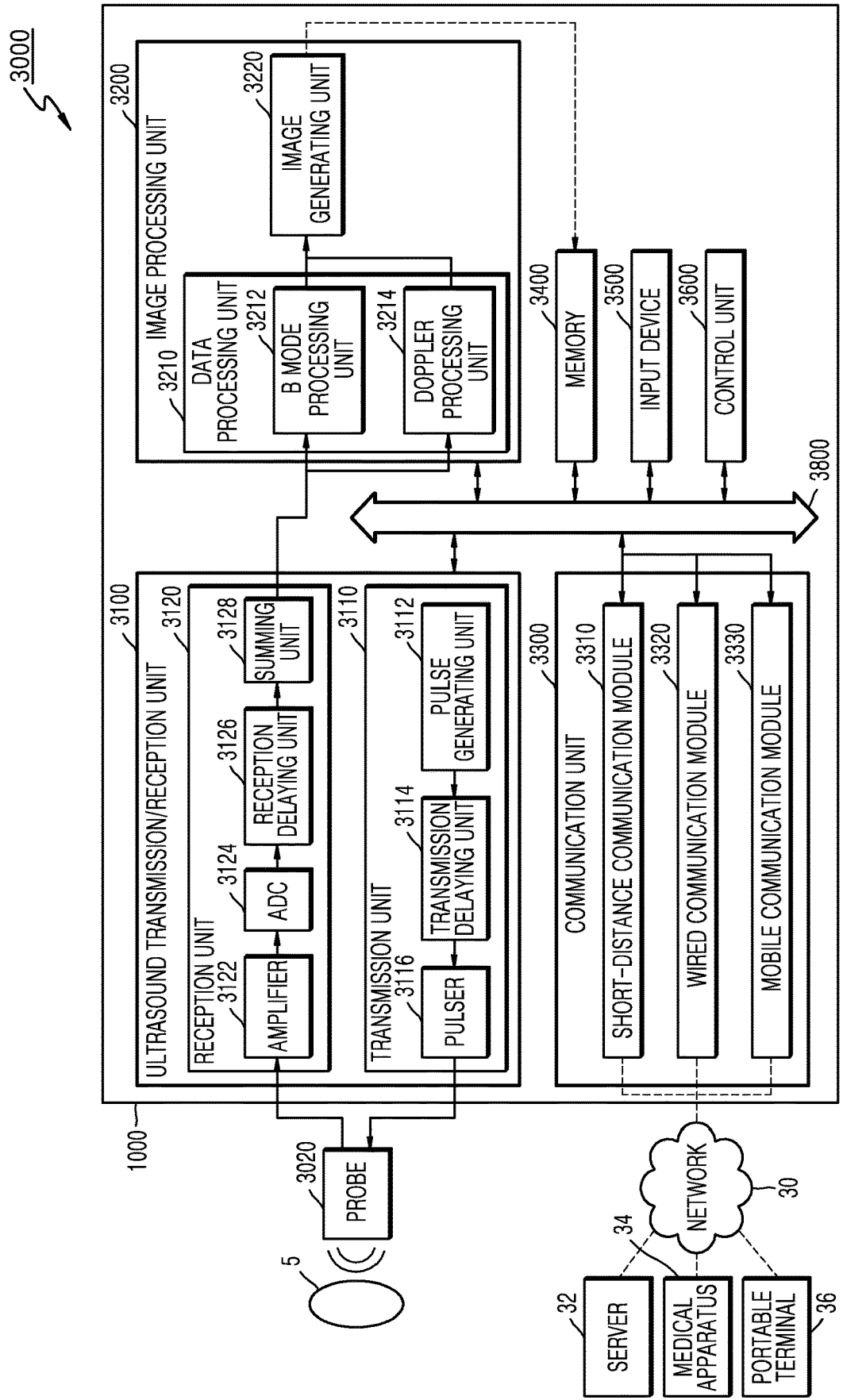
FIG. 31 is a block diagram of an ultrasound diagnostic apparatus which is applicable to various exemplary embodiments.

FIG. 31 is a block diagram of an ultrasound diagnostic apparatus which is applicable to an ultrasound probe, according to various exemplary embodiments.

An ultrasound probe 100 according to various exemplary embodiments may be wirelessly connected to an ultrasound diagnostic apparatus 3000 of FIG. 31, and the ultrasound image providing apparatus 200 connected to the ultrasound probe 100 may be included in the ultrasound diagnostic apparatus 3000 of FIG. 31.

The ultrasound probe 100 and ultrasound image providing apparatus 200 of FIG. 29 or 30 may perform some or all of functions performed by the ultrasound diagnostic apparatus 3000 of FIG. 31.

The ultrasound transmission/reception unit 110, signal processing unit 120, and control unit 130 of FIG. 29 may include some or all of elements included in a probe 3020, an ultrasound transmission/reception unit 3100, an image processing unit 3200, and a control unit 3600 of FIG. 31, and may perform some or all of functions performed by the probe 3020, ultrasound transmission/reception unit 3100, image processing unit 3200, and control unit 3600 of FIG. 31.

Moreover, the control unit 220 of FIG. 30 may include some or all of the ultrasound transmission/reception unit 3100, the image processing unit 3200, and the control unit 3600 of FIG. 31 and may perform some or all of functions performed by the ultrasound transmission/reception unit 3100, the image processing unit 3200, and the control unit 3600 of FIG. 31.

The communication unit 210 of FIG. 30 may correspond to the communication unit 3300 of FIG. 31, and the display 230 of FIG. 30 may correspond to the display 230 of FIG. 30. The storage unit 240 may correspond to a memory 3400 of FIG. 31, and the user input unit 250 of FIG. 30 may correspond to an input device 3500 of FIG. 31.

FIG. 31 is a block diagram of an ultrasound diagnostic apparatus 3000 which is applicable to various exemplary embodiments.

FIG. 31 is a block diagram showing a configuration of an ultrasound diagnosis apparatus 3000, according to an exemplary embodiment. Referring to FIG. 31, the ultrasound diagnosis apparatus 3000 may include a probe 3020, an ultrasound transceiver 3100, an image processor 3200, a communication module 330, a display (not shown), a memory 3400, an input device 3500, and a controller 3600, which may be connected to one another via buses 3800.

The ultrasound diagnosis apparatus 3000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 3020 transmits ultrasound waves toward an object 5 in response to a driving signal applied by the ultrasound transceiver 3100 and receives echo signals reflected by the object 5. The probe 3020 includes a plurality of transducers, and the plurality of transducers oscillate in response to electric signals and generate acoustic energy, that is, ultrasound waves. Furthermore, the probe 3020 may be connected to the main body of the ultrasound diagnosis apparatus 3000 by wire or wirelessly. According to one or more exemplary embodiments, the ultrasound diagnosis apparatus 3000 may include a plurality of probes 3020.

A transmitter 1110 supplies a driving signal to the probe 3020. The transmitter 3110 includes a pulse generator 3112, a transmission delaying unit (also referred to herein as a "transmission delayer") 3114, and a pulser 3116. The pulse generator 3112 generates pulses for forming transmission ultrasound waves based on a predetermined pulse repetition frequency (PRF), and the transmission delaying unit 3114 delays the pulses by delay times necessary for determining transmission directionality. The pulses which have been delayed correspond to a plurality of piezoelectric vibrators included in the probe 3020, respectively. The pulser 3116 applies a driving signal (or a driving pulse) to the probe 3020 based on timing that corresponds to each of the pulses which have been delayed.

A receiver 3120 generates ultrasound data by processing echo signals received from the probe 3020. The receiver 3120 may include an amplifier 3112, an analog-to-digital converter (ADC) 3124, a reception delaying unit (also referred to herein as a "reception delayer") 3126, and a summing unit (also referred to herein as a "summer") 3128. The amplifier 3122 amplifies echo signals in each channel, and the ADC 3124 performs analog-to-digital conversion with respect to the amplified echo signals. The reception delaying unit 3126 delays digital echo signals output by the ADC 3124 by delay times necessary for determining reception directionality, and the summing unit 3128 generates ultrasound data by summing the echo signals processed by the reception delaying unit 3126. Also, according to one or more exemplary embodiments, the receiver 3120 may not include the amplifier 3122. In this aspect, if the sensitivity of the probe 3020 or the capability of the ADC 3124 to process bits is enhanced, the amplifier 3122 may be omitted.

The image processor 3200 generates an ultrasound image by scan-converting ultrasound data generated by the ultrasound transceiver 3100. The ultrasound image may include not only a grayscale ultrasound image obtained by scanning an object in any of an amplitude (A) mode, a brightness (B) mode, and a motion (M) mode, but also a Doppler image showing a movement of an object via a Doppler effect. The Doppler image may include any of a blood flow Doppler image showing flow of blood (also referred to as a color Doppler image), a tissue Doppler image showing a movement of tissue, or a spectral Doppler image showing a moving speed of an object as a waveform.

A B mode processor 3212 in a data processor 3210 extracts B mode components from ultrasound data and processes the B mode components. An image generator 3220 may generate an ultrasound image that indicates signal intensities as brightness based on the extracted B mode components.

Similarly, a Doppler processor 3214 in a data processor 3210 may extract Doppler components from ultrasound data, and the image generator 3220 may generate a Doppler image that indicates a movement of an object as colors or waveforms based on the extracted Doppler components.

According to an exemplary embodiment, the image generator 3220 may generate a three-dimensional (3D) ultrasound image via volume-rendering with respect to volume data and may also generate an elasticity image by imaging deformation of the object 5 due to pressure. Furthermore, the image generator 3220 may display various pieces of additional information in an ultrasound image by using text and graphics. In addition, the generated ultrasound image may be stored in the memory 3400.

A display (not shown) displays the generated ultrasound image. The display may display not only an ultrasound image, but also various pieces of information processed by the ultrasound diagnosis apparatus 3000 on a screen image via a graphical user interface (GUI). In addition, the ultrasound diagnosis apparatus 3000 may include two or more displays according to one or more exemplary embodiments.

The communication module 3300 is connected to a network 30 by wire or wirelessly to communicate with an external device or a server. The communication module 3300 may exchange data with a hospital server or another medical apparatus in a hospital, which is connected thereto via a PACS. Furthermore, the communication module 3300 may perform data communication according to the digital imaging and communications in medicine (DICOM) standard.

The communication module 3300 may transmit or receive data related to diagnosis of an object, e.g., any of an ultrasound image, ultrasound data, and/or Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 3300 may receive information about a diagnosis history or medical treatment schedule of a patient from a server and utilizes the received information to diagnose the patient. Furthermore, the communication module 3300 may perform data communication not only with a server or a medical apparatus in a hospital, but also with a portable terminal of a medical doctor or patient.

The communication module 3300 is connected to the network 30 by wire or wirelessly to exchange data with any of a server 32, a medical apparatus 34, and/or a portable terminal 36. The communication module 3300 may include one or more components for communication with external devices. For example, the communication module 3300 may include a local area communication module (also referred to herein as a "short-distance communication module") 3310, a wired communication module 3320, and a mobile communication module 3330.

The local area communication module 3310 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 3320 refers to a module for communication that is performed by using electric signals or optical signals. Examples of wired communication techniques according to an exemplary embodiment may include communication via a twisted pair cable, a coaxial cable, an optical fiber cable, and an Ethernet cable.

The mobile communication module 3330 transmits or receives wireless signals to or from at least one selected from among a base station, an external terminal, and a server on a mobile communication network. The wireless signals may be voice call signals, video call signals, or various types of data for transmission and reception of text/multimedia messages.

The memory 3400 stores various data processed by the ultrasound diagnosis apparatus 3000. For example, the memory 3400 may store medical data related to diagnosis of an object, such as ultrasound data and an ultrasound image that are input or output, and may also store algorithms or programs which are to be executed in the ultrasound diagnosis apparatus 3000.

The memory 3400 may include any of various storage media, e.g., a flash memory, a hard disk drive, EEPROM, etc. Furthermore, the ultrasound diagnosis apparatus 3000 may utilize web storage or a cloud server that performs the storage function of the memory 3400 online.

The input device 3500 refers to a means via which a user inputs data for controlling the ultrasound diagnosis apparatus 3000. The input device 3500 may include any of various hardware components, such as a keypad, a mouse, a touch pad, a touch screen, and a jog switch. However, exemplary embodiments are not limited thereto, and the input device 3600 may further include any of various other input units, including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 3600 may control all operations of the ultrasound diagnosis apparatus 3000. In particular, the controller 3700 may control operations among the probe 3020, the ultrasound transceiver 3100, the image processor 3200, the communication module 3300, the display, the memory 3400, and the input device 3500 shown in FIG. 1.

All or some of the probe 3020, the ultrasound transceiver 3100, the image processor 3200, the communication module 3300, the display, the memory 3400, the input device 3500, and the controller 3600 may be implemented as software modules. However, exemplary embodiments are not limited thereto, and some of the components stated above may be implemented as hardware components. In particular, the controller 3600 may be implemented as a microprocessor or as integrated circuitry. Furthermore, at least one selected from among the ultrasound transceiver 3100, the image processor 3200, and the communication module 3300 may be included in the controller 3600. However, exemplary embodiments are not limited thereto.

Figure 32:
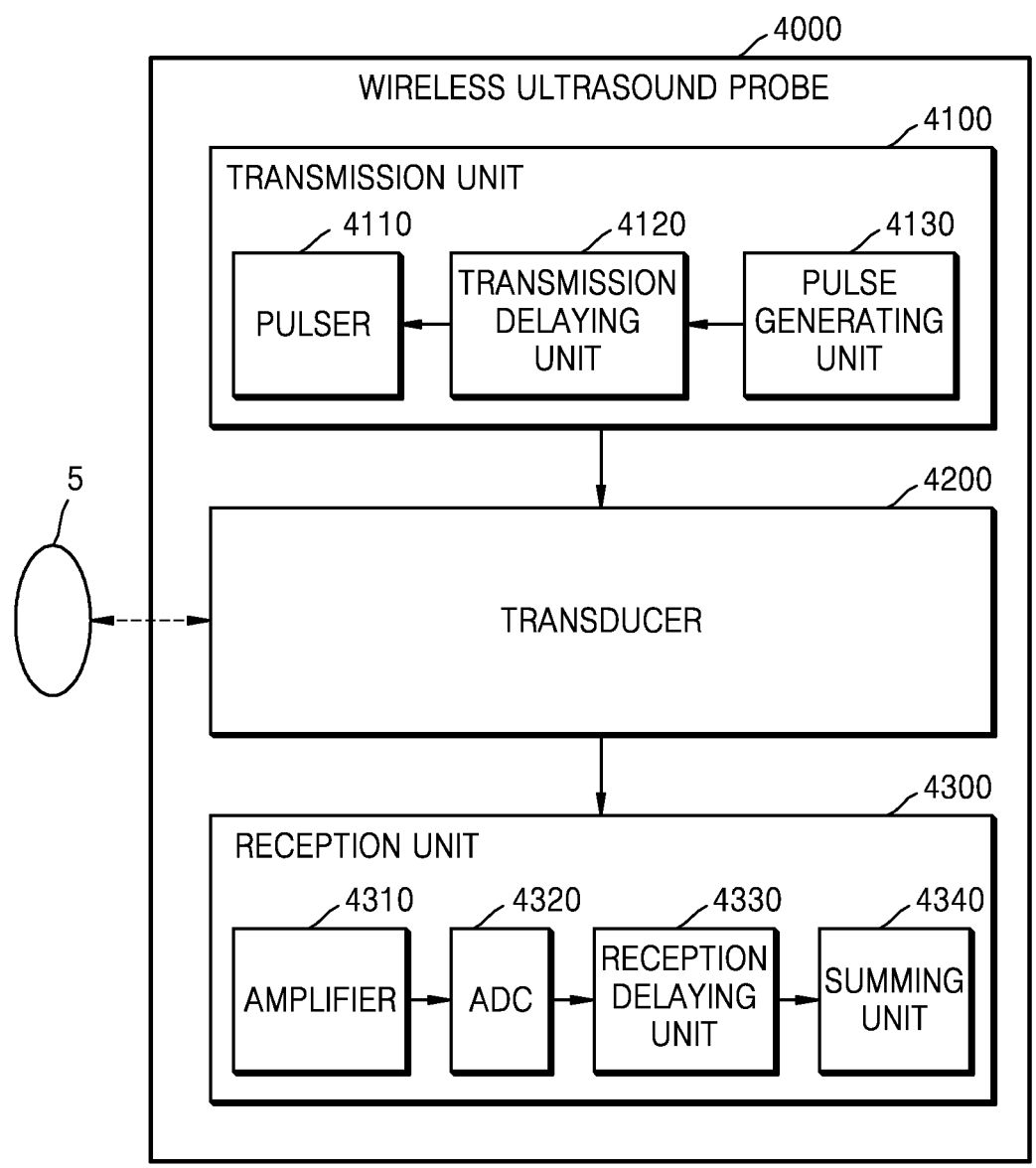
FIG. 32 is a block diagram of a wireless ultrasound probe which is applicable to various exemplary embodiments.

FIG. 32 is a block diagram showing a configuration of a wireless probe 4000, according to an exemplary embodiment. As described above with reference to FIG. 1, the wireless probe 4000 may include a plurality of transducers, and, according to one or more exemplary embodiments, may include some or all of the components of the ultrasound transceiver 100 shown in FIG. 1.

The wireless probe 4000 according to the exemplary embodiment shown in FIG. 32 includes a transmitter 4100, a transducer 4200, and a receiver 4300. Since descriptions thereof are given above with reference to FIG. 31, detailed descriptions thereof will be omitted here. In addition, according to exemplary embodiments, the wireless probe 4000 may selectively include a reception delaying unit (also referred to herein as a "reception delayer") 4330 and a summing unit (also referred to herein as a "summer") 4340.

The wireless probe 4000 may transmit ultrasound signals toward the object 5, receive echo signals from the object 5, generate ultrasound data, and wirelessly transmit the ultrasound data to the ultrasound diagnosis apparatus 3000 shown in FIG. 31.

One or more exemplary embodiments may be implemented in the form of a storage medium that includes computer executable instructions, such as program modules, being executed by a computer. Computer-readable media may be any available media that may be accessed by the computer and includes both volatile and nonvolatile media, and removable and non-removable media. In addition, the computer-readable media may include computer storage media and communication media. Computer storage media includes both the volatile and non-volatile, and removable and non-removable media implemented as any method or technology for storage of information such as computer readable instructions, data structures, program modules, or other data. The medium of communication is typically computer-readable instructions, and other data in a modulated data signal such as data structures, or program modules, or other transport mechanism and includes any information delivery media.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments has been described with reference to the figures, it will be understood by those of ordinary skill in the art that various changes in form and details may be made therein without departing from the spirit and scope of the present inventive concept, as defined by the following claims.

What is claimed is:

1. An ultrasound probe that is wirelessly connected to an ultrasound image providing apparatus via a communication channel, the ultrasound probe comprising:
an ultrasound transceiver configured to transmit an ultrasound signal toward an object, and to receive an echo signal reflected from the object;
a signal processor configured to process the received echo signal and generate ultrasound image data by using the processed echo signal;
a communicator configured to transmit the ultrasound image data to the ultrasound image providing apparatus; and
a controller configured to:
control the communicator to wirelessly connect the ultrasound probe to the ultrasound image providing apparatus by using a first communication scheme,
acquire bandwidth information that relates to the communication channel by using the first communication scheme,
determine at least one parameter value that relates to a quality of an ultrasound image, based on the bandwidth information,
control the signal processor to generate the ultrasound image data that relates to the object, based on the at least one parameter value,
search for pre-stored data with respect to a transmission speed of the ultrasound image data associated with the quality of the ultrasound image, and
determine a transmission speed that corresponds to the determined at least one parameter value by mapping the at least one parameter value to the searched pre-stored data,
wherein, when the transmission speed is lower than a predetermined threshold speed, the controller is further configured to control the communicator to:
wirelessly connect the ultrasound probe to the ultrasound image providing apparatus by using a second communication scheme in place of the first communication scheme, and
transmit the ultrasound image data to the ultrasound image providing apparatus by using the second communication scheme.

2. An ultrasound probe that is wirelessly connected to an ultrasound image providing apparatus, the ultrasound probe comprising:
an ultrasound transceiver configured to transmit an ultrasound signal toward an object, and to receive an echo signal reflected from the object;
a signal processor configured to process the received echo signal and generate ultrasound image data by using the processed echo signal;
a communicator configured to transmit the ultrasound image data to the ultrasound image providing apparatus; and
a controller configured to:
control the communicator to wirelessly connect the ultrasound probe to the ultrasound image providing apparatus by using a first communication scheme,
determine at least one parameter value that relates to a quality of an ultrasound image, based on a user input,
control the signal processor to generate the ultrasound image data that relates to the object, based on the determined at least one parameter value,
search for pre-stored data with respect to a transmission speed of the ultrasound image data associated with the quality of the ultrasound image, and
determine a transmission speed that corresponds to the determined at least one parameter value by mapping the at least one parameter value to the searched pre-stored data,
wherein the at least one parameter value comprises at least one selected from among number of scan lines that constitutes one frame of the ultrasound image, number of sampling points which are set on each of the scan lines, and number of bits which are generated by quantizing the ultrasound image data acquired from the sampling points,
wherein, when the transmission speed is lower than a predetermined threshold speed, the controller is further configured to control the communicator to:
wirelessly connect the ultrasound probe to the ultrasound image providing apparatus by using a second communication scheme, and
transmit the ultrasound image data to the ultrasound image providing apparatus by using the second communication scheme in place of the first communication scheme.

3. The ultrasound probe of claim 2, wherein,
the ultrasound probe is connected to a plurality of ultrasound image providing apparatuses, including the ultrasound image providing apparatus, via different communication channels,
the controller is further configured to generate a plurality of transmission streams by processing the ultrasound image data, based on respective characteristics of each of the plurality of ultrasound image providing apparatuses, and
the communicator is further configured to transmit each of the plurality of transmission streams to a corresponding one of the plurality of ultrasound image providing apparatuses via a corresponding one of the different communication channels.

4. An ultrasound probe that is wirelessly connected to an ultrasound image providing apparatus, the ultrasound probe comprising:
an ultrasound transceiver configured to transmit an ultrasound signal toward an object, and to receive an echo signal reflected from the object;
a signal processor configured to process the received echo signal;
a controller configured to:
acquire capability information of the ultrasound image providing apparatus from the ultrasound image providing apparatus, wherein the capability information includes information indicating at least one of types of data which are to be processed by the ultrasound image providing apparatus, a quality of ultrasound image data capable of being supported by the ultrasound image providing apparatus, wireless communication schemes capable of being supported by the ultrasound image providing apparatus, a bandwidth available to the ultrasound image providing apparatus, communication channels capable of being supported by the ultrasound image providing apparatus,
determine a transmission speed for transmitting ultrasound image data, based on the acquired capability information of the ultrasound image providing apparatus,
determine at least one parameter value that relates to a quality of an ultrasound image, based on the determined transmission speed, and control the ultrasound transceiver and the signal processor to generate ultrasound image data that relates to the object, based on the determined at least one parameter value; and a communicator configured to transmit the ultrasound image data to the ultrasound image providing apparatus at the determined transmission speed, wherein the at least one parameter value comprises at least one selected from among number of scan lines that constitutes one frame of the ultrasound image, number of sampling points which are set on each of the scan lines, and number of bits which are generated by quantizing the ultrasound image data acquired from the sampling points.

5. The ultrasound probe of claim 4, wherein the controller is further configured to decrease the at least one parameter value, based on a reduction in the transmission speed.

6. The ultrasound probe of claim 4, wherein
the ultrasound probe is connected to a plurality of ultrasound image providing apparatuses, including the ultrasound image providing apparatus, via different communication channels,
the controller is further configured to generate a plurality of transmission streams by processing the ultrasound image data, based on respective characteristics of each of the plurality of ultrasound image providing apparatuses, and
the communicator is further configured to transmit each of the plurality of transmission streams to a respective one of the plurality of ultrasound image providing apparatuses via a respective one of the different communication channels.

7. An ultrasound probe comprising:
an ultrasound transceiver configured to transmit an ultrasound signal toward an object and to receive an echo signal reflected from the object;
a signal processor configured to process the received echo signal in order to generate ultrasound image data;
a controller configured to:
acquire capability information of an ultrasound image providing apparatus that is wirelessly connected to the ultrasound probe, wherein the capability information includes information indicating at least one of types of data which are to be processed by the ultrasound image providing apparatus, a quality of ultrasound image data capable of being supported by the ultrasound image providing apparatus, wireless communication schemes capable of being supported by the ultrasound image providing apparatus, a bandwidth available to the ultrasound image providing apparatus, communication channels capable of being supported by the ultrasound image providing apparatus, and
determine a transmission speed of the generated ultrasound image data, based on the acquired capability information of the ultrasound image providing apparatus; and
a communicator configured to transmit the generated ultrasound image data to the ultrasound image providing apparatus at the determined transmission speed.

* * * * *